(12) United States Patent
Schoenau et al.

(10) Patent No.: US 6,242,261 B1
(45) Date of Patent: Jun. 5, 2001

(54) ASSESSMENT OF ION AVAILABILITY IN HETEROGENEOUS MEDIA USING ION-EXCHANGE MEMBRANES

(75) Inventors: Jeffrey John Schoenau, Central Butte; Weize Huang, Saskatoon, both of (CA)

(73) Assignee: University of Saskatchewan, Saskatchewan (CA)

( * ) Notice: Subject to any disclaimer, the term of this patent is extended or adjusted under 35 U.S.C. 154(b) by 0 days.

(21) Appl. No.: 08/284,590
(22) PCT Filed: Feb. 10, 1993
(86) PCT No.: PCT/CA93/00056
§ 371 Date: Aug. 10, 1994
§ 102(e) Date: Aug. 10, 1994
(87) PCT Pub. No.: WO93/16382
PCT Pub. Date: Aug. 19, 1993

Related U.S. Application Data

(63) Continuation-in-part of application No. 08/119,319, filed on Sep. 9, 1993, now abandoned, which is a continuation of application No. 07/833,315, filed on Feb. 10, 1992, now abandoned.

(51) Int. Cl.$^7$ .................................................. G01N 33/24
(52) U.S. Cl. .............................. 436/26; 436/28; 436/171; 436/178; 422/61; 210/263; 210/638
(58) Field of Search .................... 422/61; 436/28, 436/26, 171, 178; 210/638, 263; 521/25

(56) References Cited

U.S. PATENT DOCUMENTS

Re. 33,487   12/1990   Marks .................................... 422/61

(List continued on next page.)

FOREIGN PATENT DOCUMENTS 0385797   9/1990   (EP).
2187838   9/1987   (GB).

OTHER PUBLICATIONS

H. James, "The Determination of Trace Amounts of Cobalt and Other Metals in High–purity Water by Using Ion–exchange Membranes", *Analyst*, vol. 98, pp. 274–288 (Apr. 1973).

(List continued on next page.)

*Primary Examiner*—Nina Bhat
(74) *Attorney, Agent, or Firm*—Ratner & Prestia

(57) ABSTRACT

The invention relates to a kit for the measurement of anion, cation or zwitterion availability in a medium or for the measurement of free inorganic ions in disrupted cells from plant or animal tissue. The kit comprises ion-exchange material having a measurable ion uptake potential for immobilizing available ions from the medium on the material following contact on the material with the medium or suspension. It also comprises means to remove particulate solids from the material after having contacted the medium with the material. Preferably, the ion-exchange material is cation and/or anion-exchange material in the form of rigid or flexible films, sheets, membranes or the like. The invention also relates to a method for the on-site in situ measurement of anion and/or cation availability in a solid medium and to a method for measuring free organic ions in cells from plant or animal tissue. It also relates to ion-exchange material for immobilizing available ions in soil, sediment or water media and to a cation and/or anion-exchange membrane buried underneath the surface of a soil sample or site, the membrane being in ion-exchange relationship with available ions in the soil. The present invention represents an improvement over the prior art in that it provides means for quickly determining ion availability in a particular media without the necessity of collecting media samples for laboratory testing.

70 Claims, 37 Drawing Sheets

U.S. PATENT DOCUMENTS

| | | | |
|---|---|---|---|
| 1,775,134 | 9/1930 | Malsbury | 422/28 |
| 3,616,409 | 10/1971 | Tosteson | 204/195 |
| 3,714,344 | 1/1973 | Brown | 422/28 |
| 4,126,417 | 11/1978 | Edwards | 422/56 |
| 4,201,549 | 5/1980 | Tepe et al. | 23/230 |
| 4,775,513 | 10/1988 | Marks | 422/61 |
| 4,816,161 | 3/1989 | Olness et al. | 210/638 |
| 4,962,025 | 10/1990 | Moldowan | 435/25 |
| 5,028,543 | 7/1991 | Finch et al. | 436/124 |

OTHER PUBLICATIONS

"A simple ion–exchange resin procedure for extracting plant–available elements from soil", *Plant and Soil*, 46, pp. 665–669, (1977).

Yang et al., "Phytoavailability Soil Test: Development and Verification of Theory", *Soil Sci. Soc. Am. J.*, 55, pp 1358–1365, (1991).

Skogley et al. "The Phytoavailability Soil Test—PST", *Commun. in Soil Sci. Plant Anal.*, 21(13–16), pp 1229–1243, (1990).

Sagger et al., "A simplified resin membrane technique for extracting phosphorus from soils", *Fertilizer Research* 24, pp. 173–180, (1990).

Skogley, "The Universal Bioavailability Environment/Soil Test/UNIBEST", *International Symposium on Soil Testing & Plant Analysis in the Global Comm.*, Aug. 22–27, 1991, Orlando, Florida.

Searle, "The Determination of Phosphate–Extractable Sulphate in Soil with an Anion–Exchange Membrane", *Commun. in Soil Sci. Plant Anal.*, 19(13), pp. 1477–1493 (1988).

van Raij et al, "Extraction of Phosphorus, Potassium, Calcium and Magnesium From Soils By An Ion–Exchange Resin Procedure", *Commun. in Soil Sci. Plant Anal.*, 17(5), pp. 547–566 (1986).

Cooke et al, "Use of Anion–Exchange Resin for the Assessment of Available Soil Phosphate", pp. 308–312 (recd. for pub. Oct. 12, 1962).

Saunders, "Extraction of Soil Phosphate by Anion–exchange Membrane", *N.Z.J. Agric. Res.*, 7, pp. 427–431 (recd. for pub. May 12, 1964).

Abrams et al., "Bioavailability Index for Phosphorus Using Ion Exchange Resin Impregnated Membranes", *Soil Sci. Soc. Am. J.*, vol. 56, pp 1532–1537 (Sep.–Oct. 1992).

International Search Report for PCT/CA93/00056, Dated: Jun. 11, 1993 (EPO).

ASSESSMENT OF ION AVAILABILITY IN HETEROGENEOUS MEDIA USING ION-EXCHANGE MEMBRANES

This application is a 371 of PCT/CA93/00056 filed Feb. 10, 1993, which is a continuation-in-part of Ser. No. 08/119,319 filed Sep. 9, 1993, now abandoned, which is a continuation of 07/833,315 filed Feb. 10, 1992, now abandoned.

FIELD OF THE INVENTION

The invention relates to techniques for the measurement of available ions in various media such as water, soil and sediments or for the measurement of free ions in disrupted cells. The techniques are based on the immobilization of ions on the surface of ion-exchange material. Particularly, the invention relates to techniques useful for on-site assessment of either nutrient availability in soils or sediments or free inorganic ions in plant material.

BACKGROUND OF THE INVENTION

A good soil test is one which is simple, rapid and can remove all or a representative portion of the available nutrient pool in a wide variety of soil types. Few existing tests excel in both these requirements. Methodology which provides the best estimate of nutrient availability is often too complicated and cumbersome for routine labs making fertilizer recommendations to producers. Furthermore, many existing P, N, S and K tests do not take into account all factors affecting nutrient availability in soil. Some tests are specific to a region or soil type, performing poorly when transposed to other environments. For example, P and K tests which are based on chemical removal of specific P and K fractions are usually limited in geographic scope since the importance of a fraction may vary depending on the physical and chemical environment of the soil.

Anion-exchange resins are considered one of the better indices of plant available P. Cation-exchange resins have also been used for extraction of available K in soils. However, conventional resins in bead form are generally difficult to separate from soil and are not well-suited for routine analysis. Still, there are numerous prior art references teaching the use of ion-exchange resin beads to evaluate nutrient availability in soil samples.

In Brazilian Patent 8605998, nutrients are extracted from soil samples for analysis using capsules with at least two opposite fabric walls containing standard amounts of ion-exchange resins which are placed in a beaker with a sealed cover. Measured amounts of dry soil and a fixed amount of water are added in the beaker, placed on a special tray and agitated in a specially built machine by free tumbling. Beakers are taken to a washer-separator and washed with deionized water to remove soil and other particles. The capsules are then transferred to a clean beaker containing a solution of NaCl and HCl. The resulting solution contains the substances to be analyzed and the resin is regenerated by washing with successive solutions to remove cations and anions and restore its exchange capacity.

A technique of this type has at least two major drawbacks. Firstly, there is the necessity of bringing a soil sample to the laboratory and to dry such soil sample, a step which can require up to three days. Secondly, the use of resin beads is extremely impractical as it is very difficult to wash from the beads the soil that could have accumulated during agitation of the capsules containing the resin beads in the soil suspension. Also the bags are susceptible to fraying and rupture due to abrasion by the soil during shaking.

U.S. Pat. No. 4,816,161 relates to an ion extractor comprising a tube filled with cation or anion-exchange resin beads. It is used for extracting ions from streams, lakes and marine sediments. The resin beads are retained in a dialysis tube by support tubes which each have a screen of an appropriately-sized mesh attached to the interior ends by means of a suitable adhesive. Hence, when it is used, the extractor is placed in an aqueous suspension of the soil sample to be analyzed. Once the resin has been contacted with the soil suspension, it is eluted with acid in order to leach the exchange ion from the exchange sites and to return the resin to a homoionically saturated exchange state for subsequent reuse. The sample leachate is collected in tubes and analyzed to determine the concentrations of constituents of interest. Again, in this type of system, it is required to produce a soil suspension as direct contact between the soil and the ion-exchange resin beads is avoided.

U.S. Pat. No. 4,775,513 and re-issue 33,487 relate to a device for water treatment that uses a water-tight container of flexible material containing ion-exchange material. The ion-exchange material can be selected from silicates, clays and synthetic resin beads. The invention uses colorimetry to determine the exhaustion of the ion-exchange capacity of the resin beads. The container is filled with water and shaken to allow contact between the beads and the ions.

It is suggested to use the device described in U.S. Pat. No. 4,775,513 as a soil-testing device. However, the device is impractical as the chemicals to be tested for must first be extracted from the soil and it is necessary to filter the soil extract prior to submitting it to chemical analysis.

In Sibbesen (1977, Plant in Soil, 46:665–669), a method is described, whereby ion-exchange resin beads are sewn in nylon-netting bags which are used to extract available phosphate from a soil-water suspension.

Similarly, in Skogley et al. (1990, Communications in Soil Sciences and Plant Analysis, 21:1229–1243), the use of ion-exchange beads sewn-up in bags is reported as a test for P, K and S availability. In this procedure, soil samples are brought to the lab, water is added and a saturated paste is prepared by addition of water to the soil until it is completely saturated. As the authors note, saturated pastes are difficult to prepare uniformly and reproducibly. As well, the authors note that the test was only successful for K and S, amounts extracted were very small and difficult to measure and the extraction time required is 2 days or more. Added to the fact that the method is cumbersome and requires considerable amount of time, a special vacuum extractor instrument is required in the elution step.

In Yang et al. (1991, Soil Sci. Soc. Am. Journal, 55:1358–1365), the authors provide theoretical considerations of the testing approach outlined by Skogley et al. However, nothing is suggested to modify or improve the Skogley et al. technology.

In Saggar et al. (1990, Fertilizer Research, 24:173–180), the authors describe a simplified procedure for determining the amount of phosphate extracted from soils by using ion-exchange resin membranes in soil suspensions. Again, the procedure presents some of the drawbacks described previously.

In a paper entitled "Universal bioavailability of environment soil test" (International Symposium on Soil Testing and Plant Analysis, Aug. 22–27, 1991, Orlando, Fla.), E. O. Skogley describes research work in which anion and cation-exchange resins contained in nylon or polyester bags were buried in the face of soil pits for 6 months to study nutrient movement after an intense forest burn. As mentioned previously, there are problems in desorbing or stripping the nutrient ions of the resin beads contained in the bags. Furthermore, the bags do not work efficiently in the field as muddy soil debris often penetrate through the netting. Once inside the netting, the soil is very difficult to wash out. The washing step is extremely important as if the beads are not washed properly, the acid that is used in the elution will dissolve all of the P, S and N in the soil, not just the plant available ions on the resin, giving erroneous results. Another drawback of this type of method is the fact that soil debris are often found in the final eluent which interferes with the final analysis. Also, one of the reasons why very few papers have been published on the actual burial of resin beads in soil stems from the fact that the time period required to extract measurable amounts of nutrients from soil using beads ranges from at least 1 to 5 days and amounts to unrealistic values.

The potential of anion and cation-exchange membranes has been evaluated for routine soil-testing in laboratory environments. Essentially, the method consists of immersing the ion-exchange membrane in a water-soil suspension, washing the immersed membrane with water and diluting the membrane in an acidic solution to displace the ions immobilized on the membrane into the solution. The concentration of ions displaced in the acidic solution is then determined using standard analytical methods. This type of method is also in many respects unsatisfactory and does not solve the major drawbacks encountered with previous techniques. That is, that it is a laboratory measurement requiring that soil samples be brought to the lab and that many important soil characteristics are destroyed during drying and handling.

The laboratory-technique requires that soil samples be brought to the laboratory and dried prior to preparation of a suitable soil suspension. This procedure is cumbersome and expensive as large storage space is required for the soil samples. As well, there is the risk of contamination of the soil samples during transport and when they are laid out to dry. In plant nutrient testing assays, the time turnaround is critical for both the farmers and the fertilizer companies that depend on soil-testing facilities to evaluate the mount of fertilizer required in a particular soil. Furthermore, in a laboratory environment where soil suspensions are tested for nutrients, the only manner in which ions are drawn onto the membranes is by diffusion through the shaking of the membranes within the suspensions. The test is conducted based on a suspension that usually does not take into account the biological availability of nutrients based on the natural soil environment.

Other techniques not using ion-exchange resins or membranes for soil testing have also been described in the art. None of them has been successful at providing accurate nutrient availability index.

U.S. Pat. No. 4,201,549 describes a soil-testing technique that uses dialytic tubes. Two soil samples are placed in separate containers, each containing a dialysis unit. One dialysis tube of each unit contains lithium carbonate and the other tube contains acetic acid. The dialysis units are removed from the containers after 24 hours. The soil is washed away from the units and the solutions are analyzed.

This method suffers from numerous drawbacks. Firstly, the time required to transfer the ions from the soil onto the dialysis membranes seems to be about 24 hours, which is impractical to carry rapid on-site determination of available nutrients in soil. Furthermore, the technique does not solve the problem of taking soil samples to the laboratory as two separate soil samples must be removed from the soil. Also, the samples must be placed in separate isolated containers, which adds another cumbersome step to the method. Another problem is the fact that dialysis tubes are fragile and would not appear to be suitable to withstand repeat insertion and removal in soil samples.

U.S. Pat. No. 4,126,417 describes a method for determining the presence of a limited number of soil nutrients. The method uses paper strips treated with a pH-testing coating and a nitrate-testing coating. Typically, the strips are very insensitive and give a crude approximation of nitrogen availability in soil. Furthermore, the strips can only be used for determining pH and nitrate amounts, the other elements being washed away prior to testing.

The determination of residual profile nitrate was widely used as the criteria for fertilizer N and S recommendations in Western Canada and USA because limited leaching occurred before planting. However, organic N mineralization during the growing season by microbial processes can provide a substantial amount of inorganic N as $NH_4$—N and $NO_3$—N and improved the degree of prediction of N fertilization needs. More accurate N fertilizer recommendations could be obtained if actual contributions from mineralization in the farmers own field could be indexed, which may differ considerably from the "average" for an area. At present, this cannot be done efficiently.

Leaf tissue analysis for nitrogen (N) and phosphorus (P) is used to provide an estimate of the current N and P status of plants at the time of sampling. Various methods, with different plant parts, are used for tissue analysis for N and P. Total nutrient concentration in the tissue may be used as the diagnostic criteria, or else just a fraction such as water extractable ion. The method by which total N concentration is determined has been most widely used in the past. However, one of its major drawbacks resides in the fact that the method does not allow one to selectively measure nutrients in the plant and is complex. A good method of leaf tissue analysis should be simple and sensitive. Potassium removed by simple HCl solution and sulfate by water extractions of fresh plant tissue have shown to be good indexes of potassium and sulfur deficiencies, but require a time consuming + error prone filtration step.

The quick testing of heterogeneous liquid samples also poses some inconvenience as the presence of bulky impurities tend to affect spectroscopic measurements. In order to circumvent this problem, the heterogenous sample has to be purified prior to testing. Very often, the purification procedure is complicated and requires the use of sophisticated and expensive purification separation equipment.

In a document entitled "The determination of trace amounts of cobalt and metals in high purity water by using ion-exchange membranes" (Analyst, April 1973, Vol. 98, p. 274–288), H. James describes a method by which porous cation and anion-exchange membranes are used to analyze the presence of ions in the cooling water of nuclear reactors. The porous membranes are enclosed inside an apparatus connected to a flowline on the reactor and water continuously passes through the membranes. The author mentions that this technique has some efficiency but that it must be used within a sophisticated filtration apparatus. Hence, it was found to be essential to incorporate prefilters immediately before the ion-exchange membrane in order to prevent blockage of the membrane as water is passed through it.

In situations where it is desired to investigate the presence of trace chemicals in a particular sample such as a soil sample, a sediment sample or a water sample, it is usually required that the analyzed trace chemical be first extracted from the sample concentrated, and then detected using various spectroscopic techniques.

In conclusion, there are at present no available tests for rapidly conducting on-site determination of unbound ions found in a liquid or solid medium, or for determining the amount of free unbound ions in living cells. A simple and convenient test could find particularly useful applications in the area of soil nutrient testing.

SUMMARY OF THE INVENTION

In accordance with the present invention, there is provided a kit for the measurement of available ions in a liquid or solid medium. The kit comprises ion-exchange material having a measurable ion uptake potential. The ion-exchange material is in an ionic form for immobilizing available ions in the medium following contact of the material with the medium. The kit also comprises means to remove liquid or solid medium from the ion-exchange material after having contacted the medium with the ion-exchange material. The term ion-exchange material, when used in the context of the kit of the present invention is intended to include all material having anion and/or cation-exchange properties except ion-exchange resin granules or beads.

Preferably, the kit of the present invention also comprises a solution having sufficient ionic concentration to displace anions and/or cations from the ion-exchange material into the solution. It can also further comprise means for selecting a predetermined volume of a sample of the medium to be tested and, devices to mark the location of the ion-exchange material in the medium. Also, the kit can include a rigid holder for inserting the ion-exchange material in the medium to be tested. The holder is adapted to receive the ion-exchange material and maintain it in contact with the medium.

The kit of the present invention may be used for measuring free inorganic ions released from disrupted cells from a plant or animal tissue suspension. For this particular application, the kit can optionally comprise means for selecting a predetermined amount of the tissue to be tested.

More preferably, the kit of the present invention is used for the on-site in situ measurement of anion, cation or zwitterion availability in soil, water, sediments or living matter such as fruits, vegetables and fish and makes use of ion-exchange membranes pretreated to enhance immobilization of particular substances such as plant nutrients and trace chemicals.

The invention also relates to a kit for measuring free inorganic ions in disrupted cells from a plant or animal tissue suspension. The kit comprises means for selecting a predetermined amount of the tissue to be tested. The kit also comprises ion-exchange material having a measurable ion uptake potential. The ion-exchange material is in an ionic form for immobilizing free inorganic ions from the cells following contact of the material with the tissue suspension. It also comprises means to remove biological matter from the ion-exchange material after having contacted the suspension with the ion-exchange material.

The invention also relates to a method for the on-site in situ measurement of available ions (cations, anions or zwitterions) in a solid medium. The method comprises selecting a solid medium to be tested for ion availability. Ion-exchange material having a measurable ion uptake potential is then inserted in the solid medium. The moisture content of the solid medium can be optionally adjusted so as to be at a level sufficient for anions, cations or zwitterions present in the solid medium to diffuse toward the ion-exchange material. The ion-exchange material is maintained in the solid medium for a period of time sufficient for ions constituting extractable anion, cation or zwitterion sources present in the medium to be immobilized on the surface of the ion-exchange material. The ion-exchange material is then retrieved from the solid medium and solid particles are removed from it. The ion-exchange material is immersed in a solution with sufficient ionic concentration to displace the ions immobilized on the surface of the ion-exchange material from the ion-exchange material to the solution. Preferably, the method further comprises measuring the amount of ions present in the solution to determine anion, cation or zwitterion availability at the soil site. This can be accomplished using conventional analytical methods such as colorimetry or spectrometry methods which are well-known to those skilled in the art.

Also within the scope of the present invention is a method for measuring free inorganic ions in disrupted cells from a plant or animal tissue. The method comprises selecting a predetermined amount of the plant or animal tissue to be tested and providing a suspension thereof in which at least part of the cells are disrupted. Ion-exchange material having a measurable ion uptake potential is then immersed in the suspension and maintained in the suspension for a period of time sufficient for free inorganic ions from the cells to be immobilized on the surface of the ion-exchange material. The ion-exchange material is then retrieved from the suspension and biological matter is removed from its surface. Following removal of the biological matter from its surface, the ion-exchange material is immersed in a solution with sufficient ionic concentration to displace the ions immobilized on the surface of the ion-exchange material from the ion-exchange material to the solution.

Also within the scope of the present invention is ion-exchange material for immobilizing available ions in solid, liquid or sediment samples. The ion-exchange material is characterized by having a surface adapted to immobilize ions in sufficient amounts to allow an accurate determination of their concentration and availability in tire tested sample. The ion-exchange material is also characterized by being pretreated to enhance immobilization of the ions to be analyzed from the sample. The pretreatment varies depending upon the Ions to be immobilized.

Also within the scope of the present invention is an ion-exchange membrane buried underneath the surface of a sail sample or site. The membrane is characterized by being in ion-exchange relationship with available ions in the soil.

Also within the scope of the present invention is a device for measuring ion availability in a solid medium. The device comprises ion-exchange material having a measurable ion uptake potential. The ion-exchange material is in ionic form for immobilizing available ions from the medium on the ion-exchange material following in situ contact of the material with the medium. The device also comprises a rigid holder for inserting the ion-exchange material in the medium. The holder is adapted to receive the ion-exchange material and maintain the ion-exchange material in contact with the medium when the ion-exchange material is inserted in the medium.

The present invention has numerous advantages over presently existing techniques use to measure ionic availability in various samples.

The present invention involves the use of ion-exchange material in a form that is substantially different from conventional beads. In using the kit of the present invention, the ion-exchange material actually comes into direct contact with the soil sample to be analyzed which is closest to the true natural absorbing surface, namely a plant root membrane.

For example, ion-exchange resins in membrane form have teen available from different chemical suppliers under different trade means for quite some time but have received little attention by soil research labs or testing facilities. Even though the use of anion-exchange membranes (AEM) to assess available P in soil suspensions has recently been reported and AEM have also proven to be an effective means of evaluating available sulphate in soil suspensions, investigations into the possible use of AEM as a routine multi-element extractant for P, N and S have been non-existent. Similarly, there has been very little work evaluating the use of cation-exchange membranes (CEM) as routine extractants for K. One of the advantages of using the ion-exchange membrane is that since the exchange resin is in a membrane form, there is little difficulty in separating soil and exchanger.

Furthermore, the present invention provides a testing method that is quick and easy to use. Hence, as no soil samples are to be taken to the laboratory, lesser room is required in laboratory facilities and it is not necessary to dry the sample prior to testing. The extraction efficiency of buried ion-exchange membranes is high because all of the exchanging surface of the membrane is in actual contact with soil, in a manner identical to the surface of a plant root. In the case of buried bagged beads, the beads do not actually touch the soil particles but are encased in a nylon or polyester mesh so that any direct exchange of nutrient between soil particles and root surface which may be occurring in nature cannot be reproduced using this method. Furthermore, the presence of means to wash the ion-exchange material is important as it substantially eliminates the risk of contamination by bacterial growth if the ion-exchange material is removed from its burial site and maintained in a humid environment for prolonged periods of time.

Furthermore, there are important differences in medium testing conditions depending on whether testing is done in the laboratory or in the field and this further demonstrates the unobviousness of the in situ technique of the present invention.

In the laboratory, the only manner in which ions are drawn to ion-exchange material is by diffusion through the shaking of the material within the soil suspension. In the soil itself however, ions not only diffuse to the ion-exchange material through the moisture contained in the soil but also through direct contact of the soil with the ion-exchange material. Furthermore, the in situ technology gives a better idea of the actual nutrient availability in the field. Nutrient availability is greatly affected by the ability of the nutrients to move through the pores of the soil, which is a function of the soils physical structure and temperature and which can vary greatly from soil to soil. By doing in situ testing of the soil, the particular characteristics of the soil tested are taken into account. These conditions are lost in the laboratory environment since the soil suspension required does not correspond to the natural environment and the natural structure of the soil is lost in drying and grinding.

The kit of the present invention is also useful to measure nitrogen and sulfur mineralization in soil. As mentioned previously, mineralization of nitrogen and sulfur through bacterial conversion of organic matter occurs progressively during the growing season and usually comprises a significant proportion of the nutrient ion taken up by a plant over a growing season.

An accurate determination of all available nutrients throughout the growing season is important to properly dose required nutrients. The kit of the present invention allows the simultaneous determination of mineralized nitrogen and sulfur. This is obtained through burial of ion-exchange material in a closed incubation system. Ion-exchange material is used to absorb nitrate and sulfate ions released from organic matter during the incubation of field-moist soil. An index of mineralization is obtained by subtracting initial ion uptake on the ion-exchange material to ion uptake at the end of the incubation period.

The kit of the present invention can also be used to measure free ions in cells from plant or animal tissues. More specifically, the kit is useful for the measurement of inorganic nitrate and phosphate in plant leaves. The results obtained show significant relationships between the membrane extractable nitrate and phosphate in the leaf and the supply of available N and P in the soils.

IN THE DRAWINGS

DETAILED DESCRIPTION OF THE INVENTION

Figure 1:
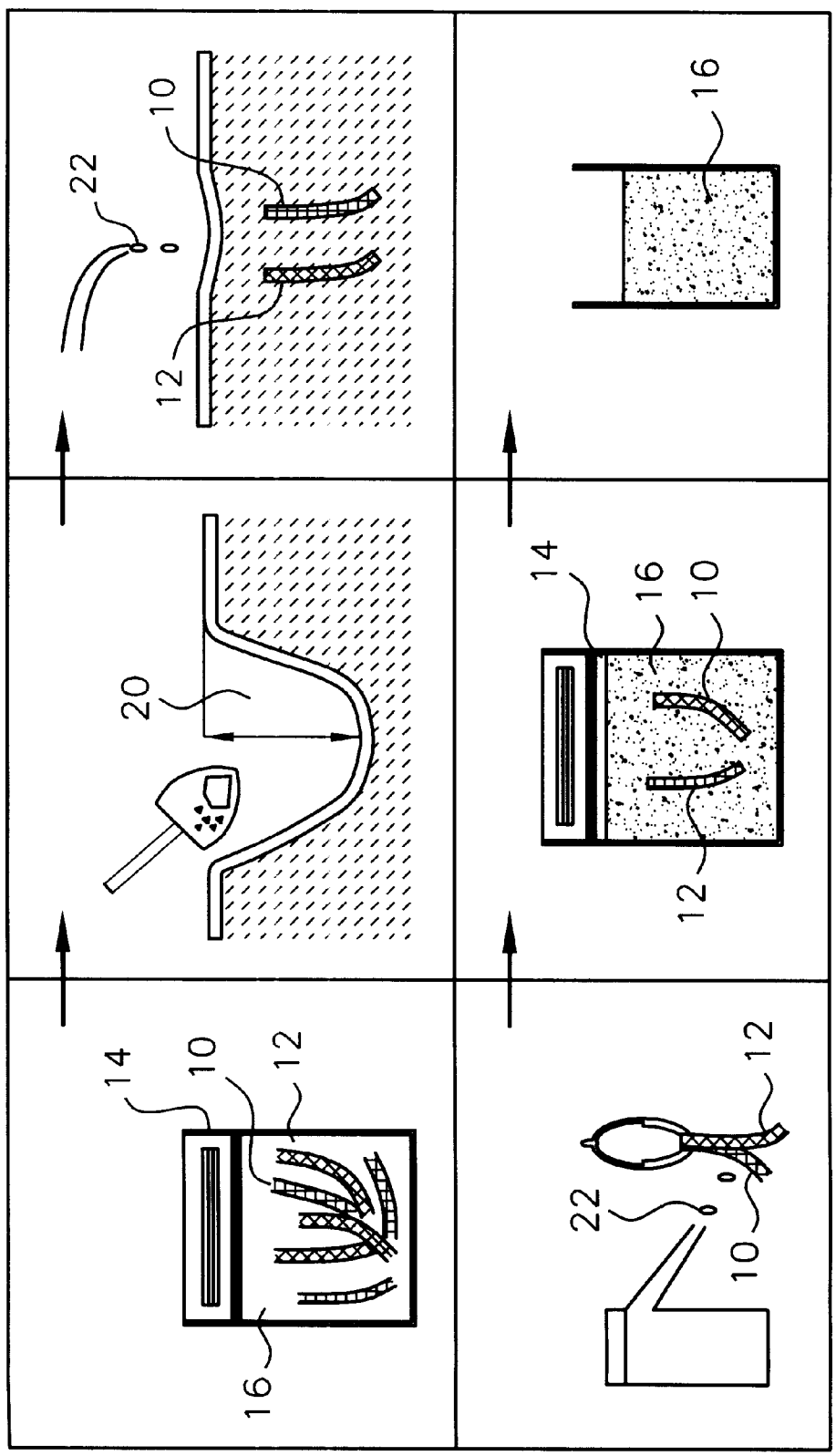
FIG. 1 is a schematic representation of the in situ extraction of ions from soil through burial of ion-exchange material in soil.
Figure 2A:
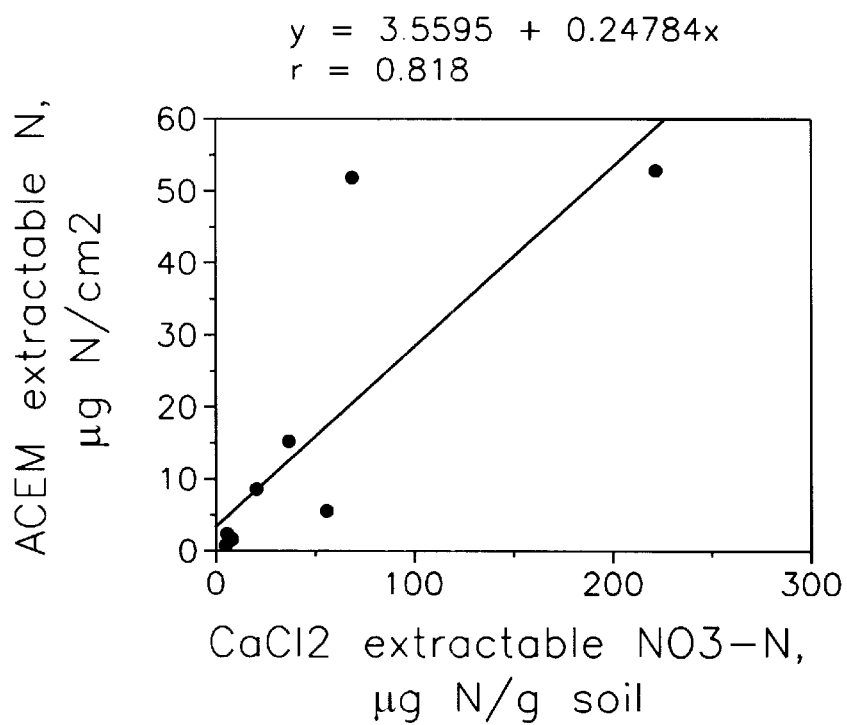
FIG. 2a represents the relationship between nitrate removed by 24 hour membrane burial and nitrate removed by conventional $CaCl_2$ extraction of soil sample in field study 1.
Figure 2B:
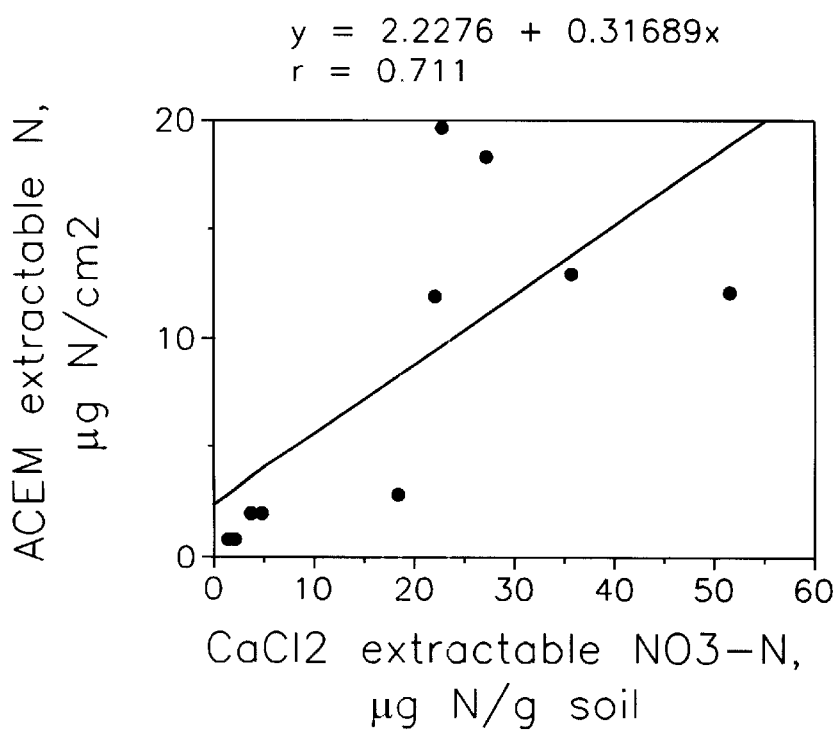
FIG. 2b represents the relationship between nitrate removed by 24 hour membrane burial and nitrate removed by conventional $CaCl_2$ extraction of soil sample in field study 2.
Figure 2C:
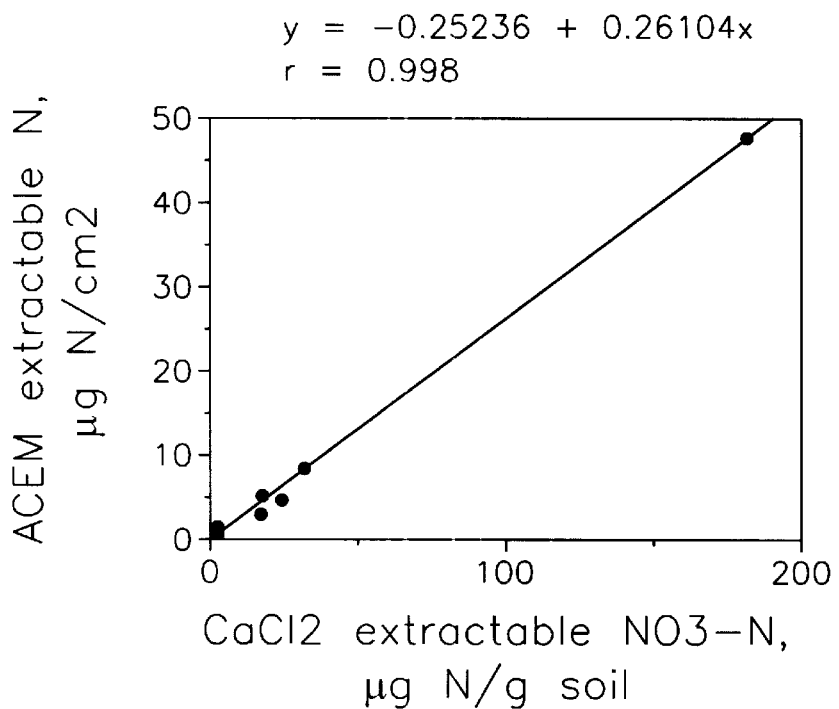
FIG. 2c represents the relationship between nitrate removed by 1 hour membrane burial and nitrate removed by conventional $CaCl_2$ extraction of soil sample in field study 3.
Figure 3A:
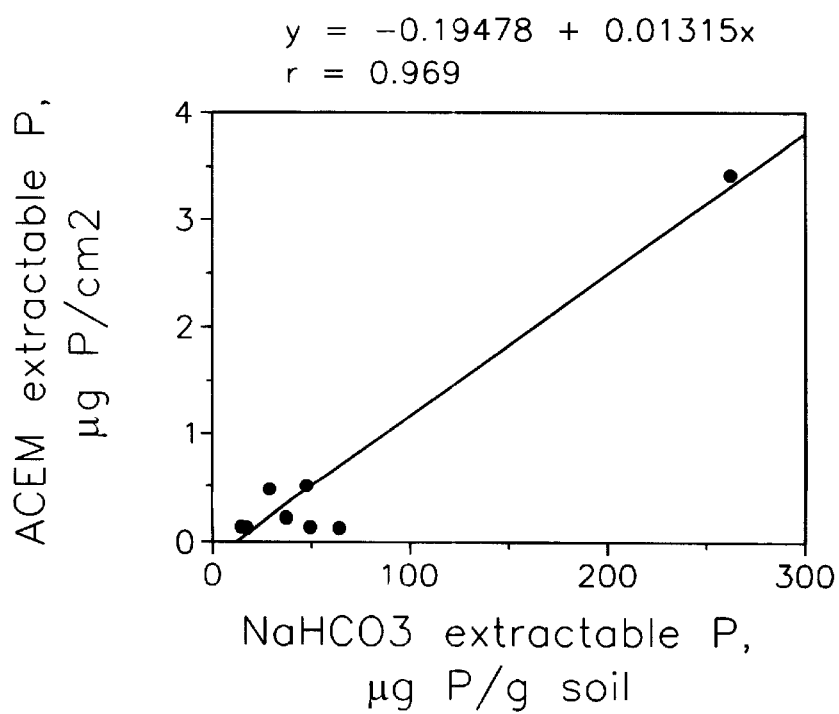
FIG. 3a represents the relationship between phosphate removed by 24 hour membrane burial and phosphate removed by conventional sodium bicarbonate extraction of soil sample in field study 1.
Figure 3B:
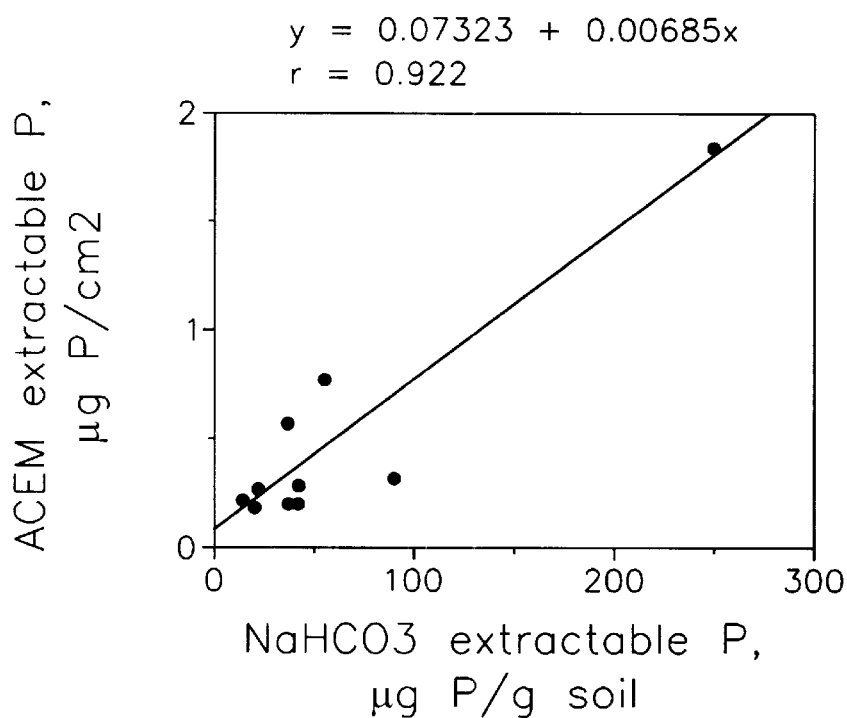
FIG. 3b represents the relationship between phosphate removed by 24 hour membrane burial and phosphate removed by conventional sodium bicarbonate extraction of soil sample in field study 2.
Figure 3C:
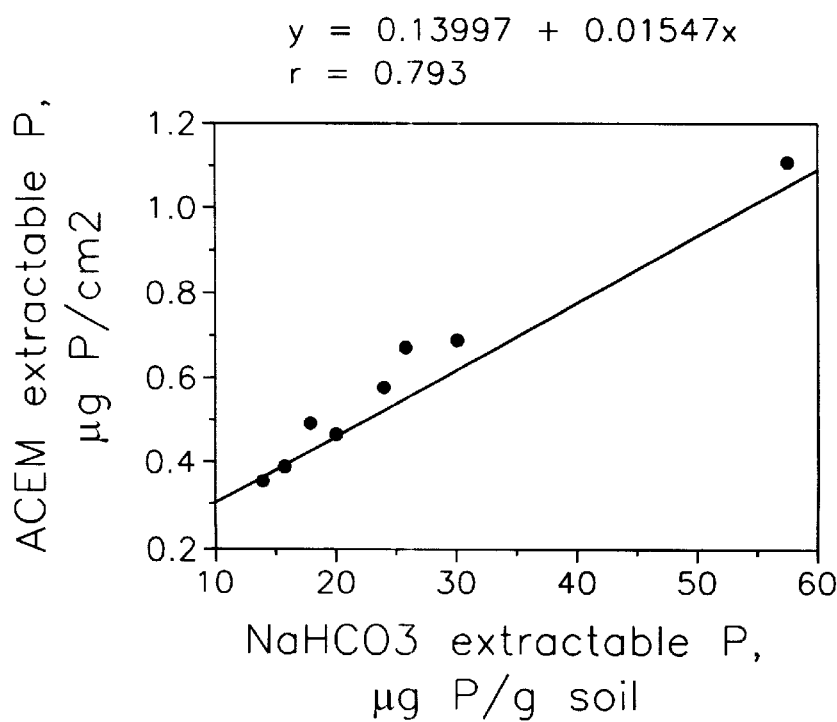
FIG. 3c represents the relationship between phosphate removed by 1 hour membrane burial and phosphate removed by conventional sodium bicarbonate extraction of soil sample in field study 3.
Figure 4A:
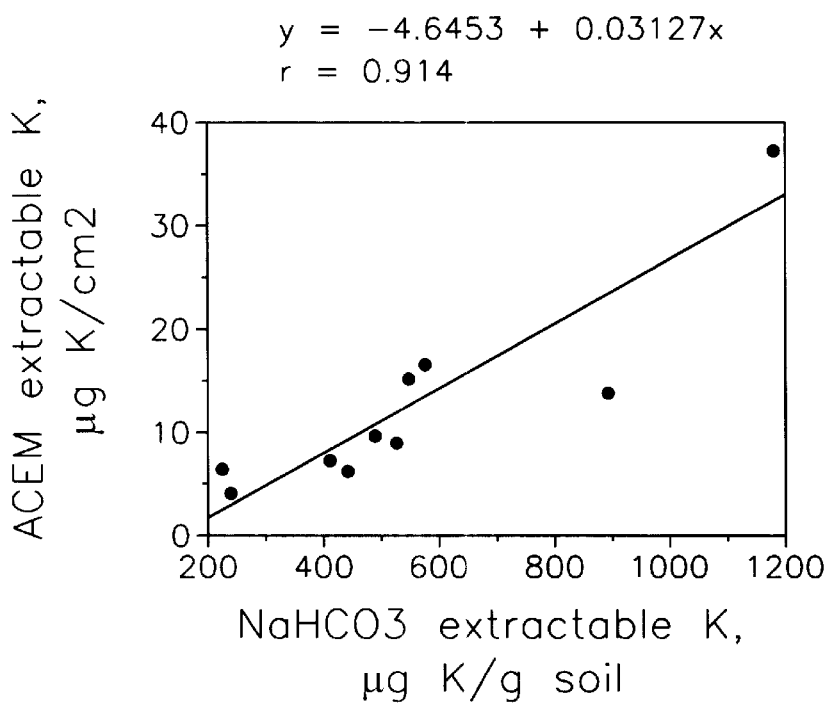
FIG. 4a represents the relationship between potassium removed by 24 hour membrane burial and potassium removed by conventional sodium bicarbonate extraction of soil sample in field study 1.
Figure 4B:
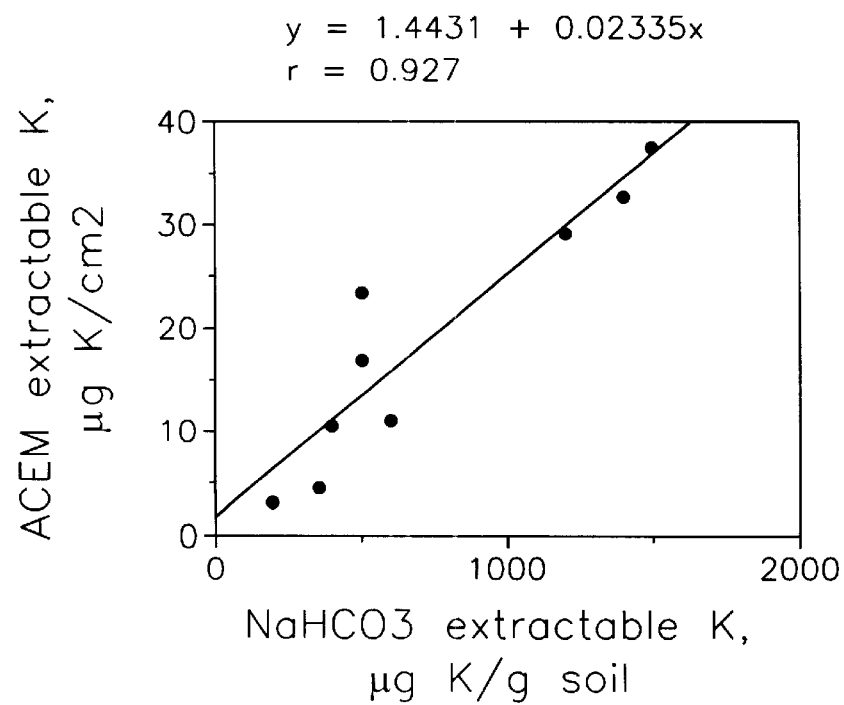
FIG. 4b represents the relationship between potassium removed by 24 hour membrane burial and potassium removed by conventional sodium bicarbonate extraction of soil sample in field study 2.
Figure 4C:
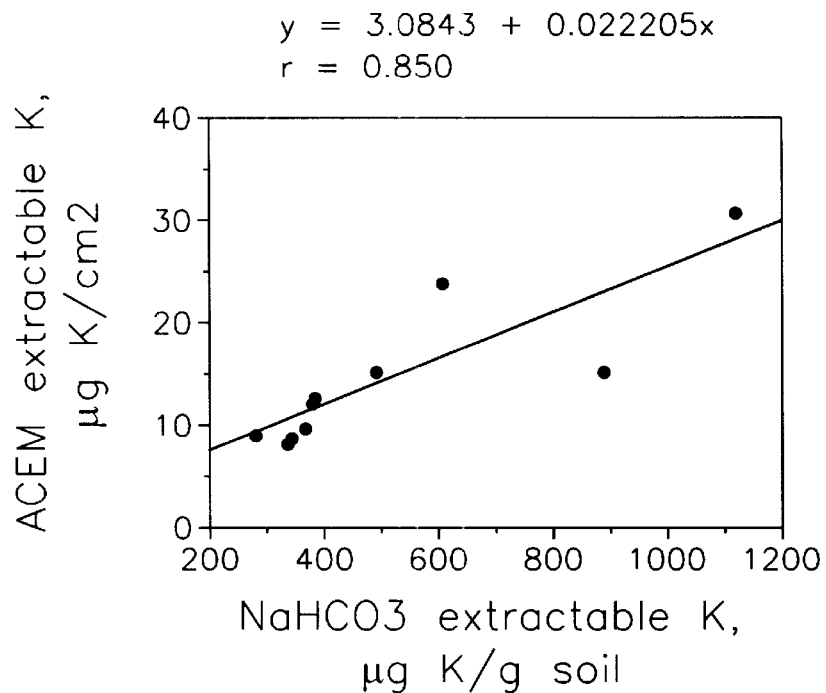
FIG. 4c represents the relationship between potassium removed by 1 hour membrane burial and potassium removed by conventional sodium bicarbonate extraction of soil sample in field study 3.
Figure 5A:
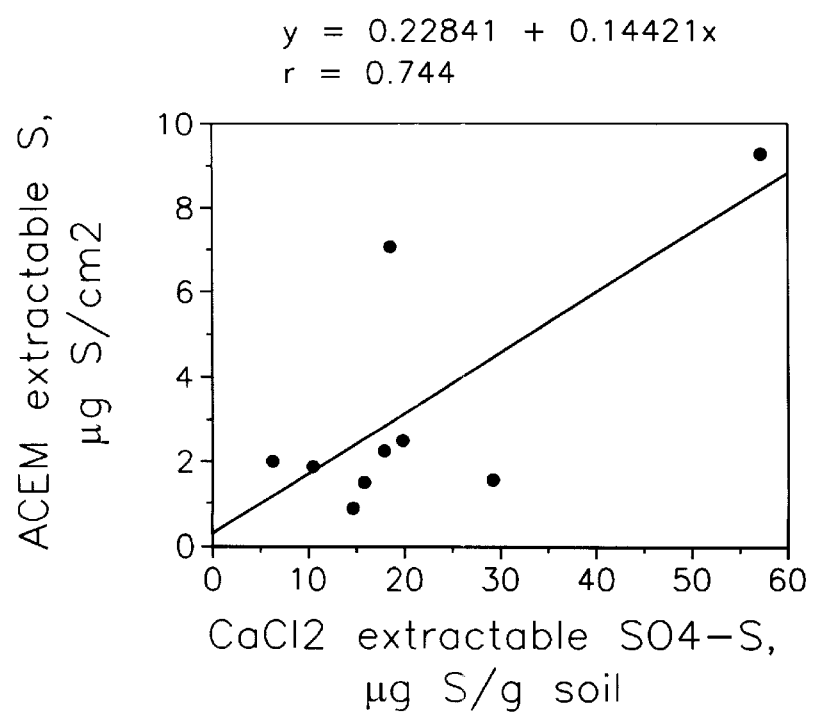
FIG. 5a represents the relationship between sulfate removed by 24 hour membrane burial and sulfate removed by conventional $CaCl_2$ extraction of soil sample in field study 1.
Figure 5B:
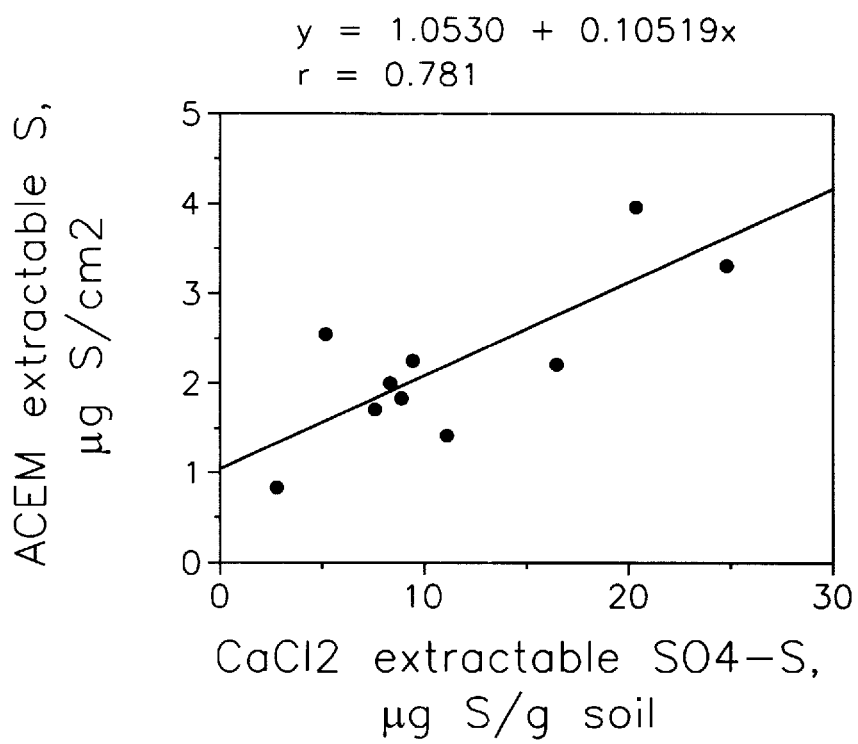
FIG. 5b represents the relationship between sulfate removed by 24 hour membrane burial and sulfate removed by conventional $CaCl_2$ extraction of soil sample in field study 2.
Figure 5C:
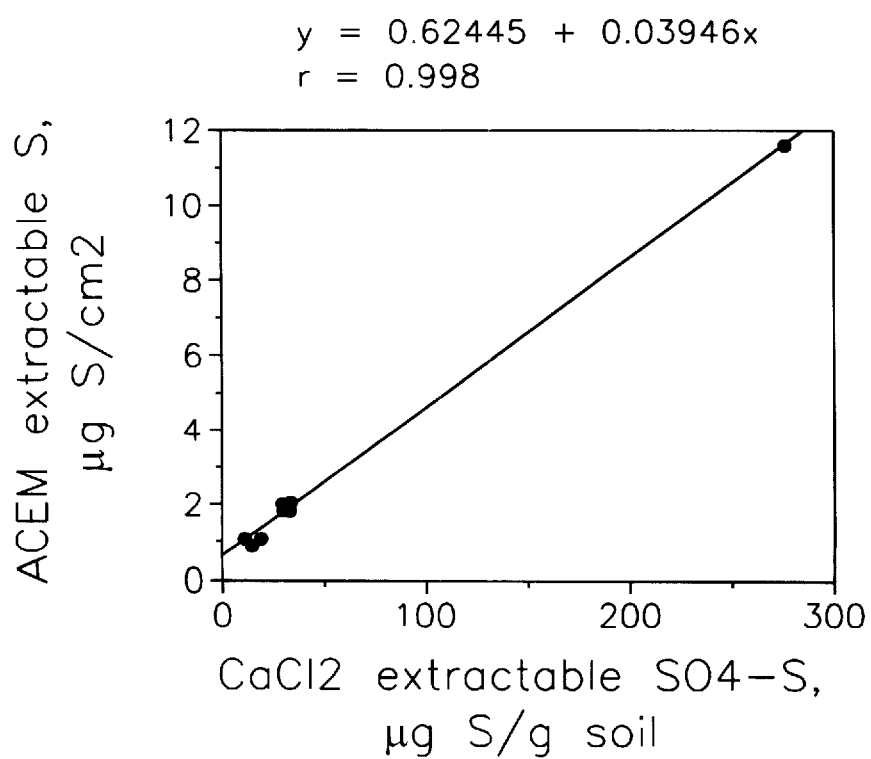
FIG. 5c represents the relationship between sulfate removed by 24 hour membrane burial and sulfate removed by conventional $CaCl_2$ extraction of soil sample in field study 3.
Figure 6A:
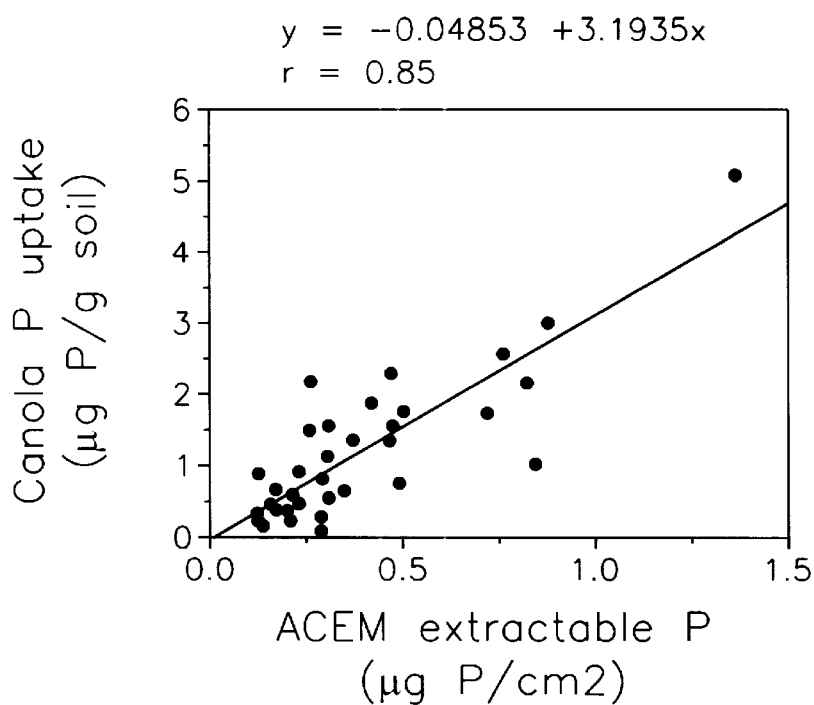
FIG. 6a represents the relationship between phosphorus uptake by canola plants grown on different soils and phosphorus availability as predicted by membrane burial.
Figure 6B:
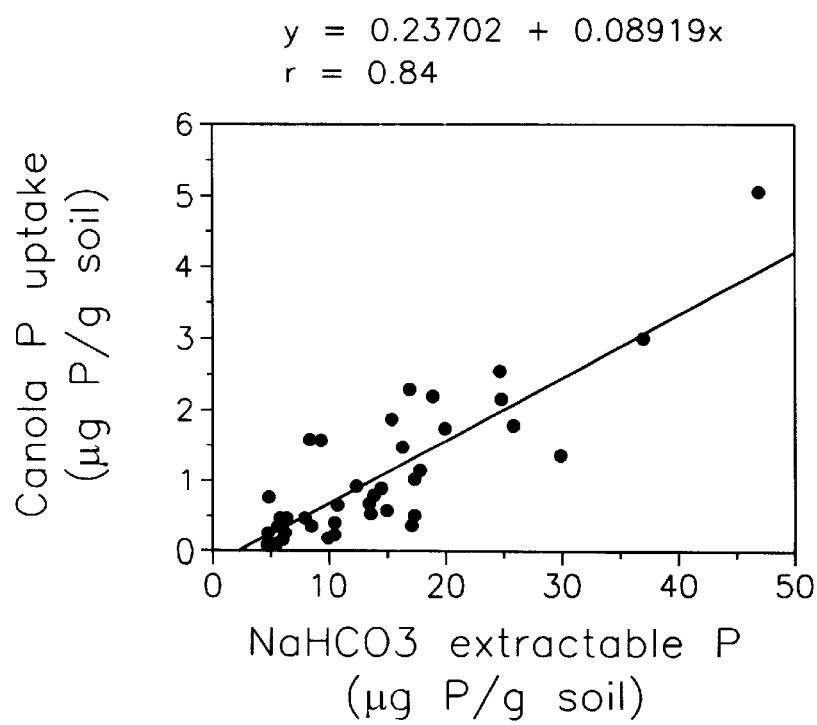
FIG. 6b represents the relationship between phosphorus uptake by canola plants grown on different soils and phosphorus availability as predicted by sodium bicarbonate extraction.
Figure 6C:
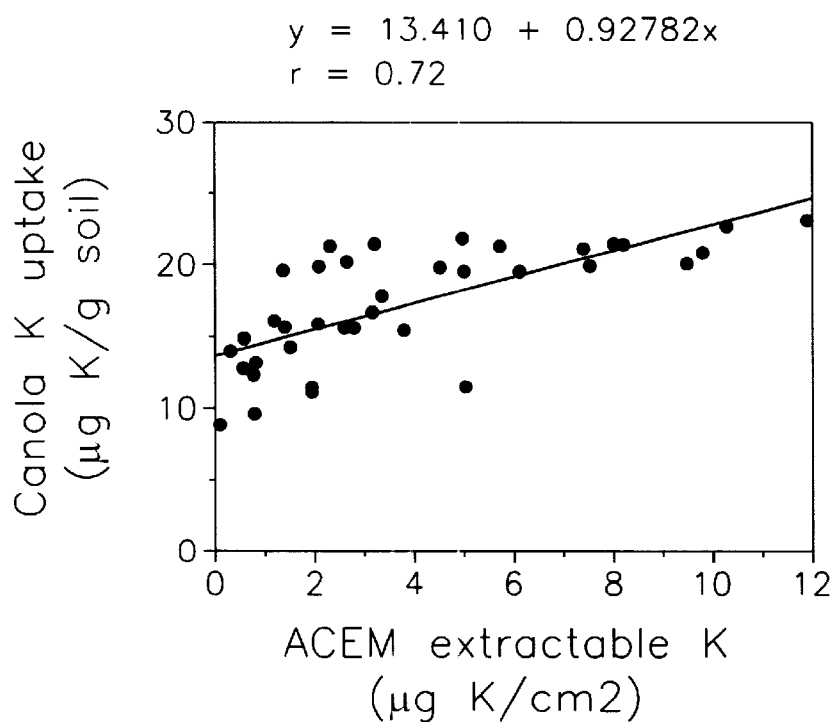
FIG. 6c represents the relationship between potassium uptake by canola plants grown on different soils and potassium availability as predicted by membrane burial.
Figure 6D:
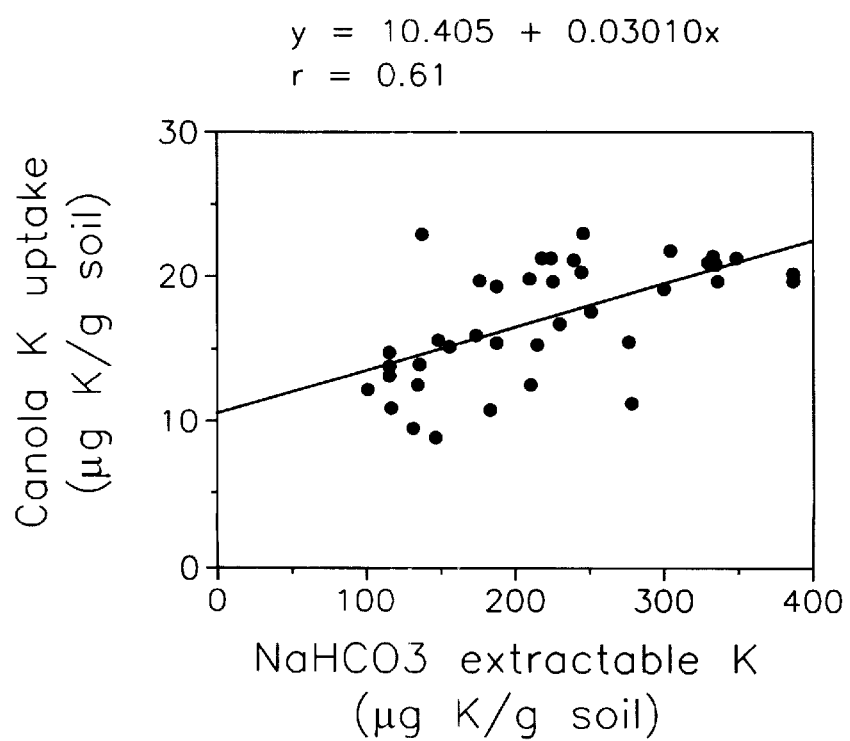
FIG. 6d represents the relationship between potassium uptake by canola plants grown on different soils and potassium availability as predicted by sodium bicarbonate extraction.

The present invention relates to techniques comprising kits, ion-exchange material and methods for the measurement of anion, cation or zwitterion availability in a liquid or solid medium. The invention can be used for various applications involving the measurement of inorganic or organic ion concentrations. The ions which are to be measured are preferably inorganic ions. However, the presence of organic ions can also be monitored although, in some circumstances, a predetermined step may be required to convert the ions into an available form. Such pretreatment step can, for example, consist in an acid, an alkali or an organic solvent pretreatment of the assayed sample.

For instance, it can be used for the on-site in situ measurement of ion availability, preferably nutrient availability, in soil, water, sediments, vegetables, fruits or animals. It can be used to measure ion concentration as a result of the application of road salt or spills. It can also be used in soil to measure leakage from potash tailings, to measure the concentration of blown salt from dry lake beds, to measure salt build-up in irrigated lands and salt contamination from water pumped-up during oil-drill or oil recovery. It is to be noted that the term "salt" when used therein is not restricted to sodium chloride but extends to other salts such as potassium salts.

The invention can also be used to monitor the concentration of ionic pollutants, either in sediments, soil or water. For instance, it can be used to monitor acid rain in lakes or to measure the amount of trace metals present in soil.

The invention is therefore useful in applications relating to environmental monitoring. For example, the burial of an ion-exchange membrane below a landfield, pesticide disposal site, etc. can be used to trap and measure any charged moieties leaching down to ground water from the site. This includes inorganic cations and anions as well as any charged organic materials which can include some pesticides and their breakdown products.

The present invention can also be used in remediation applications, for example to remove ionic contaminants from soil or water samples. The invention can also be used to extract trace elements such as copper, zinc, manganese, iron and boron from soil. Other trace elements, which are not nutrients but which are often environmental contaminants such as aluminum, arsenic, cadineum, mercury, molybdenum, nickel, selenium, lead, vanadium and chromium, can also be extracted using the method of the present invention.

One particularly interesting application of the present invention resides in the analysis of free inorganic ions in either disrupted cells from a plant or animal tissue suspension or directly in plant material or live animals. The term "disrupted cells" when used herein is intended to designate cells whose membrane has been ruptured in such a manner that their cell content has been released in their immediate surrounding environment. The examples provided further describe the use of the kit in plants material. However, it is to be appreciated that any lysed cell can be tested for free inorganic ion concentration. The use of an ion-exchange membrane in the extraction procedure for fresh plant tissue analysis is attractive because the need for filtration of the extract can be eliminated. As well, the ions are retained on the ion-exchange material such that only a strip need to be transported for analysis.

This is an important consideration if the tissue extraction is to be carried out in the field. Another important aspect to consider is the fact that it is not necessarily required to carry plant material to the laboratory. Unnecessary handling of plant material may result in moisture loss, tissue decomposition and provide inaccurate measurements. The kit of the present invention provides means for on-site measurement of free inorganic ions in plant cells.

In some instances, it is not necessary to provide a cell suspension. The ion-exchange material can be directly inserted into the plant or animal to be tested. The insertion disrupts surrounding cells, causing release of free ions which diffuse to the ion-exchange material which is then removed and eluted with the appropriate solution. For example, small strips of ion-exchange material can be inserted in a live animal with an appropriate applicator. This disrupts the cells in the immediate surroundings of the insertion point and allows a determination of free ions without killing the animal. Hence, the term "solid medium" when used herein is intended to designate not only soils and sediments but also living matter such as fruits or animals on which free ion assessment can be conducted on site using the kit and method of the present invention.

Kit

In one of its broad aspects, the present invention relates to a kit for the measurement of ion availability in a solid, liquid or suspension medium. The kit comprises ion-exchange material having a measurable ion uptake potential for immobilizing available ions from the medium following contact of the ion-exchange material with the medium. The kit also comprises means to remove particulate solids from the ion-exchange material after having contacted the media with the ion-exchange material. More particularly, mediums in which the kit of the present invention has been found to be particularly useful are heterogeneous media, which may range from waters containing particulate solids to damp soil. More specifically, examples of heterogeneous media in which the kit of the present invention is particularly useful include soil, slurries, sediments, liquids containing particulate solids and the like.

The term "ion-exchange material" when used herein is intended to include any material having cation, anion or zwitterion properties except ion-exchange resins or beads. When assessing what type of ion-exchange material is suitable for use in the kit of the present invention, one important aspect is to determine whether the ion-exchange material to be used has a measurable ion uptake potential. In other words, it should be possible to evaluate the amount of ions that can be immobilized on the ion-exchange material prior to using such material in the kit of the present invention. For instance, ion-exchange resin beads inserted in a meshed bag which is then used to immobilize ions from a soil medium are not suited for the kit of the present invention as calibration of beads is impractical and provides inaccurate results.

Therefore, it is required that the ion-exchange material used have a measurable uptake potential which is usually related to the surface area of the ion-exchange material exposed to the medium.

Preferably, the ion-exchange material used in the kit of the present invention is in the form of rigid or flexible films, sheets, membranes or the like. Flexible membranes made from sheets of polystyrene cross-linked with vinylbenzene and having attached thereto sulphonic acid or quaternary ammonium moieties such as those sold by BDH Limited are most preferred, especially for applications relating to soil testing. The flexibility of the membrane is usually not a problem for either soil, sediment or water ion measurements but if it is required to reduce flexibility of the membrane, it could, for example, be fixed in a rigid frame for insertion into the soil. In some applications, such as the measurement of contaminants in soil, it may be useful to have an ion-exchange material placed vertically into the soil at different depths in order to be able to measure differences in ion concentration as a function of depth which may become an indication of the level of contamination of a particular soil site.

The size of the ion-exchange material used in the kit of the present invention does not appear to affect the amount of ion extracted per square centimeter of surface. However, the size of the ion-exchange material chosen may be of importance for practical considerations, bearing in mind that the kit is transported into the field for use in different locations. Also, the size of the ion-exchange material might be of importance if the ions present in the medium to be analyzed are present only in very small amounts. In those circumstances, the size of the ion-exchange material may have to be increased to take this matter into consideration, that is to extract sufficient amounts of ions to be able to monitor their concentration in solution using analytical methods currently available. Hence, in the preferred embodiment where anion and/or cation-exchange membranes, which are sheet of polystyrene cross-linked with vinylbenzene and having attached thereto sulphonic acid or quaternary ammonium moieties, the preferred size ranges from 1 cm by 1 cm to 1 m by 1 m.

Removal of Particulate Solids From Ion-Exchange Material

The second element used in the kit of the present invention is means to remove particulate solids from the ion-exchange material after having contacted the medium with the ion-exchange material. This element is particularly important in order to avoid possible microbial growth resulting from prolonged storage of the ion-exchange material covered with particulate solids in damp conditions. In this regard, soil is a particularly fertile medium for bacterial growth and storing ion-exchange membranes covered with soil in humid conditions even at low temperature is likely to result in undesired microbial growth that could possibly alter the measurement of ion availability in the particular medium.

Also, for practical considerations, it would appear to be easier to remove the particulate solids immediately after removing the ion-exchange material from the medium to which it was exposed rather than conducting this operation later on because if soil is left on the ion-exchange material, it may dry and bake on it. Because of the need to remove particulate solids prior to displacing ions immobilized on the ion-exchange material, it is preferred that the ion-exchange material used have a relatively smooth surface to avoid possible entrapment of particulate solids in cavities or voids. In this regard, the use of perforated ion-exchange material is not recommended, as removal of particulate solids may cause problems.

Various devices can be used in the context of the present invention to remove particulate solids from the ion-exchange material after exposure in the medium to be analyzed for ion availability. Preferred are washing solutions of various types, the only criteria being that the washing solution must not contain ions that could be immobilized on the ion-exchange material or ions that could displace other ions already immobilized on the ion-exchange material. A preferred washing solution is simply distilled water. Other means of removal of the media include washing with a liquid spray as well as wiping, scrubbing or compressed air devices.

Additional Optional Elements of the Kit

The kit of the present invention can alternatively include further elements useful to complement or facilitate its use.

One of those additional elements is an eluent solution with sufficient ionic concentration to displace anions and/or cations immobilized on the ion-exchange material from the ion-exchange material into the eluent. The presence of this solution in the kit avoids having to take the ion-exchange material to the laboratory for elution. Another advantage of having as part or the kit an eluent solution is the fact that the eluent also acts as a medium in which the membranes can be stored once they have been remove, from the medium and washed free of particulate solids. The type of eluent solution used in the kit of the present invention may vary substantially. HCl and $NaHCO_3$ solutions have been found to he suitable eluents because of their low cost and relatively minor toxicity. HCl solutions having a concentration ranging between 0.1 and 0.5 M have been found to be particularly useful. Eluent solutions of a volume ranging from 10 to 100 ml are convenient.

One particularly useful element that can be incorporated in the kit of the present invention is a rigid holder for inserting the ion-exchange material in the medium to be evaluated without disturbing the surroundings of the medium and while maintaining the vertical position of the ion-exchange material. Preferably, the rigid holder constitutes an applicator for inserting the ion-exchange material in the medium with minimal disturbance of the medium surrounding the location at which the ion-exchange material is contacted with the medium. The applicator preferably comprises a leading edge capable of slicing the medium upon application of pressure on the holder. In this case of soil testing, the applicator can be made of pieces of relatively rigid plastic having a window in which the ion-exchange material can be immobilized. The superior portion of the applicator can protrude from the surface of the soil to be tested to facilitate its recovery. Plastic applicators or the shape used. for staking potted plants are mostly preferred. The use of plastic is particularly suitable because most plastics are inert to acidic eluents required to remove ions from the ion-exchange material but any other material which does not interfere with the ionic transfers taking place when the kit is operated can be used.

Figure 17:
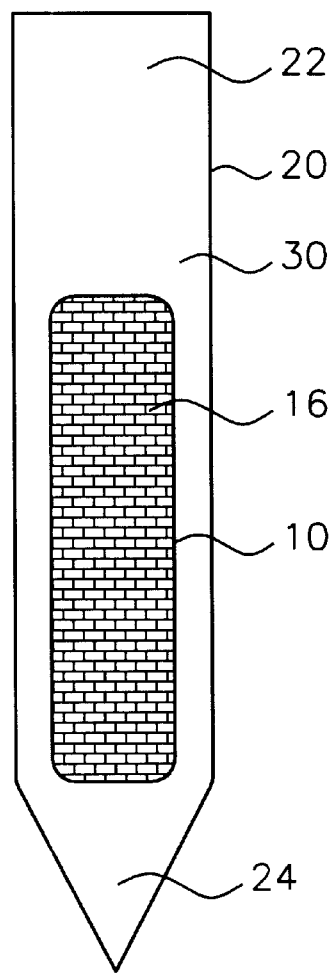
FIG. 17 is a side view of a plastic holder with ion-exchange material received thereon.
Figure 18:
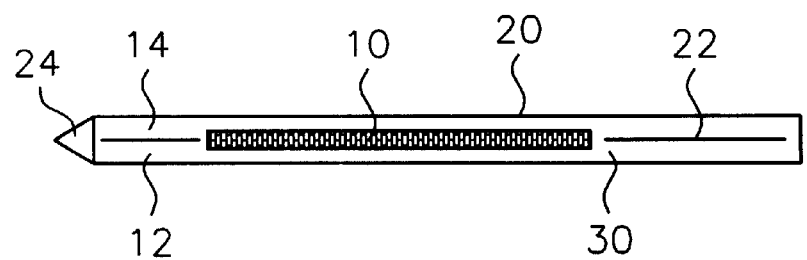
FIG. 18 is a side sectional view of the holder of FIG. 17.

A preferred embodiment of a device for measuring available ions in a solid medium, the device including a holder with an ion-exchange membrane in the appropriate position, is provided at FIGS. 17 and 18. As shown in FIG. 18, the ion exchange membrane 10 is sandwiched in holder 30, which comprises two plastic or stainless steel pointed strips 12 and 14 which are fastened together to hold the membrane in between. The device generally designated by reference numeral 20 allows the membrane 10 to be inserted into a solid or liquid media with minimal disturbance of the media. As shown in FIG. 17, the holder 30 is thin enough such that the media comes into contact with the membrane surface 10. The surface area is fixed by the sides of window 16. Debris can be readily washed away from the surface of the membrane 10 and the holder 30, and the entire device 20 placed in the eluent solution. The top 22 of the plastic holder 30 enables the device 20 to be easily retrieved following insertion and may be used to identify location, time and place of the measurement. If needed, the two plastic strips 12 and 14 can be separated to allow removal or replacement of the membrane 10 inside as needed. The pointed end 24 of the holder 30 allows for easy insertion into a variety of media.

The kit of the present invention may also comprise a recipient in which the eluent solution is contained. Preferred are flexible see-through containers with water-tight closures.

The kit of the present invention may also include means for selecting a predetermined volume of a sample of the medium to be tested. This item is particularly useful if the kit is to be used to effect ion measurements in liquid media. Any type of container that would be suitable to rapidly and efficiently retrieve accurate amounts of a sample from the media to be tested has been found to be suitable. The kit may also include a device to mark the location of the ion-exchange material after it has been inserted in the medium to be tested for ion concentration. This is particularly useful in the case of ion measurements at soil or sediment sites. The marker can, for example, be a small flag or the like.

In cases where the kit of the present invention is used for the measurement of free inorganic ions in plant or animal cell suspensions, it may be important to provide consistent quantities of the plant or animal tissue to be tested. For this purpose, a device for selecting a predetermined amount of the tissue to be tested is provided. If plant material is tested, a hole punch can be used to provide samples of uniform diameter. The device can preferably be such as to at least partially disrupt the cells on the tissue sample. It is believed that only partial disruption of the cells is sufficient as osmotic pressure created in the tissue suspension from which ion measurement is taken can cause the cells to be further disrupted.

Pretreatment of Ion-Exchange Material

Another important aspect of the present invention is the pretreatment of the ion-exchange material with a wide variety of chemicals in order to enhance immobilization of the ions to be analyzed from the medium under evaluation. Such chemicals may include, but are not restricted to, compounds that enhance the immobilization of plant nutrients from a soil or compounds that enhance complexing and immobilization of trace metals from a particular soil or water site. For example, pretreatment of the ion-exchange material with HCl and $NaHCO_3$ has been shown to enhance immobilization of plant nutrients, whereas pretreatment of the ion-exchange material with a chelating agent such as EDTA or DTPA has been shown to enhance immobilization of trace metals.

The present invention therefore also relates to an ion-exchange membrane for immobilizing available ions in samples taken from heterogeneous media. The ion-exchange membrane is characterized by having a surface area adapted to immobilize ions in sufficient amount to allow an accurate determination of their concentration and availability in the media from which they are immobilized. The membrane is also characterized by being pretreated to enhance immobilization of the ions to be analyzed from the media.

Method For On-Site In Situ Evaluation of Soil or Sediment Samples

Also within the scope of the present invention is a method for the in situ measurement of available ions (anions, cations or zwitterions) in a solid medium such as soil, sediment, fruits, vegetables or live animals. The method first comprises selecting a medium to be tested for ion availability. In the case of soil, examples of the diversity of soil types that can be tested using the method of the present invention include heavily fertilized gardens, depressional soils, pastures, wheat stubbles, sandy hills, flooded soils, fallow field, alluvial clays, road ditches, barley stubbles, rye stubbles, eroded knolls, saline soils and forest soils.

Once the medium to be tested has been selected, ion-exchange material is inserted in it. The depth at which the ion-exchange material is inserted is only important if it is critical to measure a particular ionic concentration at a particular depth. For example, as mentioned previously, in the case of analysis relating to the measurement of contaminants in soil, concentration analysis at different depths may be indicative of the level of contamination.

The method then comprises optionally adjusting the moisture content of the medium to a level sufficient for ions present in the medium to diffuse toward the ion-exchange material. The moisture content is preferably adjusted using water.

In the case of solid or sediments, water is required to provide a diffusion path for ions to reach the ion-exchange material from other parts of the soil or sediment site at which the ion-exchange material is buried if the soil is completely dry. The amount of water added is only critical from the standpoint of ensuring that the soil in the immediate vicinity of the ion-exchange material is moist. In very dry soil or sediment conditions, the addition of water is therefore required.

As soil moisture content decrease, the amount of ions absorbed by the ion-exchange material also decreases significantly. This decrease in ion removed with decreasing soil moisture content, especially at low soil moisture contents, reflects the relationship between soil moisture content and diffusive flux of nutrient ions. As the soil becomes drier, the diffusion path becomes longer and more tortuous, as the large pores are no longer filled with soil solution. This is the same limitation on diffusive flux that pant roots encounter as the soil dries out. However, moisture contents in the field are highly variable and most nutrient uptake occurs when the plant is actively growing under moist soil conditions. For this reason, the recommended method of use for the resin strip burial as a root simulator is to add water after burial to ensure that the soil in the vicinity of the strip is at or near field capacity.

The ion-exchange material is then maintained in the medium for a period of time sufficient for ions constituting extractable anion, cation or zwitterion sources present in the medium to be immobilized on the surface at the ion-exchange material. This is one aspect where the present invention has been found to be particularly useful. Burial times as short as 15 seconds can be used. What this means is that a complete round of testing can be completed in a single day and this is quite advantageous, especially when measuring nutrient availability in soil. There is no maximum time for which the ion-exchange material is to be left in the soil. It can be advantageous to leave the ion-exchange material in the soil or sediment for several weeks, up to 6 months for instance when it is desired to monitor ion movements at a particular site or to monitor the level of contamination of soil by acid rain over a long period of time. In long burial periods, mineralization and contact exchange are factors to consider when analyzing ion availability in soil. In this regard, the present invention provides flexibility never achieved before with other soil or sediment testing devices. Examples presented further provide more data on the effect of burial times.

Once the ion-exchange material has been in the medium for a sufficient period of time, it is retrieved from the soil or sediment and the particulate material found on the ion-exchange material is removed. This step is important and should, if possible, be conducted as soon as possible following removal of the ion-exchange material from the medium, for example to avoid alterations in the result through contamination resulting from the growth of bacteria present in the tested soil or sediment. The particulate material can be removed preferably simply by washing the ion-exchange material.

The ion-exchange material from which particulate material has been removed is then immersed in a solution with sufficient ionic concentration to displace the ions immobilized on the surface of the ion-exchange material from the ion-exchange material to the eluent solution. Particulars relating to this solution have been discussed previously and will be discussed in further detail later on.

The method of the present invention may include a further step through which the amount of ions present in the eluent solution is measured to determine anion, cation or zwitterion availability in the medium. The method through which the amount of ions are measured from the eluent solution can vary depending upon the ions that have been immobilized on the ion-exchange material and then displaced in the eluent solution. In fact, this may call upon most currently available analytical methods.

Use of the Present Invention in the Determination of Plant Nutrient Availability in Soil Nutrient availability to a plant is dependent on 1) the total amount of nutrient contained in a volume of soil and 2) the ability of nutrient to move to the root surface from all regions of the soil volume in response to plant demand. This ability of nutrient to move to the root surface is highly dependent on the structure and overall physical condition. The structure of a soil can vary greatly depending on climate, management, parent material, etc. When a sample of soil is removed from a field for testing, shipped and ground up prior to analysis, its structure and condition as it existed in the field is lost. Thus, conventional soil tests only take into account factor 1).

In the case of the present invention, the burial in the field of an ion-exchange material having a measurable ion uptake potential allows the test to take into account both factors 1) and 2) since soil structures remain largely intact. Soil is composed mainly of a) mineral and organic particles (solid phase) and b) voids (pores). The voids (pores) are filled with soil solution and air. The soil solution in the pores acts as a pipeline for transport of nutrients from other regions of the pores to plant root surfaces. Different soils have different shaped pores according to the way the particles are arranged in that particular soil (soil structure). The shape and size of the pores affect the ability of the ions to move to the roots of the plants and to be taken up by the plant. When the pipeline is longer, the movement is slower. Burial of ion-exchange material in the field can take into account the effect of particle arrangement and pore shape on nutrient availability as structure remains more or less intact. Although a slight soil disturbance may occur in the ion-exchange material burial process, it is predominantly the large macro-structures (large cracks) in the immediate burial zone that are disturbed. The use of an applicator can, in this regard, minimize soil disturbance to the fullest extent possible. The macro-structures are not important as channels for ion movement in soils since these channels are typically free of water under field conditions. However, when a sample is removed from the field, taken into a soil-testing lab and dried and ground-up prior to analysis, the effect that soil structure has on nutrient availability is lost.

It would appear that burying in soil ion-exchange material such as anion and/or cation-exchange membranes strongly mimics the action of plant roots. In other words, ion and/or cation-exchange membranes appear to absorb only the biologically available ions found in a manner similar to the absorption patterns of roots. This is demonstrated in some of the examples.

In the context of the present invention, the term "plant nutrients", when used herein, is intended to include macro-nutrients and micronutrients. Macronutrients can be characterized as being the elements found in soil and needed by plants in relatively high concentrations. Such elements include nitrogen, phosphorous, sulphur, potassium, calcium and magnesium. Micronutrients are characterized as being the elements found in soil and required by the plants in lesser amounts. These include iron, manganese, copper, zinc, molybdenum, boron, chlorine and cobalt. It is important to note that the division made herewith between macro and micronutrients is somewhat arbitrary but is formulated simply to provide an accurate definition of plant nutrients.

When conducting in situ analysis of nutrient availability at various soil sites, it has been found that the use of flexible anion and cation-exchange membranes that can be easily carried into the field is the most practical approach. As mentioned previously, membranes such as the sheets of polystyrene cross-linked with vinylbenzene and having attached thereto sulphonic acid or quaternary ammonium moieties sold by BDH Inc. have been found to be very useful for in situ soil testing. Preferably, those membranes can be pretreated to enhance immobilization of plant nutrients. Pretreatments with dilute HCl or $NaHCO_3$ has been found to be satisfactory for this purpose.

The dimensions (length and width) of the membrane used must be known in order to calculate its surface area so that ion concentration can be expressed as required weight per unit surface area basis.

Since the weight of ion per $cm^2$ of membrane surface is what is used as an index in soil testing, the size of the membranes used does not appear to be critical as it probably does not affect the value of the overall index. However, in soils where nutrient levels are very low, it may be necessary to use larger strips of ion-exchange membrane in order to obtain a higher total concentration in the eluent to permit better analytical accuracy in instrumental measurement. Larger strips can also be used to compensate for small amounts of ions removed in short extraction times. 60 mm×20 mm strips of anion-exchange and cation-exchange membranes have seen found to be suitable. It is important to mention that other types of anion and cation-exchange membranes could be used. The important criteria is to provide ion-exchange material having high durability and high exchange capacity. The membranes can be reused many times.

The pretreatment of the membranes can take the simple form of immersion of the membranes in the desired solution immediately prior to burial. As mentioned previously, dilute HCl has been found to be very convenient as the membranes can be carried in the field in a pouch containing dilute HCl and placed back in the same pouch of HCl for elation after burial and then pulled out again for immediate reuse if desired. The substance chosen for pretreatment of the membranes prior to burial is selected usually as a function of its low cost readily availability and lack of potential environmental problems.

The depth at which the membranes are buried for the purpose of evaluating nutrient availability is only important as it, pertains to accounting for the potential nutrient contribution of soil located at different depths. For example, In Saskatchewan, a 0–30 cm (0–12 inch) soil core is commonly used for making fertilizer recommendations since it has been shown that the nutrient level in that layer is a good index of availability, implying that most nutrient uptake comes from this layer of soil. Therefore, burial of the membrane at about a 4 inch depth would probably be optimum for most soils and crops since this represents an average of where the roots are located in the soil. However, if desired, the membranes can be buried immediately underneath the soil surface (i.e. at 1.25 cm (0.5 inch) from the soil surface) or at a depth of 61 centimeters (24 inches). If the membranes are buried deep in the soil, a core hole can be made in the soil and the membrane can be lowered down into the hole. The membranes can be attached into a string or a wire, or encased in a frame or device such as that described previously, for easy recovery.

As mentioned previously, it may in some instances be required to add water to the soil in which the membrane is buried. For example, if the soil is very dry, about 100 ml water may be added after the membrane has been buried into the soil. It is to be noted that the addition of water has not been found to be a hindrance at all to the whole process as the time required for this operation is relatively short. If water is added during the testing procedure, there does not appear to be a specific moisture content required in order for the present invention to work efficiently. If water is not added, the soil moisture content should be at or near field capacity (⅓ atmosphere suction). If water is added to very dry clay soils, one may have to add up to 250 ml of distilled water. Generally, what is required is to make sure that the buried membrane that is retrieved is retrieved from moist soil. In other words, even though it is important that the soil be sufficiently moist to permit ion diffusion toward the ion-exchange membrane buried in it, a visual determination of moisturize content is sufficient to ensure optimal moisture conditions.

Unlike any other existing soil tests, the availability index given by the membrane burial technique of the present invention does not appear to be affected by soil type. This is an important advantage of the technique of the present invention. It provides an index of relative nutrient availability regardless of soil type because its mode of action closely resembles that of a plant root, that is absorption of nutrients from the soil onto a membrane surface through ion-exchange. Conventional soil tests rely on a pH or ion (chemical) effect to remove nutrients from the soil. This is obviously not the way a plant root acts. As a result, the conventional test can provide confounding results in soils of differing chemistry.

The time during which the membrane can be buried in the soil can vary substantially depending on the intended use of the testing technique of the present invention. For a rapid evaluation of nutrient status for basing a fertilizer application, a 15 minute burial time is appropriate. This gives the user sufficient time to bury membranes in various locations in the field and subsequently remove them for elution. On the other hand, when the membranes are buried in the soil for a long period of time (i.e. 1 week), in addition to providing an index of plant nutrient immediately available to a crop, the test also provides a measure of the amount of plant nutrient that will be potentially released over the growing season from organic materials as they are slowly decomposed by microorganisms (mineralization). No other existing soil test can provide such a simple estimate of mineralization. Furthermore, no other existing soil test can provide an estimate of mineralization under the true weather conditions existing in the field. A one week or longer burial time, although not warranted every year, could be used by a farmer, for example every 5 years, to provide a general "health of the land" test. A membrane strip could even be left in a field over an entire growing season, for example up to 6 months.

Once the membranes have been maintained in the soil for the desired period of time, they are retrieved, washed from soil debris and eluted in a solution that will displace the ions immobilized on the membrane from the membrane into the solution. For this particular purpose, various acids and gases can be used at various concentrations. It has been found that HCl concentration of 0.5 M is the preferred concentration, as there does not seem to be any benefit in using an acidic solution having a higher concentration. However, lower concentrations such as 0.1 M could also be used. HCl solutions were used because neither H+ or Cl– are commonly measured on a routine basis in a soil fertility testing lab. Alternate acids such $H_2SO_4$ (sulphuric) or $HNO_3$ (nitric) could also be used but these would preclude the determination of extractable sulphate or nitrate in the soil because the sulphate and nitrate from the acids would hinder the system. As mentioned previously, the availability of various types of macro and micronutrients can be measured, although it is usually preferred to extract and measure the availability of the plant macronutrients: nitrogen, phosphate, potassium and sulphur. However, it is to be understood that simultaneous extraction of other macronutrients such as calcium and magnesium is possible. Although calcium and magnesium are not usually deficient in Canadian soils, deficiencies do exist in many tropical soils and in soils found in Southern United States.

Once the nutrients to be tested for are displaced from the membranes into the eluent solution, their concentration can be analyzed using various analytical techniques readily known by those skilled in the art.

For example, an instrument used in the context of the present invention to measure nitrate-N, ammonium-N, and phosphate is the Technicon Auto-analyzer. This is a calorimetric measurement in which degree of color development following reagent addition is proportional to concentration.

For instance, an automated procedure for the determination of nitrate and nitrite utilizes the procedure whereby nitrate is reduced to nitrite by a copper-cadmium reduction column (see Armstrong, F. A. et al., 1967, Deep-sea Res. 14, pp. 381–89 and Grasshoffk Technicon International Congress, June 1969, both references being hereby incorporated by reference). The nitrite ion then reacts with sulfanilamide under acidic conditions to form a diazo compound. This compound then couples with N-1-naphthylethylenediamine dihydrochloride to form a reddish-purple azodye. The calorimetric analysis for determining nitrate concentration can be performed with either the Technicon Auto-analyzer system or a LaChat flow injection analyzer, or similar automated colorimetry equipment.

The determination of ammonia may be based on a calorimetric method in which an emerald-green color is formed by the reaction of ammonia, sodium salicylate, sodium nitroprusside and sodium hypochloride (chlorine source) in a buffered alkaline medium at a pH of 12.8–13.0. The ammonia-salicylate complex is read at 660 nm and in the case of phosphate, the automated procedure for the determination of orthophosphate depends on the well-known chemistry whereby ammonium molybdate reacts in an acid medium to form molybdophosphoric acid which is then reduced to the molybdene and blue complex by reaction with ascorbic acid. Standards are used to construct a standard curve which is then used to determine the concentration of unknowns. All these techniques are well-known to those skilled in the art.

Potassium concentrations may be determined using automated flame-emission spectrometry using a flame-emission spectrometer and sulphate concentrations may be measured using plasma-emission spectrometry. In this method, potassium and sulfur atoms are excited to higher energy levels in a flame or plasma, thereby causing them to emit light. The intensity of light emitted is proportional to the concentration of potassium and sulfur and is measured using a spectrometer. Standards are used to construct a standard curve. The specific instrument models used in the context of the present invention were a model 3100 Perkin-Elmer AA/FE spectrometer and a model 3410+1CPARL plasma-emission spectrometer.

It is to be understood by those skilled in the art that these techniques are not the only techniques that can be used to measure ion concentrations in an eluent. The techniques described above were used because of their convenience but other alternatives are available. For instance, plasma-emission spectrometry can be used for phosphate, potassium, sulphur and all trace metals which could be plant nutrients as well as environmental contaminants including copper, iron, manganese, lead, zinc, boron, cobalt, vanadium and others. Also, capillary electrophoresis can be used to measure concentrations of anions and cations in solution. Furthermore, it is also possible to use electrochemical means to measure ion concentrations in the form of ion selective electrodes inserted into the solution.

Another means for determining ion concentration that can be used in the context of the present invention is a technique involving field calorimetric measurement. In order to be able to make calorimetric determinations directly in the field, a set of pre-packaged chemicals which, when mixed in the presence of the ions of interest, react with the ion to form a colored complex would have to be provided. The strength of color development is proportional to the concentration of ion in the solution. The chemistry is similar to that used in the automated colorimetry described previously. Colored chips can be used as standards to compare the color of the unknown and thereby determine concentration. A more sophisticated approach is to use a dipping probe calorimeter. Another potentially efficient and accurate means of measuring ion concentration in the field is to use an ion selective electrode. These electrodes can be attached to a pH meter and provide an electrochemical-based measurement of ion concentration. Ion selective electrodes are available for nitrate, potassium and other ions. This is a quickly expanding technology. As soil surveyors have long used pH meters in the field, the use of ion selective electrodes, which would be similar from a manipulative point of view, can also be foreseen.

Use of the Method of the Present Invention to Determine Ionic Concentrations in Water Samples The present invention can be used to determine ionic concentrations in water samples. More importantly, in instances where ion-exchange material was to be left for a period of time in a water sample, it can provide a measurement of release of ions from organic material contained in this sample. The method through which a membrane is used has the definite advantage of working no matter how dirty or fouled the water is. In order to provide comprehensive and accurate results in analyzing water samples, it is obviously important to use an ion-exchange material that can be easily washed of debris that can accumulate on it in a manner similar to the tests done in soil samples. Therefore, ion-exchange membranes containing very small perforations should not be used in order to avoid membrane clogging problems. In contrast, a sample of dirty water taken and run directly through a measurement instrument will give erroneous results and will sometimes damage the instrument.

The following examples are provided in order to illustrate rather than limit the scope of the present invention.

EXAMPLE 1

In-Field Soil Testing by Burial of Ion-Exchange Membranes

A series of in-field tests ware conducted in South Western Saskatchewan in the fall of 1991. Anion and cation-exchange membranes were buried in different types of soil, namely heavily fertilized garden, depressional soil, pasture soil, wheat stubble, sandy hill, flooded soil, fallow field, alluvial clay and barley stubble, rye stubble, eroded knoll, saline soil, forest soil, hay slough under the following conditions which are schematized in FIG. 1.

One strip (6 cm×2 cm) or BDH anion-exchange membrane 9 (AEM) and one strip (6 cm×2 cm) of BDH cation-exchange membrane 11 (CEM) was placed in a Ziploc plastic bag containing 30 ml of 0.5 M HCl. In the field, at each of the locations referred to previously, a hole 19 of about 12 cm deep, as shown by the arrow, was dug and a strip 9 of AEM and a strip 11 of CEM removed from the bag and placed in the hole. The holes were then refilled with soil and 125 ml of distilled water was added after burial if the soil was very dry. A flag was placed beside the hole to mark the location. After periods of time of 1 hour or 24 hours, the membranes 9 and 11 were removed from the hole and washed free of soil with distilled water 21. The membranes 9 and 11 were then placed back in the plastic bag containing the hydrochloric acid. HCl should displace the ions from the membrane surface into the solution in about 15 minutes. Therefore, after 15 minutes, the concentration of nitrate, ammonium, phosphate, potassium and sulphate in the hydrochloric acid can be measured using conventional colorimetry or spectroscopy methods such as those described previously. The concentrations determined can be used as an index of nutrient availability to make fertilizer recommendations and make field fertility maps. The membranes can then be removed from the eluent bags and are ready for reuse. Nutrient availability index results are shown in Tables 1, 2 and 3. In table 1, site 1 corresponds to a heavily fertilized garden soil, site 2 corresponds to a depressional soil, site 3 corresponds to a pasture soil, site 4 corresponds to a wheat stubble, site 5 corresponds to a sandy hill, site 6 corresponds to a flooded soil, site 7 corresponds to a fallow field, site 8 corresponds to an alluvial clay soil, and sites 9 and 10 correspond to a barley stubble.

In table 2, site 1 corresponds to a garden soil, site 2 corresponds to a pasture soil, site 3 corresponds to soil under a straw pile, site 4 corresponds to an eroded sandy soil, site 5 corresponds to a flooded soil, site 6 corresponds to a fallow field, site 7 corresponds to a poorly farmed soil, site 8a and site 8b correspond to a wheat stubble field with 8 hr and 24 hr burial times respectively, and site 9 corresponds to a forest soil.

In table 3, site 1 corresponds to a pasture soil, site 2 corresponds to a wheat stubble, site 3 corresponds to a fallow field, site 4 corresponds to a slough soil, site 5 corresponds to a saline soil, site 6 corresponds to an eroded knoll soil, site 7 corresponds to a rye field soil, site 8 corresponds to a hay slough soil, site 9 corresponds to wheat stubble, and site 10 corresponds to a road ditch. A schematic depiction of the procedure described in Example 1 is shown in FIG. 1.

All soil tests for plant nutrient status provide an index of relative nutrient availability. They tell the user which soil is high in available nutrient and which is low and are used as a basis for making fertilizer recommendations. The numeric values obtained in soil tests do not provide an absolute estimate of how much nutrient is available to a plant, rather they only act as a relative index.

Tables 1, 2 and 3 contain the data from three separate excursions into South Western Saskatchewan to measure nutrient availability using the anion and cation-exchange membrane burial technique of the present invention as well as conventional tests. The graphs in FIGS. 2, 3, 4 and 5 respectively show the relationships between predicted relative nutrient availability by the anion/cation-exchange membrane technique of the present invention and conventional tests, respectively for $NO_3$, P, K and $SO_4$ in the excursions for which data is shown in Table 1 (FIGS. 2a, 3a, 4a, 5a), Table (FIGS. 2b, 3b, 4b, 5b) and Table 3 (FIGS. 2c, 3c, 4c, 5c). The first two excursions as shown in Tables 1 and 2 used an overnight 24 hour burial time. The results of the last excursion which used a 1 hour burial time are shown in Table 3.

TABLE 1

Comparison of conventional method and the ACEM in situ (under field conditions) extractable N, P, K and S.

| | $NO_3$—N | | P | | K | | S | |
|---|---|---|---|---|---|---|---|---|
| Site | µg/g soil* Conventional | µg/cm² § ACEM | µg/g soil** Conventional | µg/cm² § ACEM | µg/g soil** Conventional | µg/cm² § ACEM | µg/g soil* Conventional | µg/cm² § ACEM |
| 1 | 225.0 | 52.5 | 265.0 | 3.43 | 1175 | 37.0 | 57.0 | 9.3 |
| 2 | 55.2 | 5.4 | 50.0 | 0.14 | 825 | 13.5 | 28.2 | 1.5 |
| 3 | 4.2 | 0.6 | 25.0 | 0.46 | 525 | 8.9 | 18.2 | 7.1 |
| 4 | 7.0 | 2.2 | 37.5 | 0.21 | 550 | 15.0 | 17.2 | 2.3 |
| 5 | 5.6 | 2.3 | 17.5 | 0.12 | 225 | 6.5 | 15.2 | 1.5 |
| 6 | 35.0 | 15.5 | 65.0 | 0.12 | 575 | 16.4 | 19.0 | 2.5 |
| 7 | 21.4 | 9.1 | 15.0 | 0.14 | 240 | 3.8 | 5.6 | 2.0 |
| 8 | 68.8 | 52.2 | 49.0 | 0.50 | 490 | 9.6 | 14.0 | 0.9 |
| 9 | 5.8 | 2.6 | 17.0 | 0.11 | 410 | 7.4 | 10.0 | 1.9 |
| 10 | 8.6 | 1.4 | 14.0 | 0.12 | 440 | 6.0 | 15.8 | 2.3 |

*conventional $CaCl_2$ extractable $NO_3$—N and $SO_4$—S.
**conventional $NaHCO_3$ extractable P and K.
§ the AEM and CEM were buried in the field for 24 hr. 125 ml (½ of cup) of distilled water added after burial as soil was very dry. Study sites were located throughout a region in S. W. Saskatchewan to provide maximum contrast in soil type and characteristics.

TABLE 2

Comparison of conventional method and the ACEM in situ (under field conditions) extractable N, P, K and S.

| | $NO_3$—N | | P | | K | | S | |
|---|---|---|---|---|---|---|---|---|
| Site | µg/g soil* Conventional | µg/cm² § ACEM | µg/g soil** Conventional | µg/cm² § ACEM | µg/g soil** Conventional | µg/cm² § ACEM | µg/g soil* Conventional | µg/cm² § ACEM |
| 1 | 36.1 | 12.8 | 250 | 1.86 | 1400 | 32.2 | 22.9 | 3.2 |
| 2 | 18.6 | 2.9 | 38 | 0.57 | 1200 | 28.8 | 16.6 | 2.3 |

TABLE 2-continued

Comparison of conventional method and the ACEM in situ (under field conditions) extractable N, P, K and S.

| | $NO_3$—N | | P | | K | | S | |
|---|---|---|---|---|---|---|---|---|
| Site | µg/g soil* Conventional | µg/cm² § ACEM | µg/g soil** Conventional | µg/cm² § ACEM | µg/g soil** Conventional | µg/cm² § ACEM | µg/g soil* Conventional | µg/cm² § ACEM |
| 3 | 22.4 | 11.9 | 90 | 0.33 | 1500 | 37.4 | 11.2 | 1.5 |
| 4 | 1.3 | 0.7 | 20 | 0.18 | 200 | 3.0 | 2.8 | 0.9 |
| 5 | 27.8 | 18.2 | 38 | 0.20 | 500 | 22.5 | 9.6 | 2.3 |
| 6 | 22.8 | 19.5 | 22 | 0.28 | 360 | 4.3 | 5.2 | 2.6 |
| 7 | 2.1 | 0.8 | 14 | 0.22 | 400 | 10.4 | 8.9 | 1.9 |
| 8a | 3.7 | 2.0 | 42 | 0.20 | 600 | 10.6 | 7.7 | 1.8 |
| 8b | 4.9 | 2.0 | 42 | 0.29 | 500 | 16.1 | 8.3 | 2.0 |
| 9 | 51.8 | 12.1 | 54 | 0.78 | 500 | 16.3 | 20.4 | 4.0 |

*conventional $CaCl_2$ extractable $NO_3$—N and $SO_4$—S.
**conventional $NaHCO_3$ extractable P and K.
§ the AEM and CEM were buried in the field for 24 hr. 125 ml (½ cup) of distilled water added after burial as soil was very dry.
8a and 8b the AEM and CEM were buried in the field for 8 hr. It indicates that can go with 8 hr. burial time.

TABLE 3

Comparison of traditional method and the ACEM in situ (under field conditions) extractable N, P, K and S.

| | $NO_3$—N | | P | | K | | S | |
|---|---|---|---|---|---|---|---|---|
| Site | µg/g soil* Conventional | µg/cm² § ACEM | µg/g soil** Conventional | µg/cm² § ACEM | µg/g soil** Conventional | µg/cm² § ACEM | µg/g soil* Conventional | µg/cm² § ACEM |
| 1 | 1.8 | 12.8 | 30 | 0.68 | 490 | 15.2 | 18.0 | 1.10 |
| 2 | 3.0 | 2.9 | 18 | 0.49 | 278 | 9.1 | 11.0 | 1.07 |
| 3 | 23.5 | 11.9 | 24 | 0.57 | 380 | 12.6 | 16.0 | 0.89 |
| 4 | 17.0 | 0.7 | 70 | 0.27 | 880 | 15.0 | 280.0 | 11.65 |
| 5 | 182.5 | 18.2 | 58 | 1.10 | 1120 | 30.1 | 5900.0 | 58.61 |
| 6 | 17.5 | 19.6 | 16 | 0.39 | 334 | 8.2 | 30.0 | 2.04 |
| 7 | 1.6 | 0.8 | 14 | 0.35 | 376 | 12.2 | 30.0 | 1.90 |
| 8 | 2.6 | 2.0 | 30 | 0.20 | 600 | 23.5 | 33.0 | 2.10 |
| 9 | 3.1 | 2.0 | 26 | 0.67 | 366 | 9.8 | 19.0 | 1.09 |
| 10 | 32.2 | 12.1 | 20 | 0.46 | 338 | 8.8 | 33.0 | 1.93 |

*$CaCl_2$ extractable $NO_3$—N and $SO_4$—S.
**$NaHCO_3$ extractable P and K.
§ the AEM and CEM were buried in the field for 1 hr. 125 ml (½ cup) of distilled water added after burial as soil was very dry. It indicates that can go with 1 hr burial time.

Regardless of burial time, the data shows good highly significant correlations between extractable N, P, K and S using the anion/cation-exchange membrane technique of the present invention and the traditional conventional soil tests which essentially comprises $CaCl_2$ extraction for N and S and $NaHCO_3$ extraction for P and K from a soil sample submitting to a soil testing lab.

Thus, when the conventional soil test indicated high nutrient availability, the anion/cation exchange membrane technique of the present invention indicated high availability. The correlation is not perfect because the anion/cation-exchange technique of the present invention seems to work better than the conventional soil tests in providing an overall index of relative nutrient availability. For example, the $NaHCO_3$ test has long been known to overestimate phosphorous availability in highly leached depressional soils. In the field work done in the context of the present invention, as expected, $NaHCO_3$ overestimated P availability in the depressions while the anion/cation-exchange membrane burial technique did not.

Also, from burial in a high organic matter pasture soil, it appears that the anion/cation-exchange burial technique takes into account the contribution of organic P mineralization to plant available P in these soils. No other simple soil tests take into account the important contribution of organic matter mineralization in the field.

The influence of burial time on the absolute amount of nutrient extracted has been evaluated. Results are shown in Table 4.

TABLE 4

Effect of burial time on ACEM in situ (under field conditions) extractable N, P, K and S.

| Site | Burial time§ Hour | $NO_3$—N | P | K | S |
|---|---|---|---|---|---|
| | | | µg/cm² | | |
| 1 | 0.5 | 1.3 | 0.46 | 14.9 | 1.28 |
| | 0.5* | 1.9 | 6.70 | 34.4 | 2.51 |
| | 1 | 0.4 | 0.46 | 12.2 | 0.71 |
| | 2 | 1.3 | 0.77 | 14.0 | 1.14 |
| | 4 | 1.0 | 0.78 | 18.8 | 1.37 |
| | 6 | 2.1 | 0.84 | 27.5 | 1.52 |
| | 17 | 2.2 | 1.17 | 29.3 | 1.83 |

TABLE 4-continued

Effect of burial time on ACEM in situ (under field conditions) extractable N, P, K and S.

| Site | Burial time§ Hour | $NO_3$—N | P | K | S |
|---|---|---|---|---|---|
|  |  | ---------μg/cm²--------- | | | |
| 2 | 4 | 9.3 | 1.58 | 45.3 | 1.98 |
| 3 | 4 | 1.5 | 1.28 | 35.0 | 1.03 |
|  | 4 | 0.6 | 1.27 | 27.9 | 2.68 |

§the AEM and CEM were buried in the field for specified time. 125 ml (½ cup) of distilled water after burial as soil was very dry.
*3 strips of AEM and 3 strips of CEM.

The results of Table 4 demonstrate that burial time affects the absolute amount of nutrient extracted by anion/cation-exchange membrane burial with somewhat lower amounts extracted over short burial times.

However, this does not affect the efficacy of the soil test as its ability to predict relative nutrient availability appears to remain the same. In field usage, it would be important to standardize some convenient time, for example 1 hour and use it consistently. In terms of effect of temperature, the temperature does not appear to have an important influence on the amount of nutrient extracted over the range of temperatures that would be encountered in the field. However, moisture content has some importance as mentioned previously in the sense that in very dry soils, the amount extracted is low. To remedy this problem, the addition of a small amount of water alleviates the problem.

Although a 1 hour is convenient for agricultural purposes, a time shorter than 1 hour is possible. The only limitation appears to be lower concentrations in the HCl eluent, which may be below detection limits for some analytical equipment. However, in practice, strips from a number of areas within a field may be placed in a single container of eluent. This would provide an elevated concentration in the eluent. The concentration will also provide an average nutrient availability index for the whole field. This is common practice now with soil samples taken from a number of areas within the field combined in a single sample sent into the lab.

Test-predicted nutrient (P and K) availability was also related to actual measured plant nutrient uptake in a wide range of western Canadian soils. Results are shown in FIG. 6. The data in FIG. 6 shows, by virtue of a higher correlation coefficient ($\tau$ value), that membrane burial is a better predictor of the P and K available to plants than the conventional tests.

EXAMPLE 2

Monitoring N and S Mineralization in Soil Samples

Sixty-seven samples or soil (0–15 cm) obtained from across Saskatschewan were selected to provide a wide range of chemical and physical properties. Of these soils, different management histories with contrasting tillage, cultivation periods, rotation and slope positions were also represented. All soils were determined for mineralized N and 44 of the samples were also measured for mineralized 5.

Among sixty-seven samples, 26 samples were selected for use in the growth chamber study of Example 3.

A 50 g sample of each air-dried soil was transferred to a 65 ml polyethylene vial. After certain amount of water (about 90% of field capacity) was added, the vial was sealed with parafilm and 5 small holes were made to allow aeration. The incubation experiment was designed as a randomized block with three replicates and conducted at 30° C. Two methods were used. One was anion exchange membrane burial technique. With this technique, a strip (2×4 mm) of an antion exchange membrane (AEM) was inserted directly into the soil before adding water, and retrieved from soil after the incubation (1 or 2 weeks) and washed free of adhering soil with deionized water and then eluted using 0.5 N HCl after incubation. The reference method used involved soil that was air-dried and ground and mixed thoroughly for 0.091 $CaCl_2$ extraction after incubation as described by Qian et al. in Commun. Sci. Plant Anal. 23: 1791–1804, hereby incorporated by reference. Nitrate in the 0.5 N HCl eluent and in the 0.001 M $CaCl_2$ extract were both determined using Technicon automated colorimetry and sulfate using ICP emission.

Results showed that $NO_3$—N and $SO_4$—S extracted over short burial times were all highly significantly correlated with N and S extracted by 0.001 M $CaCl_2$ at the start of the incubation (Table 5).

TABLE 5

NO3-N and SO4-B linear regression r2 values comparing 0.001 M CaCl2 extraction to AEX burial method tested.

| Time of AEM burial | No. of samples | NO3-N extracted | SO4-S extracted |
|---|---|---|---|
| First experiment | | | |
| 1 hour | 23 | 0.970**** | |
| 6 hours | 23 | 0.912**** | |
| Second experiment | | | |
| 1 hour | 18 | 0.998**** | 0.993**** |
| 16 hours | 18 | 0.953**** | 0.941**** |

Significant at P < 0.0001.

Relationship of Mineralized N and S as Determined By AEM Method and the Reference Method The mineralized $NO_3$—N and $SO_4$—S from the method of the present invention showed good relationship with those obtained from the reference method both in 1 week incubation experiment and in 2 week incubation experiment (Table 6). The correlations for net N mineralization between two methods were higher in 2 week incubation than in 1 week incubation but with the same level of significance.

TABLE 6

Correlations of AEM method with 0.001 M CaCl2 extraction for net N and S mineralization in two experiments

| Period of incubation | No. of samples | Mineralized NO3-N R2 | Mineralized SO4-S R2 |
|---|---|---|---|
| one week | 23 | 0.283** | |
| two weeks | 18 | 0.445** | 0.278* |

*Significant at the < 0.05 probability level
**Significant at the < 0.01 probability level

EXAMPLE 3

Use of AEM Long Term (2 Week) Burial to Predict N and S Availability to Canola

Canola plants were grown to the late flowering stage in growth chamber at 26° C. daytime and 12° C. at night. Plants were grown in 200 g styrofoam pots with 6 mg P, 40 mg K and 10 mg S per pot for —N treatment and with 20 mg N, 6 mg P and 40 mg K per pot for —S treatment. All soils were also given a blanket micronutrient treatment of Cu, Zn, Mn, Mo and B at a rate of 0.12, 0.8, 1.0, 0.12 and 0.3 mg per pot. All pots were watered twice a day to maintain the moisture level about 90% of field capacity during the experimental period.

After harvesting, all plants were oven-dried at 60° C., weighed to determine dry matter yield, ground in a stainless steel mill. Total N in the plant tissue was determined by a sulfuric acid-peroxide digestion using a temperature-controlled digestion block as described by Thomas et al. in 1967, Agron. J. 99: 240–243, hereby incorporated by reference, followed by determination of the ion concentrations in the digest using colorimetry. Total plant S was determined by sodium hypobromite oxidation as described by Tatatabai in 1982, Methods of Soil Analysis, 501–508, the contents of which is also incorporated by reference, followed by measurement of sulfate in the digest using ICP emission.

The relationship between N and S uptake by canola and the predicted availability as given by the AEM test and calcium chloride test are provided in Table 7. Both methods showed very good relationships with N and S uptake by canola. Since AEM-extractable N and S after 2 weeks were more closely correlated with plant N and S uptake ($R^2$ = 0.862** and 0.920) than the $CaCl_2$ ($r^2$=0.602 and 0.682**), AEM method, as its ability to predict N and S availability to canola, demonstrated its superiority to $CaCl_2$ extraction. The greater accuracy of AEM is because it can mimic plant root action. AEM could continuously absorb the released nutrients from soil organic matter over the 2 week incubation.

TABLE 7

Coefficient of determination for relationship between total uptake of N and S (y) by canola and individual measurement of NO3-N and SO4-S in soil$

| Nutrient extracted | Coefficient of determination ($r^2$) | |
|---|---|---|
| | N-uptake (n = 23) | S-uptake (n = 28) |
| 1 hour AEM burial | 0.688 | 0.712**** |
| 2 week AEM burial | 0.862 | 0.920**** |
| net N or S mineralization from AEM burial | 0.837 | 0.904**** |
| Residual nitrate or sulfate | 0.586 | 0.477*** |
| 2 week incubation from CaCl2 extraction | 0.602 | 0.682**** |

$Some of net N and S mineralization from CaCl2 extraction or any other method were negative values and the net N and S mineralization was not made correlation with canola uptake.
****P < 0.0001.
***P < 0.001

EXAMPLE 4

Study of the Influence of Various Parameters on AEM Performances in Soil Nutrient Testing Sheets of anion and cation exchange membrane (BDH product no. 55164, 55165) were cut into 20×65 mm strips. The resin strips were then washed in 0.5 M $NaHCO_3$ or 0.5 M HCl and stored in deionized water prior to use. Then one anion exchange and one cation exchange resin strip was inserted directly into approximately 200 g of soil. After burial, deionized water was added to the surface of the soil to ensure that the soil in the vicinity of the strip was at or near field capacity. After the burial period, the strips were removed, washed free of adhering soil with a few squirts of deionized water, and then placed into a flask containing 20 mL of 0.5 M HCl to elute (displace) the ions from the resin. All nutrient ions absorbed from the soil by the strips are displaced into solution by the dilute HCl. After 15 minutes, the strips were removed and nutrient concentration in the HCl eluent determined using Technicon automated colorimetry for nitrate and phosphate, a flame emission spectrometer for potassium, and ICP emission for sulphate. The resin strips are made ready for re-use by washing in 0.5 M $NaHCO_3$ or 0.5 M HCl. The same strips have been used for hundreds of short term extractions with no apparent physical deterioration or loss of effectiveness. A technique similar to that described above was used for burial directly in the field. Nutrient removal is expressed as micrograms of nutrient per square centimeter of strip surface.

Effect of Burial Time on Amount of Nutrient Extracted

Comparison between 24 hour and 1 hour resin strip burial for 5 selected soils showed lower amounts of nutrient removed in the 1 hour burial period (Table 8). This trend was particularly pronounced for N and S, while P and K were less affected. The greater effect of short versus long period burial times on nitrate and sulphate removal may be explained in part by the additional contributions to nitrate and sulphate from organic matter mineralization over longer burial times such as 24 hours. As well, contact exchange is likely a more significant removal process for P and K as compared to nitrate and sulphate where diffusion is of greater relative importance. The diffusion would be affected more by burial time than the contact exchange. Differences observed between the soils may be explained on the basis of differences in mineralization potential as well as differences in soil texture, structure and density which would affect the relative impact of diffusion and contact exchange.

TABLE 8

Nutrient removal by resin strips buried for 24 hr and 1 hr in five Saskatchewan soils.

| | Nitrate | | Phosphate | | Potassium | | Sulphate | |
|---|---|---|---|---|---|---|---|---|
| | ------------------------------$\mu g/cm^2$------------------------------ | | | | | | | |
| Soil | 24 hr | 1 hr | 24 hr | 1 hr | 24 hr | 1 hr | 24 hr | 1 hr |
| 1 | 142.9 | 20.9 | 1.60 | 0.66 | 72.0 | 35.5 | 15.5 | 3.6 |
| 2 | 84.1 | 4.7 | 0.23 | 0.07 | 28.3 | 17.6 | 106.6 | 10.1 |
| 3 | 167.9 | 28.7 | 0.40 | 0.23 | 12.7 | 18.1 | 15.4 | 3.9 |

TABLE 8-continued

Nutrient removal by resin strips buried for 24 hr and 1 hr in five Saskatchewan soils.

| | Nitrate | | Phosphate | | Potassium | | Sulphate | |
|---|---|---|---|---|---|---|---|---|
| | $\mu g/cm^2$ | | | | | | | |
| Soil | 24 hr | 1 hr | 24 hr | 1 hr | 24 hr | 1 hr | 24 hr | 1 hr |
| 4 | 21.6 | 5.9 | 0.25 | 0.14 | 30.6 | 20.9 | 5.4 | 2.3 |
| 5 | 28.9 | 8.6 | 1.21 | 0.30 | 17.5 | 27.5 | 8.3 | 2.5 |

Values are means of three replicate analyses

Comparison of 15 minute and 1 hour burial times revealed a lower amount of nutrient extracted over 15 minutes, although the amount removed over 15 minutes still exceeded 70 percent of that removed over 1 hour. Burial times shorter than 15 minutes using a single strip of the size indicated above, along with the above indicated eluent volume resulted in phosphate concentrations in the eluent that were approaching the detection limit of the autoanalyzer equipment. This may be overcome by using larger strips, or else through burial of two or more strips which are then placed into the same eluent. If two or more strips are buried, this gives the additional advantage that the concentration of nutrient expressed per unit area of strip surface represents an average of the amounts removed by the two strips, similar to a bulked soil sample.

Figure 8:
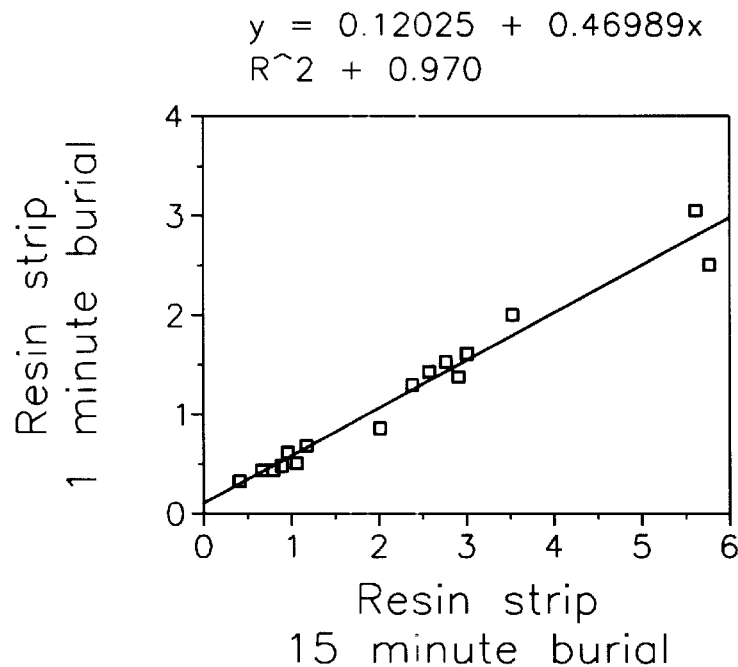
FIG. 8 represents the relationship between nitrate removed by ion-exchange buried in soil for 15 minutes and 1 minute.

Nitrate removed by resin strip burial for times shorter than 15 minutes were compared for four Gray Luvisolic soils. In this case, two strips were buried in 120 g samples of the 4 soils for 1, 5, 10 and 15 minutes. The shorter burial times resulted in lower removal of nitrate N from the soil. However, even for only a 1 minute burial the amounts of nitrate removed were well within the detection limits of our autoanalyzer. For another 16 soils in a comparison of 1 minute and 15 minute burials (FIG. 8), the amounts of nitrate removed in 1 minute were strongly correlated with nitrate removed over 15 minutes ($r^2=0.97$).

Effect of Temperature

The amount of N, P, K and S removed by buried resin strips was evaluated at four temperatures: 30, 20, 10 and 4° C. The overall trend was found to be a slight decrease in the amount of nutrient extracted as soil temperature decreased, although in many cases the decreases were not significant. In most instances, 10° C. temperature differences did not have a significant effect on amount extracted (p=0.05), especially between 20° C. and 10° C. This effect was mainly observed for N and S over short (15 minutes) burial times. The trend towards decreasing amounts removed with decreasing temperature likely reflects the direct effect that temperature has on ion diffusion, as well as an additional effect of increasing viscosity of water near and at temperatures of 4° C. This may not be viewed as a limitation since plant roots absorbing nutrient ions from soil in the field under similar temperature conditions would experience the same effect on nutrient diffusion to the root.

Effect of Moisture

The amount of nitrate, phosphate, potassium and sulphate removed from the four soils at five soil moisture contents (saturated, field capacity, and 70, 45 and 15% of field capacity) was evaluated. In all cases, a similar trend was observed. As soil moisture content decreased, the amount of ion absorbed by the resin strips decreased significantly. Data are presented for two of the soils in Table 9 where the largest changes were associated with changes in moisture contents below about 70% of field capacity.

TABLE 9

Nutrient ion removed by 1 hour resin strip burial in two soils at five soil moisture contents.

| | Soil 1 | | | | Soil 2 | | | |
|---|---|---|---|---|---|---|---|---|
| | N | P | K | S | N | P | K | S |
| Moisture | $\mu g/cm^2$ | | | | | | | |
| Saturated | 17.5 | 0.41 | 47.9 | 69.5 | 28.2 | 0.45 | 21.8 | 5.0 |
| 100% F.C. | 10.9 | 0.33 | 39.1 | 50.8 | 20.0 | 0.27 | 18.1 | 3.9 |
| 70% F.C. | 7.4 | 0.20 | 28.2 | 30.8 | 19.6 | 0.14 | 15.5 | 3.7 |
| 45% F.C. | 4.2 | 0.13 | 20.2 | 16.7 | 11.3 | 0.09 | 9.3 | 2.6 |
| 15% F.C. | 0.7 | 0.04 | 10.0 | 1.9 | 2.4 | 0.03 | 4.8 | 1.2 |

Values are means of three replicate analyses.

EXAMPLE 5

Relationship Between Nutrients Extracted By Burial of Ion-Exchange Material and By Chemical Extractants Chemical Extraction In the determination of $NaHCO_3$ extractable P and K, a 3 $cm^3$ scoop of soil was shaken with 60 mL of 0.5 M NaHCO for 30 minutes on a reciprocating shaker. The suspension was filtered, and the phosphate in the extract determined by automated colorimetry and K determined by flame emission analysis. Another chemical extraction for P and K, known as the modified Kelowna method, which is described by Qian et al. in 1991, Comparison of several extractants for available phosphorus and potassium in Soils and Crop Workshop, Univ. of Sask., Saskatoon, Saskatchewan, hereby incorporated by reference, was performed. The modified Kelowna extracting solution is comprised of 0.25 N HOAc and 0.15 N $NH_4F$ as well as 0.25 N $NH_4OAc$. Soluble $NO_3$—N and $SO_4$—S were determined by shaking a 25 $cm^3$ scoop of soil with 50 mL of 0.001 M $CaCl_2$ for 30 minutes. Samples were then filtered and the nitrate and sulphate concentrations determined calorimetrically.

In over 200 soil samples, resin strips were buried for 1 hour and the amounts of N, P, K and S extracted were compared to conventional chemical extractants (Table 10). For all nutrients, the amounts removed by the resin strip burial were significantly correlated with the conventional chemical extractants (p=0.0001).

TABLE 10

Coefficients of determination ($r^2$) for regressions between nutrient extracted by resin strip burial (1 hour) and chemical extractants.

| Nutrient | No. of samples | $r^2$ |
|---|---|---|
| N | 255 | 0.69*** |
| P | 244 | 0.57*** |
| K | 205 | 0.33*** |
| S | 232 | 0.73*** |

***Significant at P = 0.0001

Figure 9A:
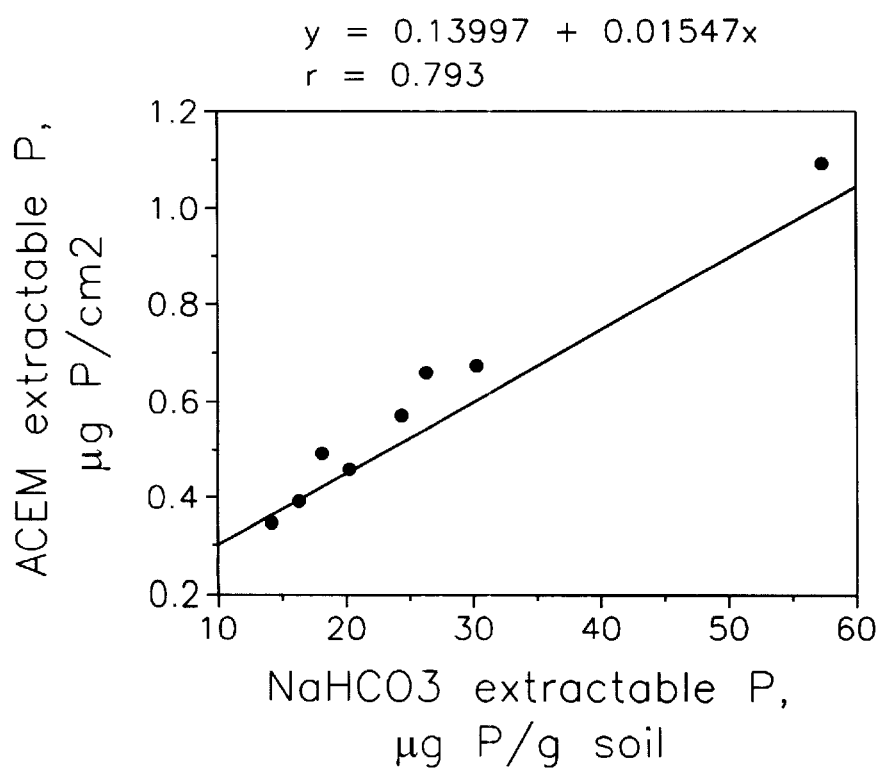
FIG. 9a represents the relationship between phosphorus removed by 1 hour in situ field burial of membranes and phosphorus removed by sodium bicarbonate extraction in the lab.
Figure 9B:
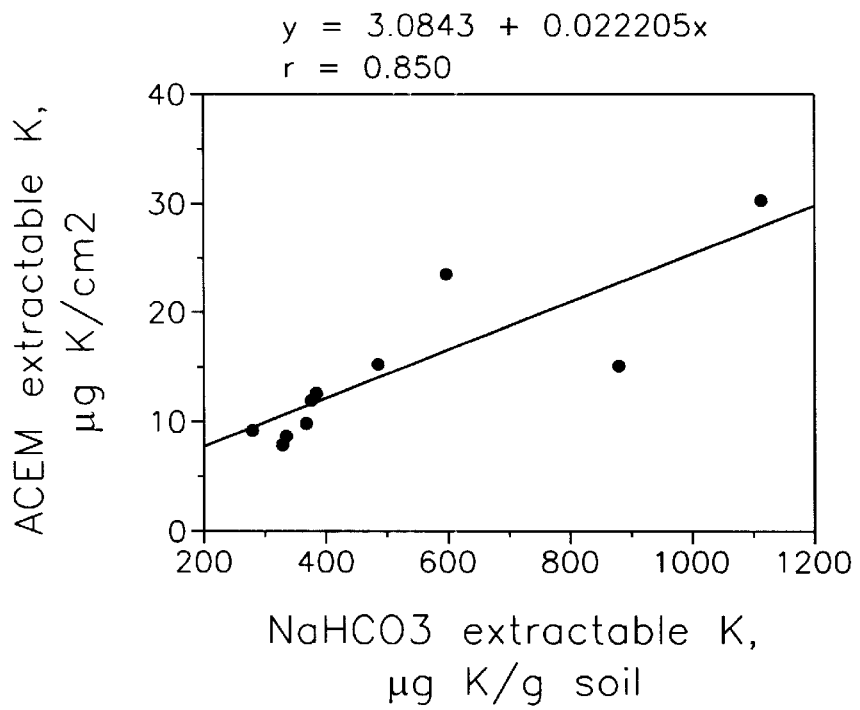
FIG. 9b represents the relationship between potassium removed by 1 hour in situ field burial of membranes and potassium removed by sodium bicarbonate extraction in the lab.

In a small field study in southwestern Saskatchewan, resin strips were buried directly in the field for 1 hour in 10 different soils with contrasting slope position, management, and cropping history. The amounts removed were compared to conventional extractions conducted on a sample of soil taken from beside each burial site and analyzed in the laboratory. For N, P, K and S, the amounts removed by the two methods were strongly and significantly correlated. The relationships for P and K are shown in FIG. 9.

EXAMPLE 6

Growth Chamber Study

Growth chamber experiments were conducted using canola as the test crop for which actual plant uptake was measured and related to availability as predicted by the resin strips and chemical extractions. One of the growth chamber studies used 39 soils selected from the 200 soil samples on hand and a 24 hour strip burial time, and the other used 65 selected soils and a 1 hour burial time. In each pot, three canola plants (var. Profit) were grown to the late flowering stage, harvested, and the tissue dried for analysis. Total N, P and K in the plant tissue was determined by a sulfuric acid-peroxide digestion at 360 degrees followed by determination of the ion concentrations in the digest. Total S in the plant tissue was determined by sodium hypobromite oxidation (260° C.) to sulphate as per the method of Tabatabai and Bremner in 1970 Soil Sci. Sco. Am. J. 54: 1666–1669 hereby incorporated by reference, followed by determination of the sulphate in the digest using inductively coupled plasma emission spectrometry.

Two separate growth chamber experiments were conducted, one using 65 soils and a 1 hour strip burial period, and the other using 39 soils and a 24 hour strip burial period. For the 1 hour burial experiment, the Kelowna extracting solution was used as the chemical extractant for P and K. In the 24 hour burial experiment, the sodium bicarbonate (Olsen) extraction was used for P and K. In the two growth chamber experiments, both the resin strip burial and the conventional chemical extractions were highly and significantly correlated with actual measured plant uptake of the nutrients (Table 11).

TABLE 11

Coefficients of determination for relationships between soil nutrient extraction and nutrient uptake by canola.

| | | $r^2$ | |
|---|---|---|---|
| Nutrient | Extraction | Experiment 1 (1 hr, n = 65) | Experiment 2 (24 hr, n = 39) |
| Nitrogen | Resin Strip | 0.55*** | 0.62*** |
| | $CaCl_2$ | 0.60*** | 0.57*** |
| Phosphorus | Resin Strip | 0.71*** | 0.72*** |
| | $NaHCO_3$ | — | 0.70*** |
| | Kelowna | 0.76*** | — |
| Potassium | Resin Strip | 0.46*** | 0.52*** |
| | $NaHCO_3$ | — | 0.37*** |
| | Kelowna | 0.40*** | — |
| Sulfur | Resin Strip | 0.80*** | 0.96*** |
| | $CaCl_2$ | 0.75*** | 0.61*** |

Significant at p = 0.0001.

Both the resin strip burial and chemical extraction were good predictors of plant nutrient uptake patterns among the soils. There appears to be little difference in the ability of the resin and the conventional chemical extractions to predict nitrogen and phosphorus availability to canola grown on the soil samples tested. However, the resin strip burial may offer somewhat better predictive ability for S and K availability. In the case of predicting K availability, the resin may be able to distinguish between K ions held onto soil colloids with differing degrees of affinity and therefore plant availability. Since ground and dried soil samples were used for the resin strip burials, any effects that soil structure has on nutrient availability to plants growing in the field is not accounted for in either of these tests. This would be expected to be most important for nutrients like potassium and phosphorus, where soil structure as it affects the nature of the pores and the diffusion path will greatly affect the ability of the nutrient to move to the root. Direct in field burial of resin strips may have an advantage in being able to account for this.

EXAMPLE 7

Use of anion exchange nembrane (AEM) extraction procedure to assess N and P availability in sunola (Helianthus) and spring wheat (Triticum).

Growth Chamber Experiment

A growth chamber experiment was conducted using a Luvisol soil (Walteville sandy loam) of low $NO_3$—N and phosphate status (Table 12).

Plastic pots were filled with 1200 g of air dry soil. For the nitrogen treatment, nitrogen was applied at the rate of 0, 50, 100, 150 and 200 mg N/kg soil. For the phosphate treatment, phosphorus was applied at the rate of 0, 40, 80, 120 and 160 mg P/kg soil. To each pot a minus N (for the nitrogen treatment) or a minus P (for the phosphorus treatment) nutrient solution was added plus an additional 10 mL of a basal micronutrient solution, to ensure that availability of other nutrients did not restrict growth. Approximately 12 seeds of sunola (Helianthus) were sown into each pot. After germination, the pots were thinned to 3 sunola plants per pot. The pots were transferred to a growth chamber with 16 hour day length, kept at 25° C. during the day and 12° C. at night. The soil moisture was maintained at 90% of field capacity by daily watering with deionized water. The pots were completely randomized and re-positioned every week to minimize any effects of uneven environmental factors such as light and temperature.

TABLE 12

Properties of the soils used in the experiments.

| Soil | pH | Conductivity mS-cm$^{-1}$ | Organic C % | $NO_3$—N | P | K | $SO_4$—S |
|---|---|---|---|---|---|---|---|
| | | | | ------------μg/g soil------------ | | | |
| Waiteville sandy loam¶ | 7.2 | 0.1 | 2.3 | 4.4 | 15.0 | 276 | 8.9 |
| Sutherland clay¶¶ | 7.9 | 0.6 | n.d. | 23.0 | 34.0 | 680 | 16.0 |

¶Soil used in the growth chamber experiment
¶¶Soil used in the field experiment
n.d. denotes not determined.

The youngest fully expanded to second leaves were samples at sixth leaf stage (20 days after seeding) from each plant on each pot. The plants were harvested at AS days after seeding. The tops and heads of the plants were removed and the roots separated from the soil by sieving and washing. The plant materials were then dried at 60° C. and weighed, Field Experiment Field plots were located at the Kernen Farm, Saskatoon, Saskatchewan. Properties of the Sutherland clay soil at the site are presented in Table 12.

The experiment was a split-plot design, with six main plot treatments and five sub-plot treatments, five varieties of spring what and three replications. The five varieties were AC Taber, AC Reed, BW 90, Katepwa and Roblin. Nitrogen fertilizer was applied as broadcast ammonium nitrate at 0, 40, 80, 120, 160 and 240 kg N/ha to provide the six main plot treatments for each Variety and each replicate. An additional 20 kg P/ha was broadcast on each plot. Each sub-plot was 9.75 m×6.10 m (42'×20'), with a total area of 18.3 m×65.5 m (60'×215') for three blocks. Plants were seeded at 80 g seed/sub-plot on May 6, 1992 and harvested at mature stage on Sep. 11, 1992.

Forty to fifty plants were sampled from each sub-plot at the tillering stage. The samples were collected in plastic bags. Tissue samples were taken using a hole punch device from the first fully expanded leaves and the tissues analyzed for nitrate using AEM, and water extraction procedures. The remainder of the samples were analyzed for total N by sulfuric acid-peroxide digestion using the method described by Thomas et al. in 1967 Agron. J. 99: 240–243.

Tissue Analyses Procedure

AEM Procedure

Plant leaf tissue was obtained from the desired plant part using a hole puncher. The hole puncher produced about 200 (about 2 g) small and uniform tissue pieces. The tissue pieces were placed in 100 mL plastic bottles and one strip of anion exchange membrane (AEM, size 6×2 cm was placed in each bottle. Then, 50 mL of deionized water was added. The bottles containing the leaf tissues+membrane+water were then capped and shaken on a gyratory shaker at 200 r.p.m. for 2 hours at room temperature. Following the shaking, the membranes were removed from the bottles and rinsed free of leaf tissue. The next step involved removal (elution) of the inorganic nitrate and phosphate absorbed to the membrane for measurement. The washed membranes were transferred to clean 50 mL centrifuge tubes and 20 mL of 0.5 M HCl was added as eluent. The membranes were shaken with the 0.5 M HCl for 30 minutes on the gyratory shaker. The membranes then were removed from the tubes and the eluents ware determined for nitrate and phosphate using an Autoanalyzer. The residual leaf tissue was dried at 60° C. and weighed.

Water Extraction Procedure

The procedure used in this study was similar to that outlined by Huang et al. Samples of leaf tissue obtained using hole puncher were weighed (about 2 g) and shaken on a gyratory shaker (200 r.p.m.) with 50 mL of deionized water for 2 hours at room temperature. The extractions were filtered through a filter paper and nitrate and phosphate in the extracts measured using an Autoanalyzer.

Total Tissue N Analysis 0.250 g of oven dry 20-mesh US plant sample was weighed into a digesting tube. Five mL of sulfuric acid was added into the tube. The rack of tubes was placed onto a digestion block at 360° C. and allowed to heat for 30 minutes. After 30 minutes, the rack of tubes were removed to cool. Once the tubes were cool, 0.5 mL of it $H_2O_2$ (30% hydrogen peroxide) was added and the rack was returned to the block to heat for 30 minutes. This procedure was continued (at least 6 times) until the solution had turned completely clear. Then, the tubes were brought to volume with deionized water. Each tube was shaken and the sample was poured into vials for analysis using an Autoanalyzer.

Reproducibility of the AEM Procedure

Means and coefficients of variation (C.V.) for triplicate tissue AEM extractions for the sunola are presented in Table 13. The AEM extraction procedure showed good reproducibility with coefficients of variation lower than 10% in all cases.

TABLE 13

AEM extractable nitrate and phosphate values for the sunola[¶]

| N level (mg/kg) | % $NO_3$-N[¶¶] | C.V. (%) | P level (mg/kg) | % P[¶¶] | C.V. (%) |
|---|---|---|---|---|---|
| 0 | 0.024 | 8.5 | 0 | 0.010 | 8.2 |
| 50 | 0.034 | 7.4 | 40 | 0.010 | 5.8 |
| 100 | 0.032 | 6.4 | 80 | 0.018 | 9.8 |
| 150 | 0.039 | 2.8 | 120 | 0.016 | 9.4 |
| 200 | 0.051 | 4.9 | 160 | 0.025 | 8.5 |

[¶]means of triplicate analyses
[¶¶]as per cent of dry weight basis.

Similarly, the AEM procedure showed good reproducibility for the nitrogen tissue analyses of spring wheat in the field experiment.

Relationship Between Test Methods

Both AEM and water extraction procedures gave similar test values for nitrate and phosphate in the leaf tissues of sunola and wheat. This is not surprising since the membrane simply acts to adsorb and accumulate the nitrate and phosphate that is removed from the leaf tissue by the water.

Linear regressions were used to evaluate the relationships between AEM and water extractable N, AEM extract N and total N, and water extractable N and total N (Table 14). AEM extractable N in wheat leaf tissue was significantly correlated with total N ($r^2 > 0.81$) and water extractable N ($r^2 > 0.61$). Water extractable N was also significantly correlated with total N. These findings are consistent with the similarity in mechanism by which AEM and water extractions act to remove nitrate from leaf tissue. The results also indicate that both AEM and water extractable N are good indicators of total N status in sunola and wheat plants.

Both AEM and water extraction methods offer advantages in terms of simplicity. Water volume during shaking is not highly critical in the AEM extraction, so that accurate and precise dispensing of deionized water is not required. The AEM strips are highly durable and do not appear to lose efficacy after prolonged usage. The only expendable chemical is the 0.5 M HCl used in the elution procedure. Another important consideration is the possibility of using a single extraction as an index for two or more elements.

TABLE 14

Regression equations and correlation coefficients ($r^2$) for relationships between the methods

| Plant species | Regression | Equation | | $r^2$ |
|---|---|---|---|---|
| | | | | n = 5 |
| Sunola | NAEM | = | 0.002477 + 0.8059 NW[¶¶] | 0.79** |
| | PAEM[¶] | = | 0.007825 + 1.1250 PW[¶¶] | 0.84** |
| Wheat | | | | n = 6 |
| AC Taber | NAEM | = | 0.004529 + 0.1263 NW | 0.84** |
| AC Reed | NAEM | = | −0.3676 + 0.5763 NW | 0.75** |
| BW 90 | NAEM | = | −0.001632 + 0.5150 NW | 0.81*** |
| Roblin | NAEM | = | 0.007739 + 0.6253 NW | 0.61** |
| Katepwa | NAEM | = | 0.009424 + 0.8216 NW | 0.92*** |
| AC Taber | NAEM | = | −0.004041 + 0.05996 Nt[¶¶¶] | 0.87*** |
| AC Reed | NAEM | = | −0.03791 + 0.2485 Nt | 0.93*** |
| BW 90 | NAEM | = | −0.01824 + 0.1292 Nt | 0.81*** |
| Roblin | NAEM | = | −0.9059 + 0.1072 Nt | 0.93*** |
| Katepwa | NAEM | = | −0.1716 + 0.1934 Nt | 0.91*** |
| AC Taber | NW | = | −0.5498 + 0.4198 Nt[¶¶¶] | 0.81*** |
| AC Reed | NW | = | −0.01386 + 0.03624 Nt | 0.88*** |
| BW 90 | NW | = | 0.03199 + 0.02496 Nt | 0.98*** |
| Roblin | NW | = | 0.02688 + 0.1068 Nt | 0.60** |
| Katepwa | NW | = | −0.1816 + 0.2201 Nt | 0.87*** |

[¶]Anion exchange membrane extractable N or P
[¶¶]Water extractable N or P
[¶¶¶]Total N
, * Significant at the 0.05 and 0.01 probability levels respectively Relationship Between N in Leaf Tissue and N Availability in Soil Regression analyses were used to describe the relationships between N in the leaf and N fertilizer rate applied. The results indicate strong direct relationships between nitrate concentrations in the plant leaves and the levels of N supply in the soil.

Figure 10A:
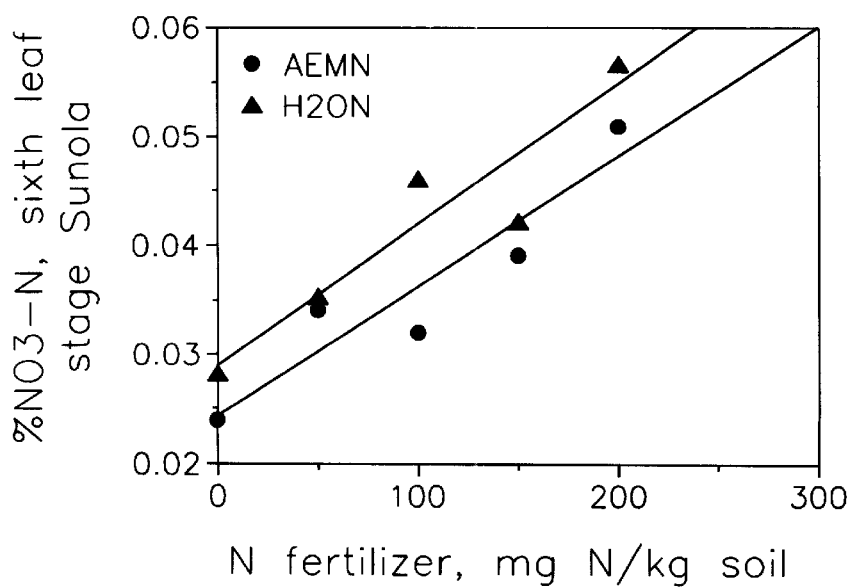
FIG. 10a represents the relationship between rate of nitrogen fertilizer application and % $NO_3$—N in leaf tissue of sunola plants as determined by resin membrane extraction.
Figure 10B:
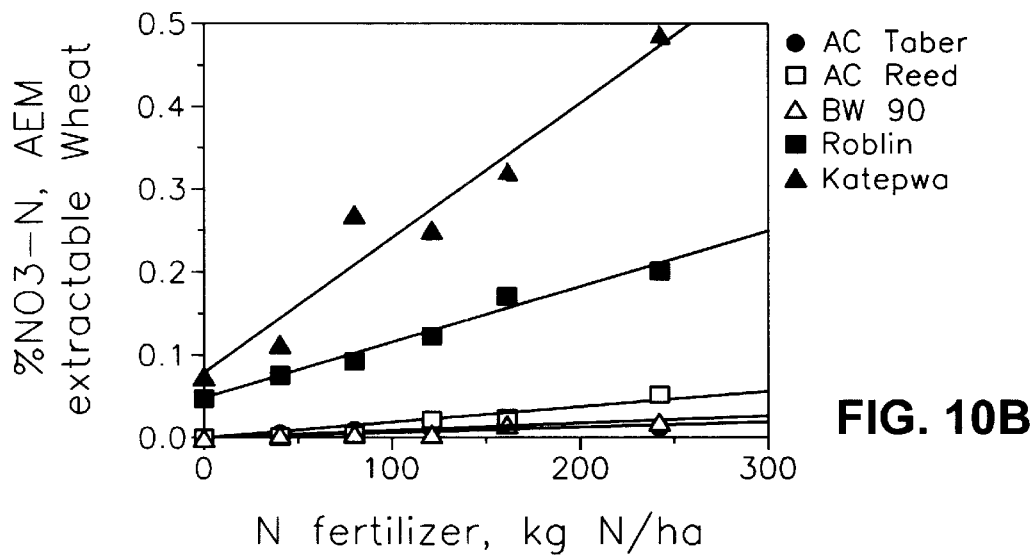
FIG. 10b represents the relationship between rate of nitrogen fertilizer application and % $NO_3$—N in leaf tissue of wheat plants as determined by resin membrane extraction.
Figure 10C:
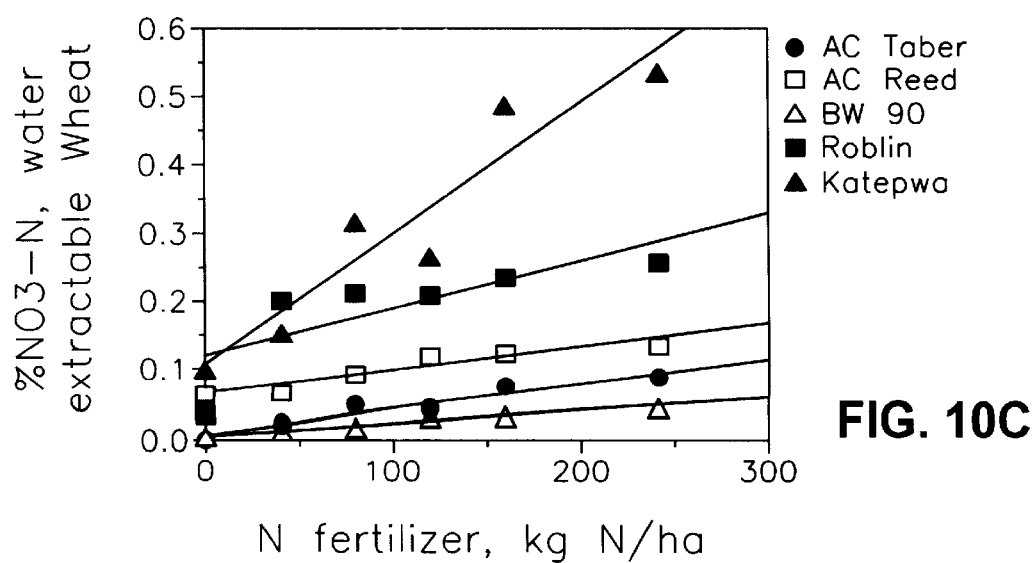
FIG. 10c represents the relationship between rate of nitrogen fertilizer application and % $NO_3$—N in leaf tissue of sunola plants as determined by water extraction.

The relationship between the percent $NO_3$—N in the tissue and the soil N supply for the sunola and wheat are shown in FIG. 10. The concentration of nitrate increased in the sunola and wheat leaves as the levels of N supply in the soil increased, indicating that the $NO_3$—N concentration in plant tissue reflects the N nutritional status of the plants, with greater concentration of AEM extractable nitrate associated with greater N availability. The results showed that the sampling time is suitable for diagnosing N nutritional status of the sunola (at sixth leaf stage) and wheat (at tillering stage). Sampling at an early growth stage may allow time for correction of nitrogen deficiencies in the current crop.

Relationship Between Nitrate in Leaf Tissue and Plant Yields

Figure 11A:
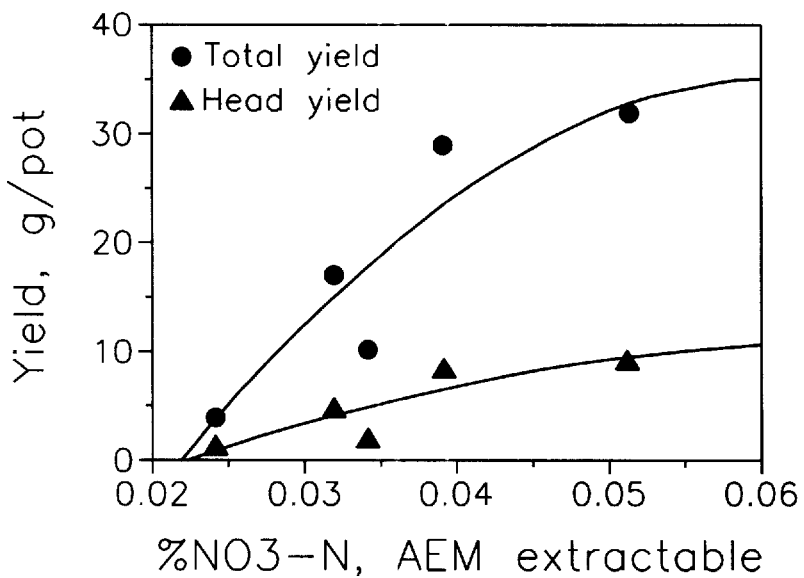
FIG. 11a represents the relationship between sunola yield and % $NO_3$—N in plant tissue as determined by resin membrane extraction.
Figure 11B:
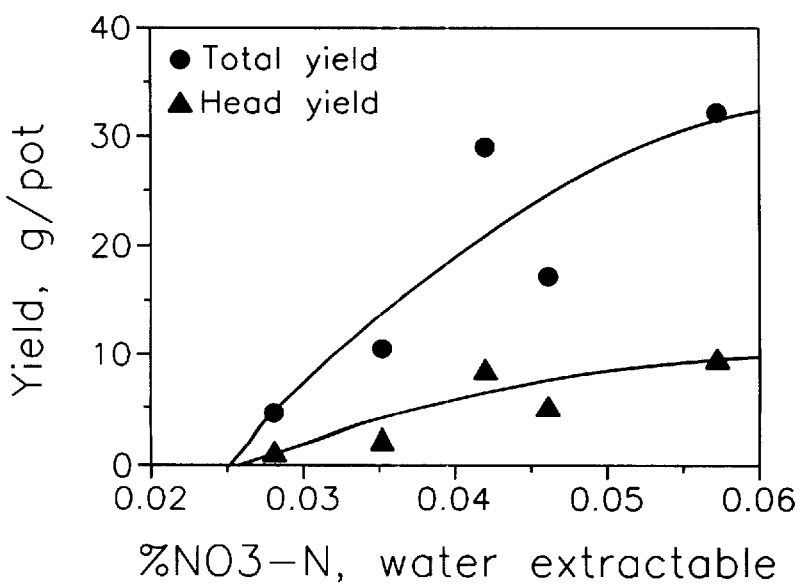
FIG. 11b represents the relationship between sunola yield and % $NO_3$—N in plant tissue as determined by water extraction.

As the dry matter and head yields of sunola significantly increased in response to greater N availability in soil, so did the nitrate concentration increase in the plant leaf tissues, reflecting the greater availability of soil N as fertilizer N rate was increased. FIG. 11 shows the relationships between nitrate concentrations in the sunola leaves and the plant dry matter yields. Similar to the dry matter yields, good relationships were found between nitrate concentrations in the sunola leaves and the plant dry matter yields. Similar to the dry matter yields, good relationships were found between nitrate concentrations in the sunola leaves and the plant head yields.

Figure 12A:
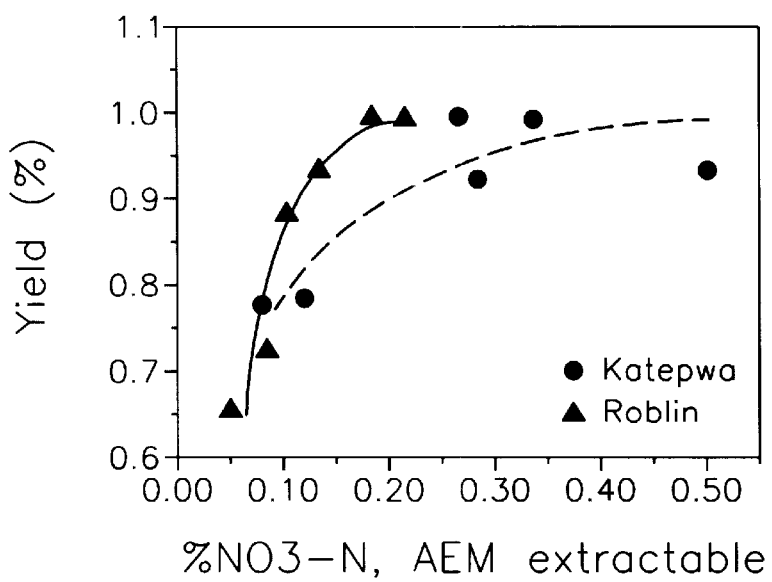
FIG. 12a represents the relationship between plant seed yields (expressed as percentage of maximum yield) and % $NO_3$—N in plant tissue as determined by resin membrane extraction.
Figure 12B:
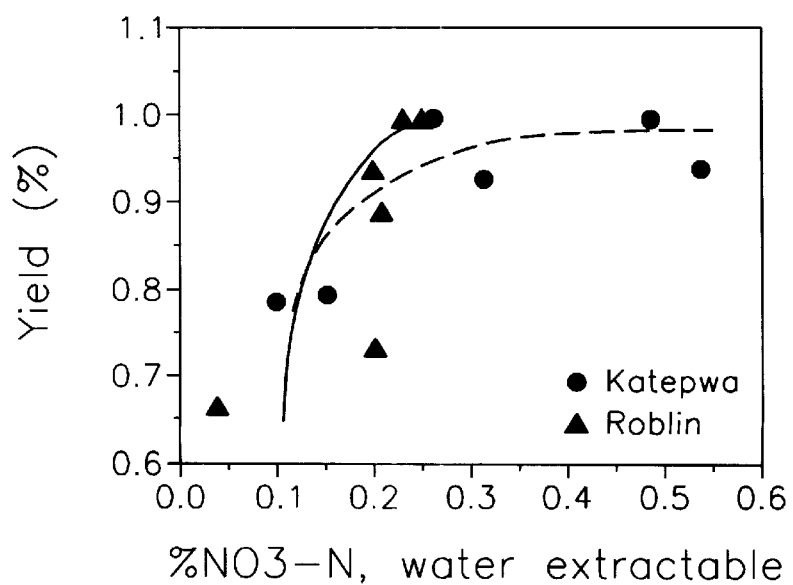
FIG. 12b represents the relationship between wheat seed yields (expressed as percentage of maximum yield) and % $NO_3$—N in plant tissue as determined by water extraction.
Figure 12C:
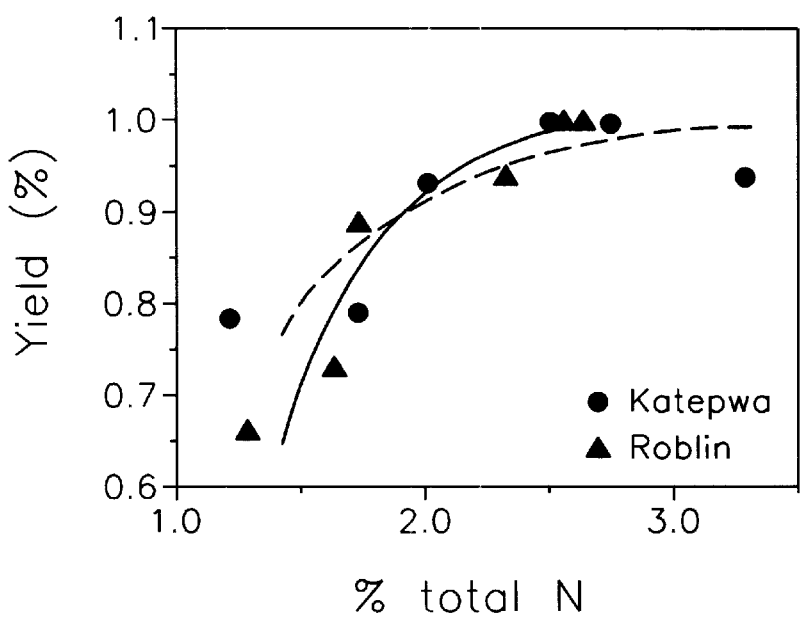
FIG. 12c represents the relationship between what seed yields (expressed as percentage of maximum yield) and % $NO_3$—N in plant tissue as determined by tissue digestion.
Figure 13A:
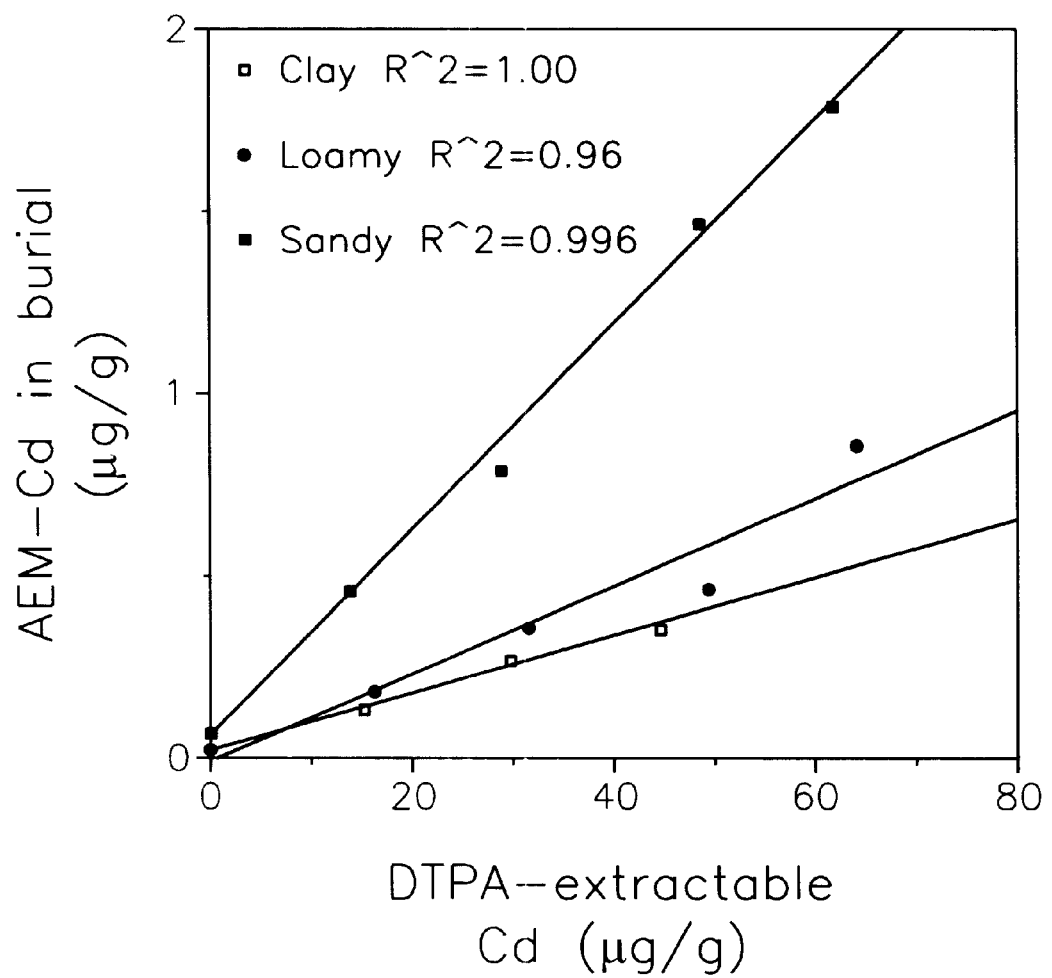
FIG. 13a represents the relationship for three soils between cadmium extracted from soil by anion exchange membrane burial and cadmium extracted by DTPA solution.
Figure 13B:
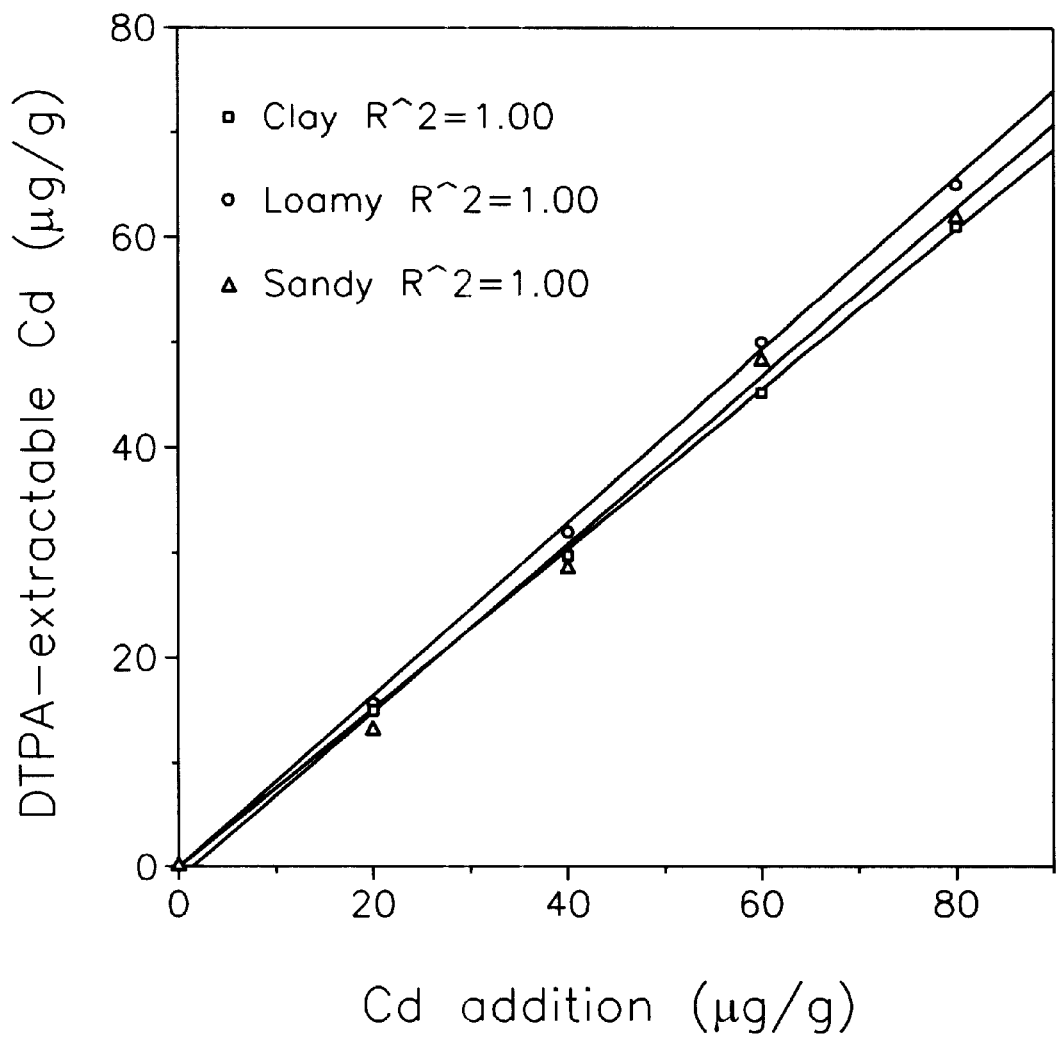
FIG. 13b represents the relationship for three soils between cadmium extracted from soil by DTPA solution and rate of cadmium addition to the soil.
Figure 13C:
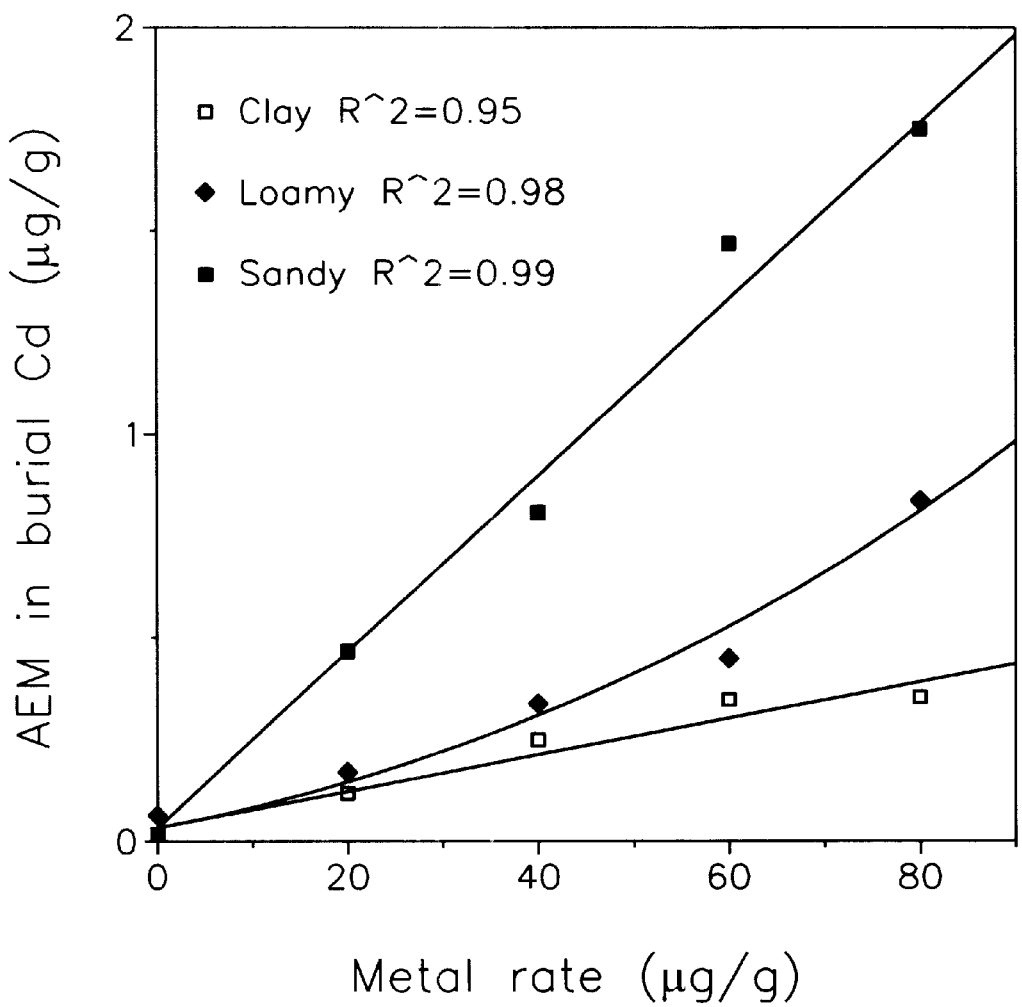
FIG. 13c represents the relationship for three soils between cadmium extracted from soil by anion exchange membrane burial and rate of cadmium addition to the soil.
Figure 13D:
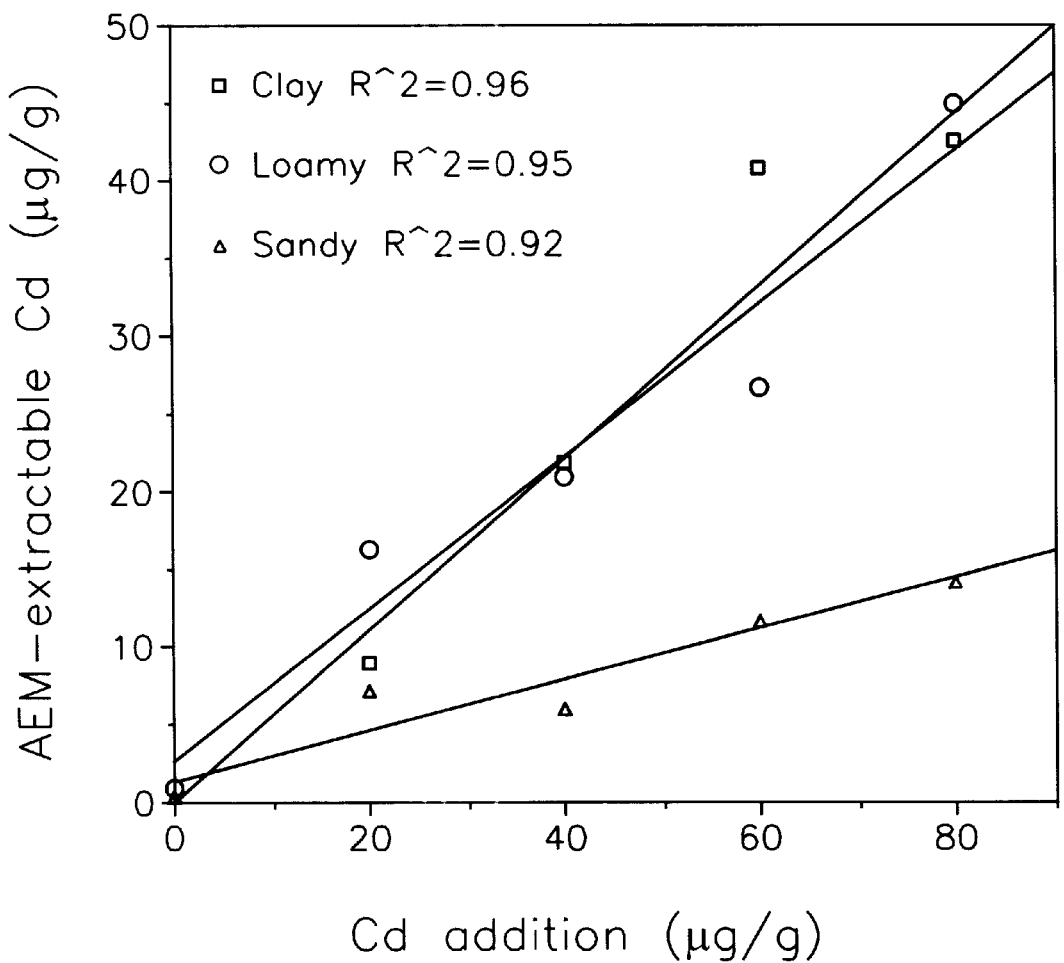
FIG. 13d represents the relationship for three soils between cadmium extracted from soil-water suspension with anion exchange membrane and rate of cadmium addition to the soil.
Figure 13E:
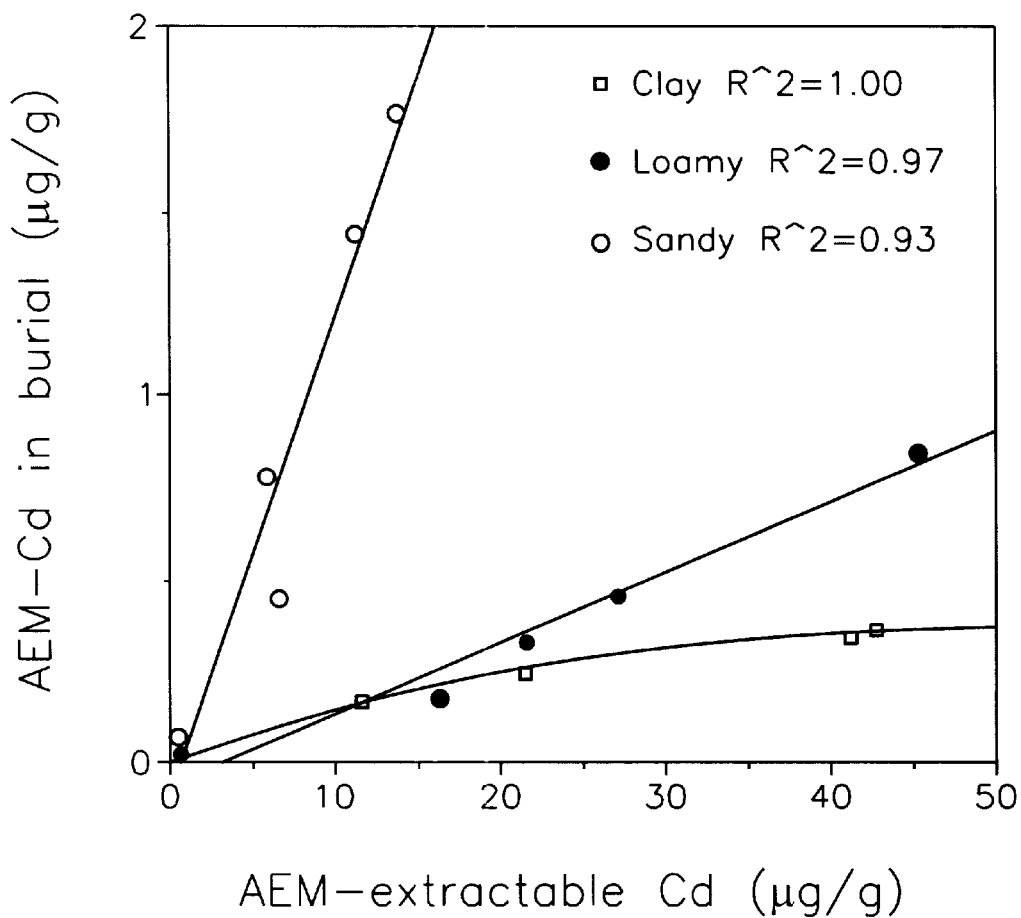
FIG. 13e represents the relationship for three soils between cadmium extracted from soil by anion exchange membrane burial and cadmium extracted from soil-water suspension by anion exchange membrane.
Figure 14A:
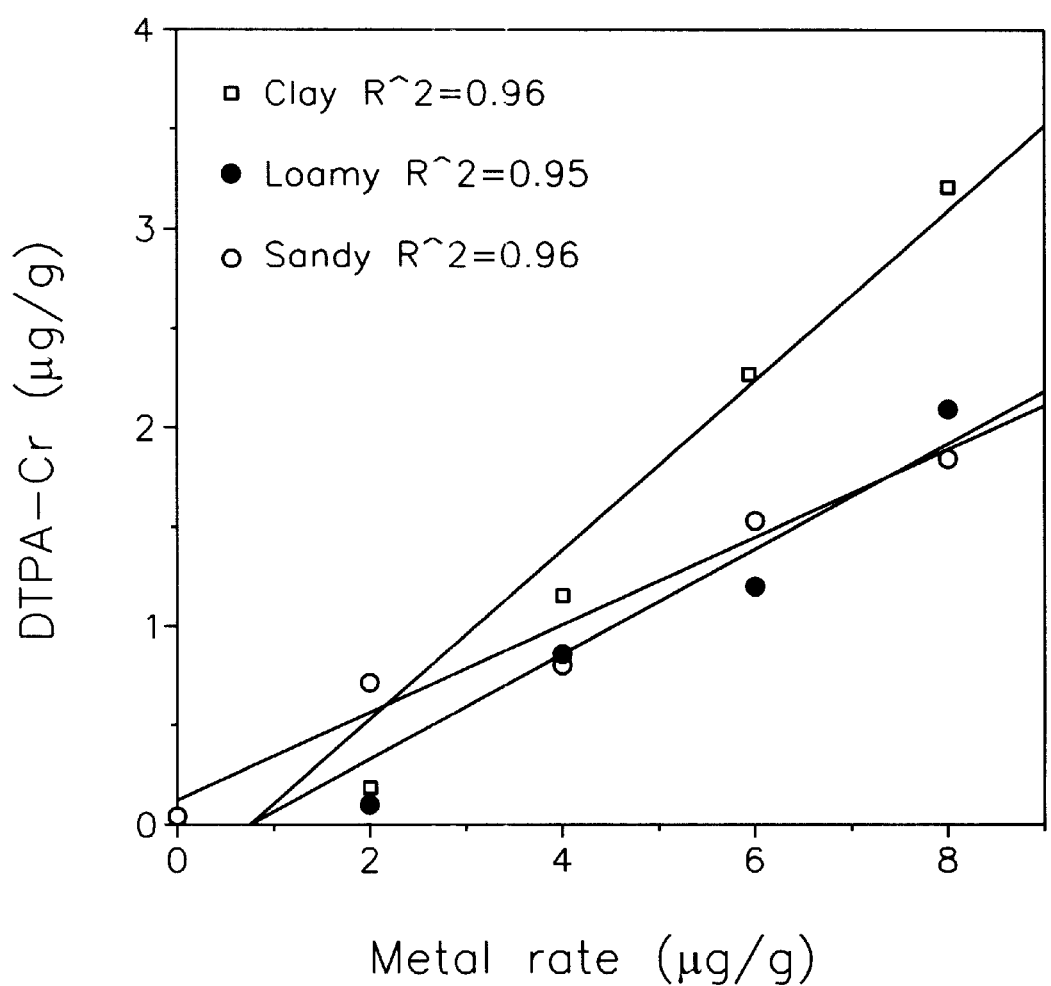
FIG. 14a represents the relationship for three soils between chromium extracted from soil by DTPA solution and rate of chromium addition to the soil.
Figure 14B:
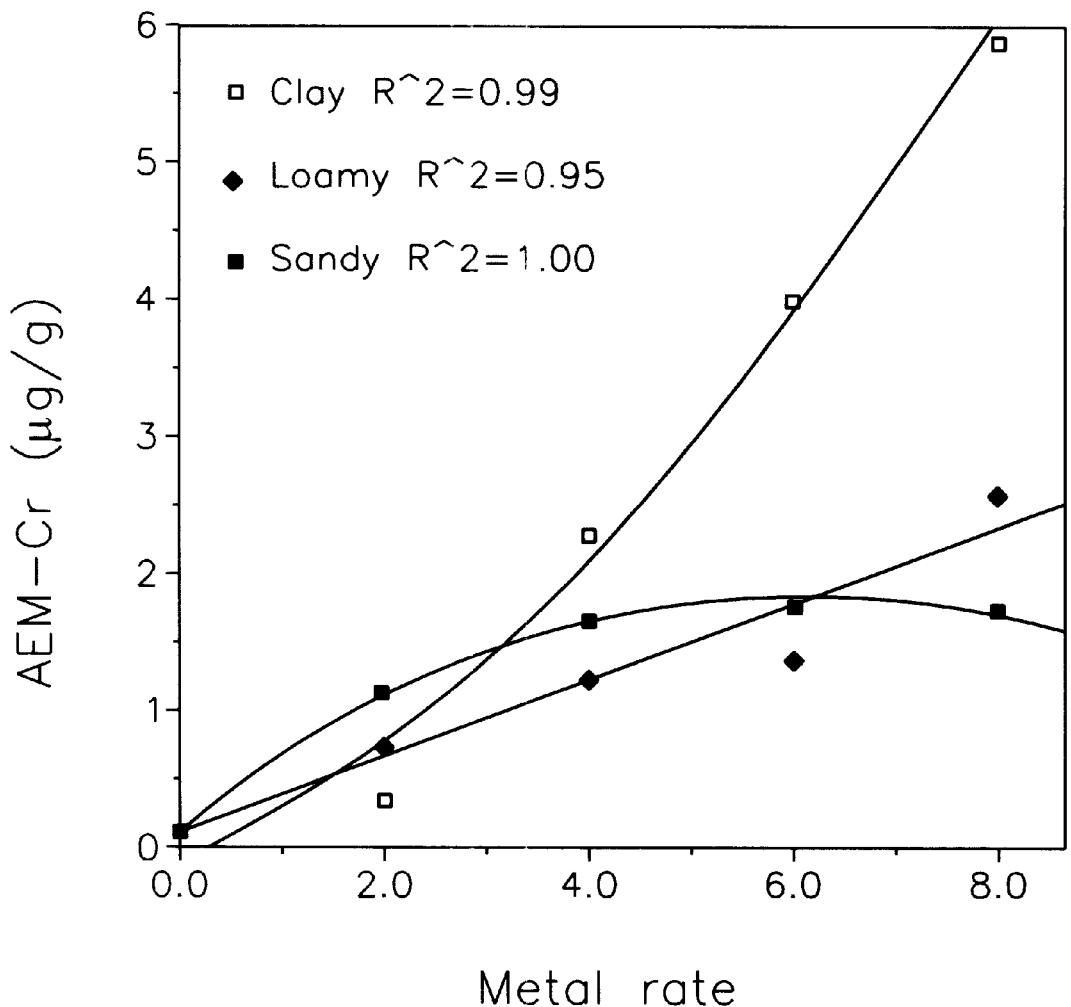
FIG. 14b represents the relationship for three soils between chromium extracted from soil-water suspension with anion exchange membrane and rate of chromium addition to the soil.
Figure 14C:
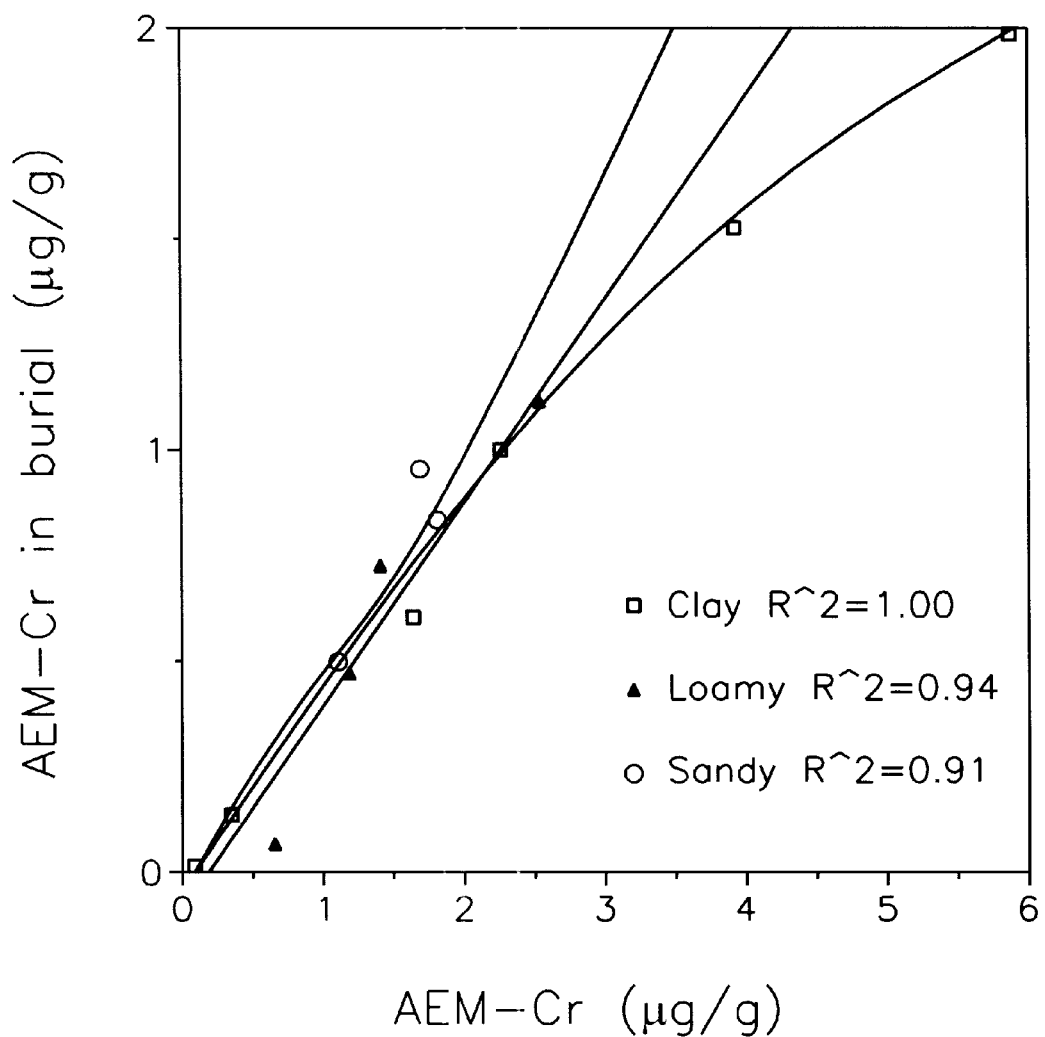
FIG. 14c represents the relationship for three soils between chromium extracted from soil by anion exchange membrane burial and chromium extracted from soil-water suspension by anion exchange membrane.
Figure 14D:
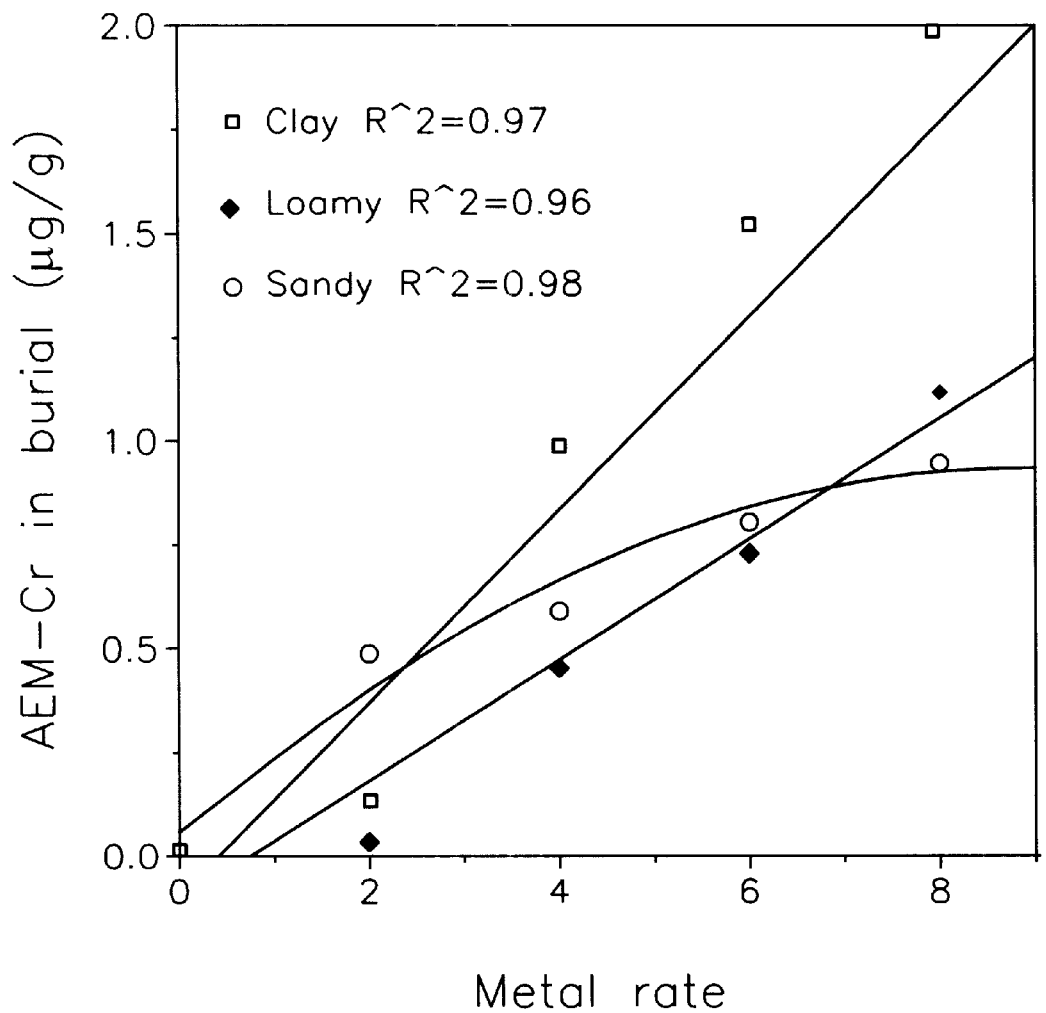
FIG. 14d represents the relationship for three soils between chromium extracted from soil by anion exchange membrane burial and rate of chromium addition to the soil.
Figure 14E:
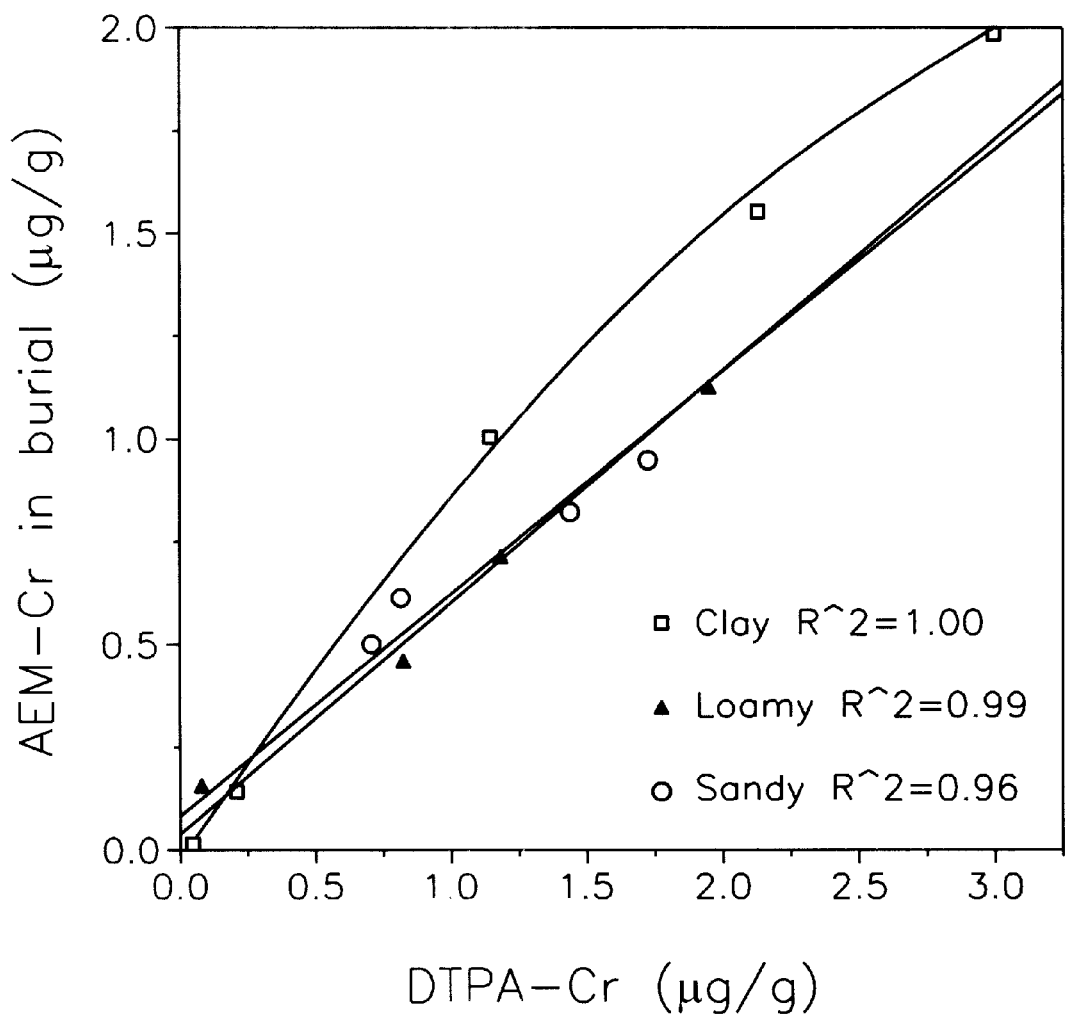
FIG. 14e represents the relationship for three soils between chromium extracted from soil by anion exchange membrane burial and chromium extracted by DTPA solution.
Figure 15A:
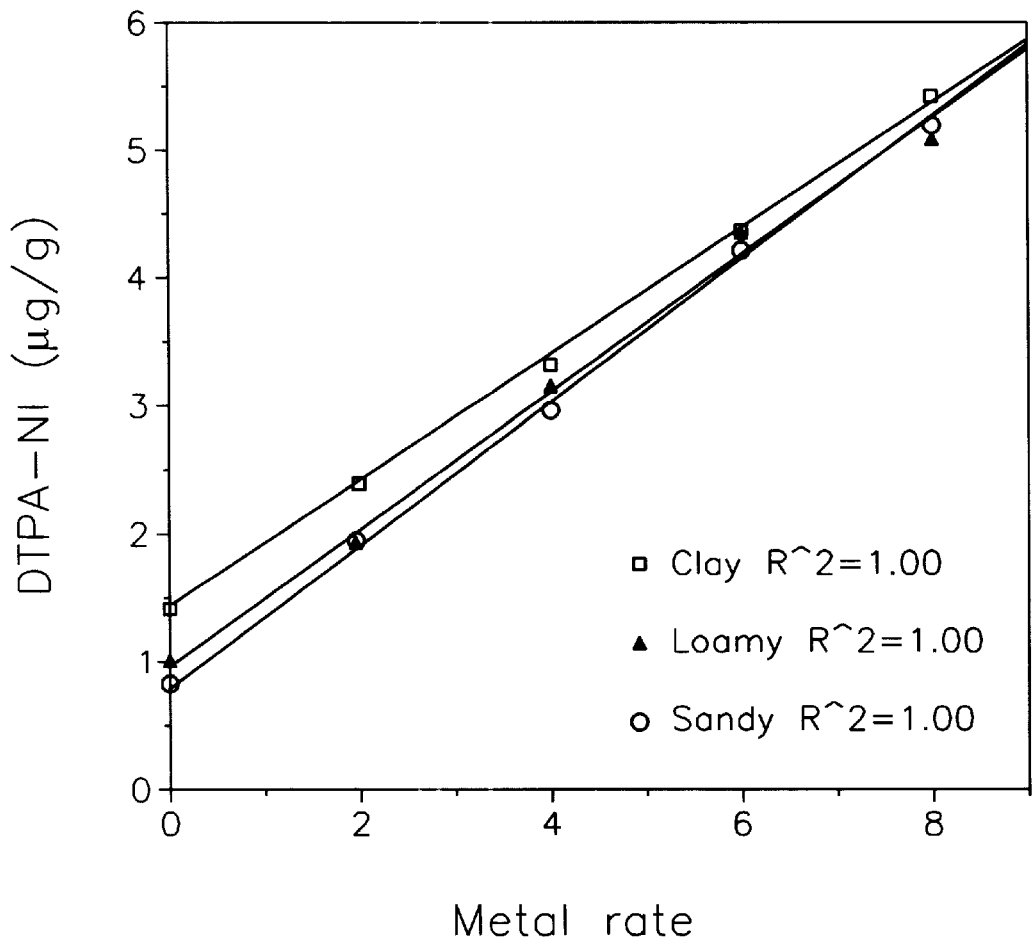
FIG. 15a represents the relationship for three soils between nickel extracted from soil by DTPA solution and rate of nickel addition to the soil.
Figure 15B:
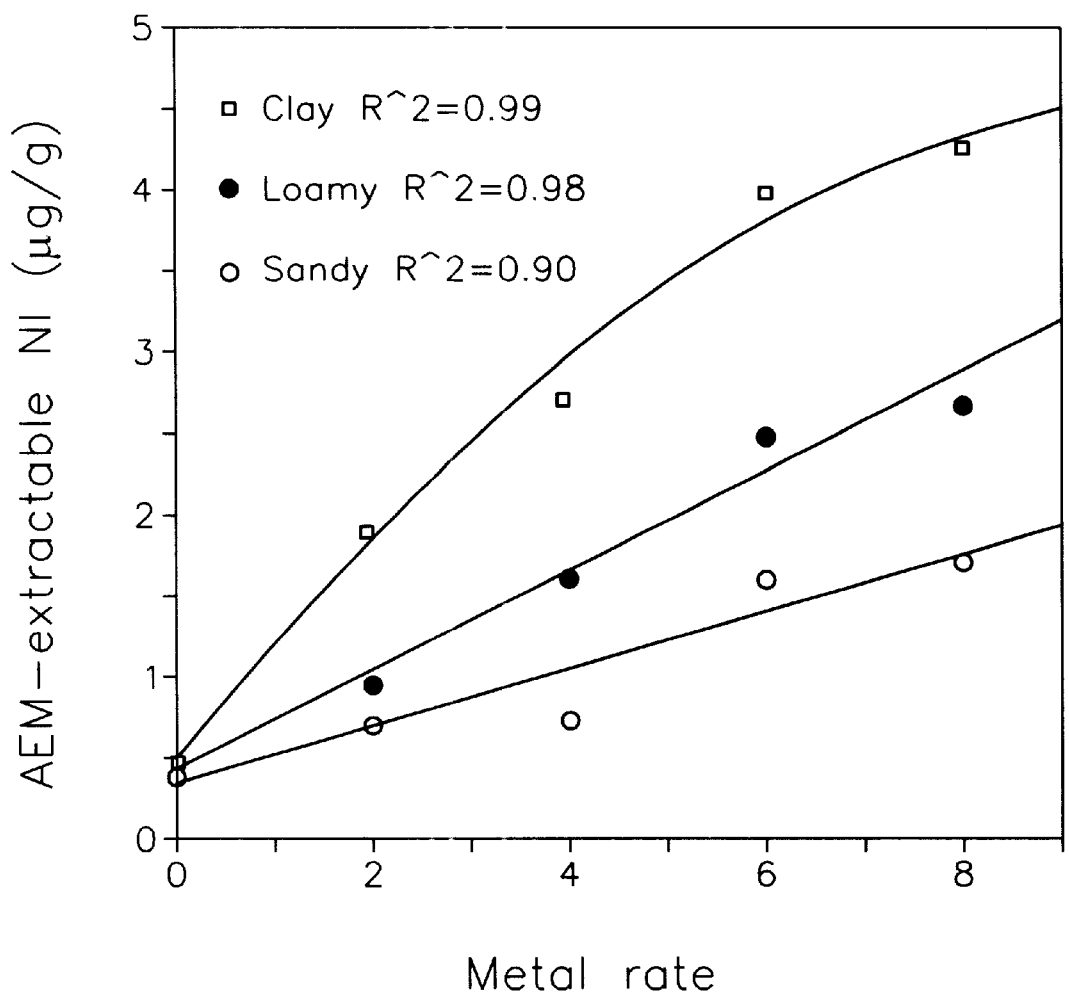
FIG. 15b represents the relationship for three soils between nickel extracted from soil-water suspensions with anion exchange membrane and rate of nickel addition to the soil.
Figure 15C:
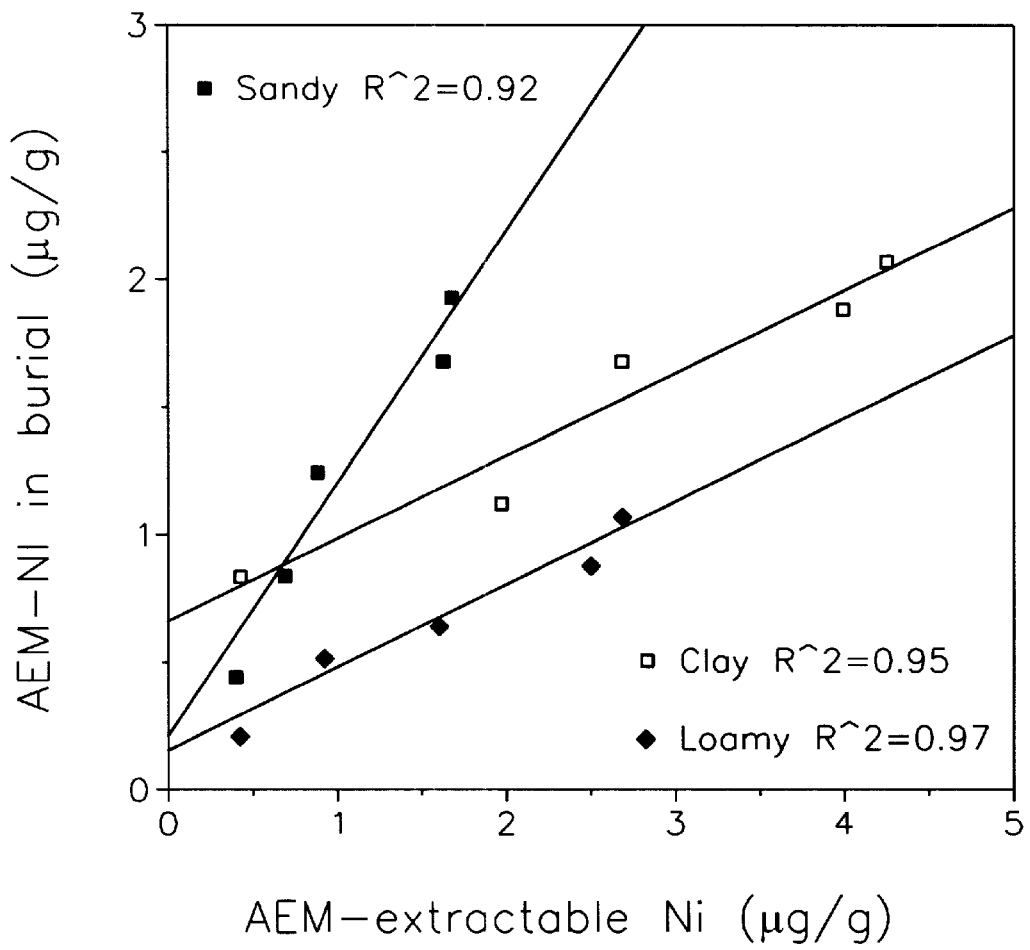
FIG. 15c represents the relationship for three soils between nickel extracted from soil by anion exchange membrane burial and nickel extracted from soil-water suspension by anion exchange membrane.
Figure 15D:
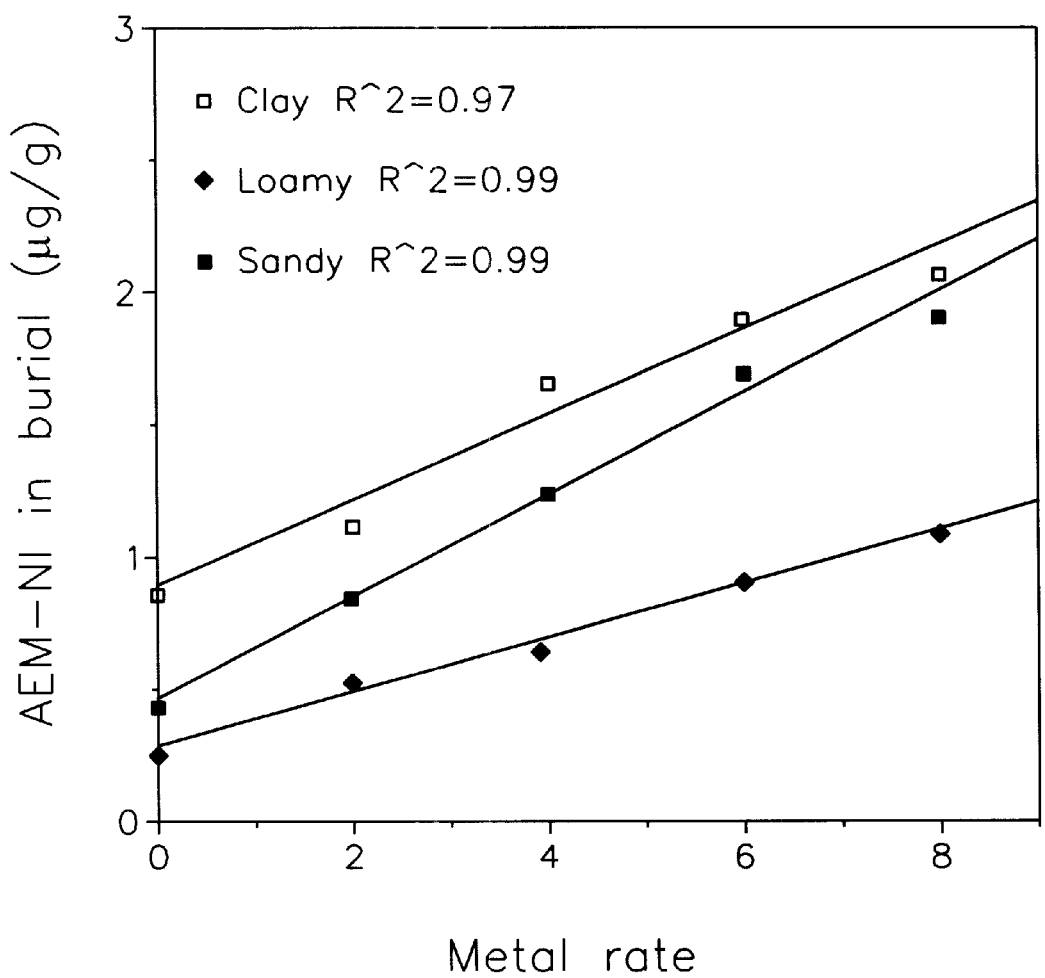
FIG. 15d represents the relationship for three soils between nickel extracted from soil by anion exchange membrane burial and rate of nickel addition to the soil.
Figure 15E:
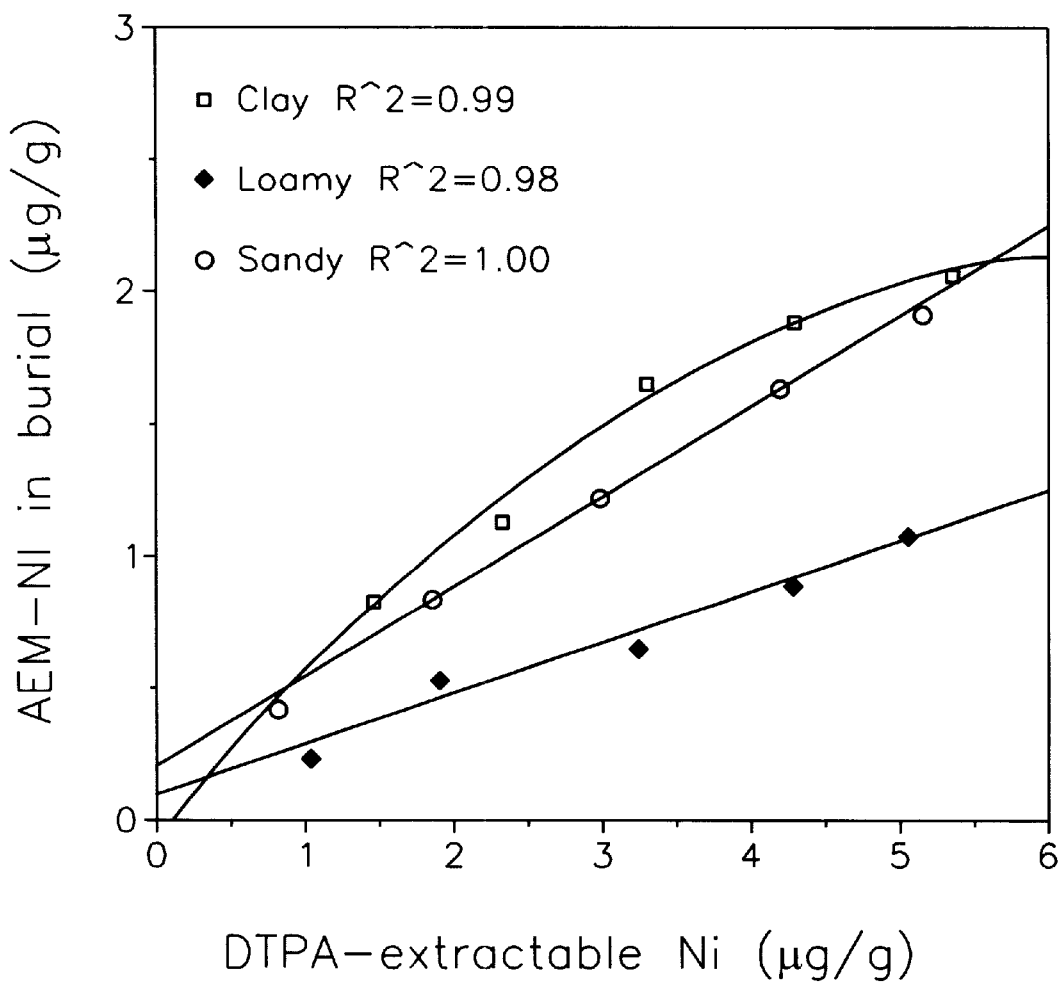
FIG. 15e represents the relationship for three soils between nickel extracted from soil by anion exchange membrane burial and nickel extracted by DTPA solution.
Figure 16A:
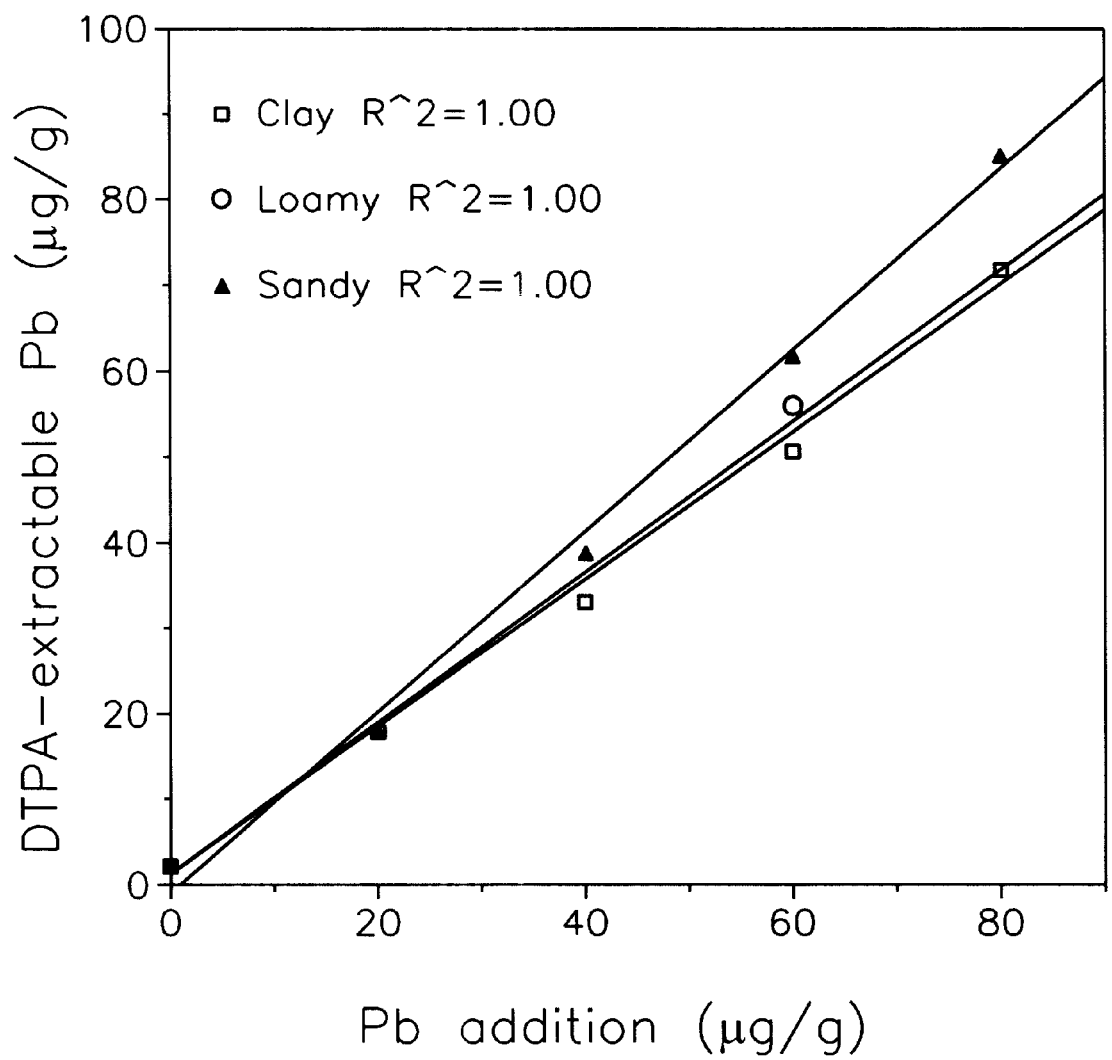
FIG. 16a represents the relationship for three soils between lead extracted from soil by DTPA solution and rate of lead addition to the soil.
Figure 16B:
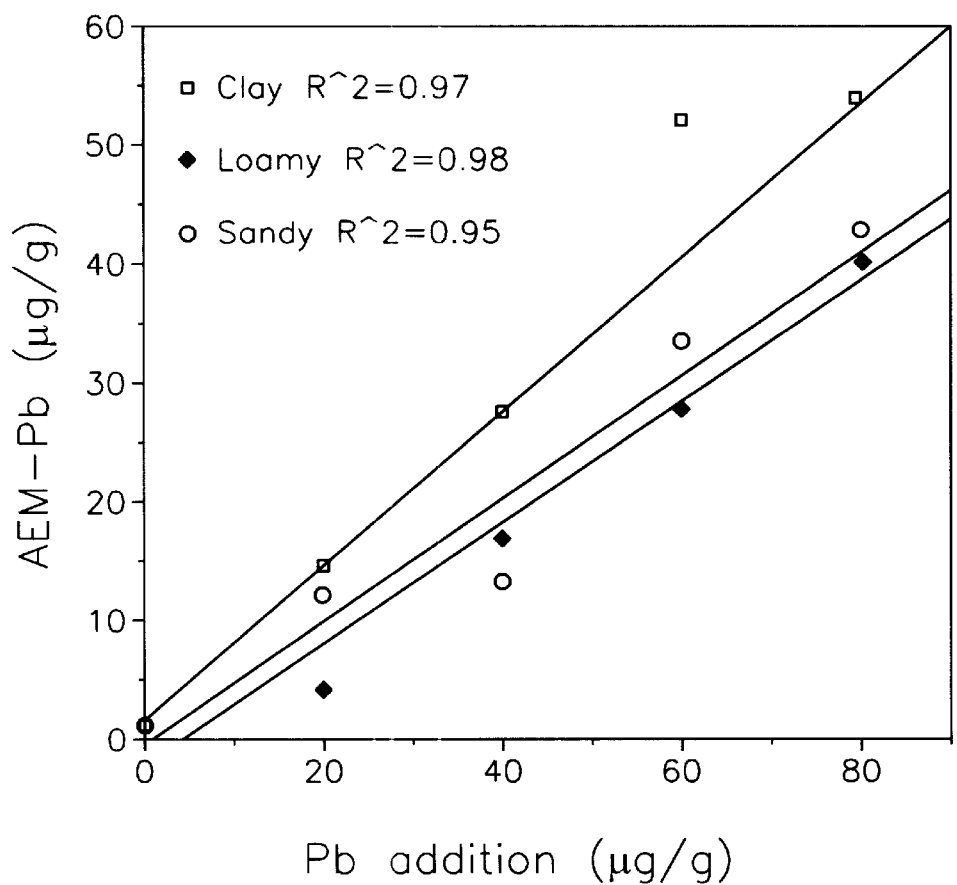
FIG. 16b represents the relationship for three soils between lead extracted from soil-water suspensions with anion exchange membrane and rate of lead addition to the soil.
Figure 16C:
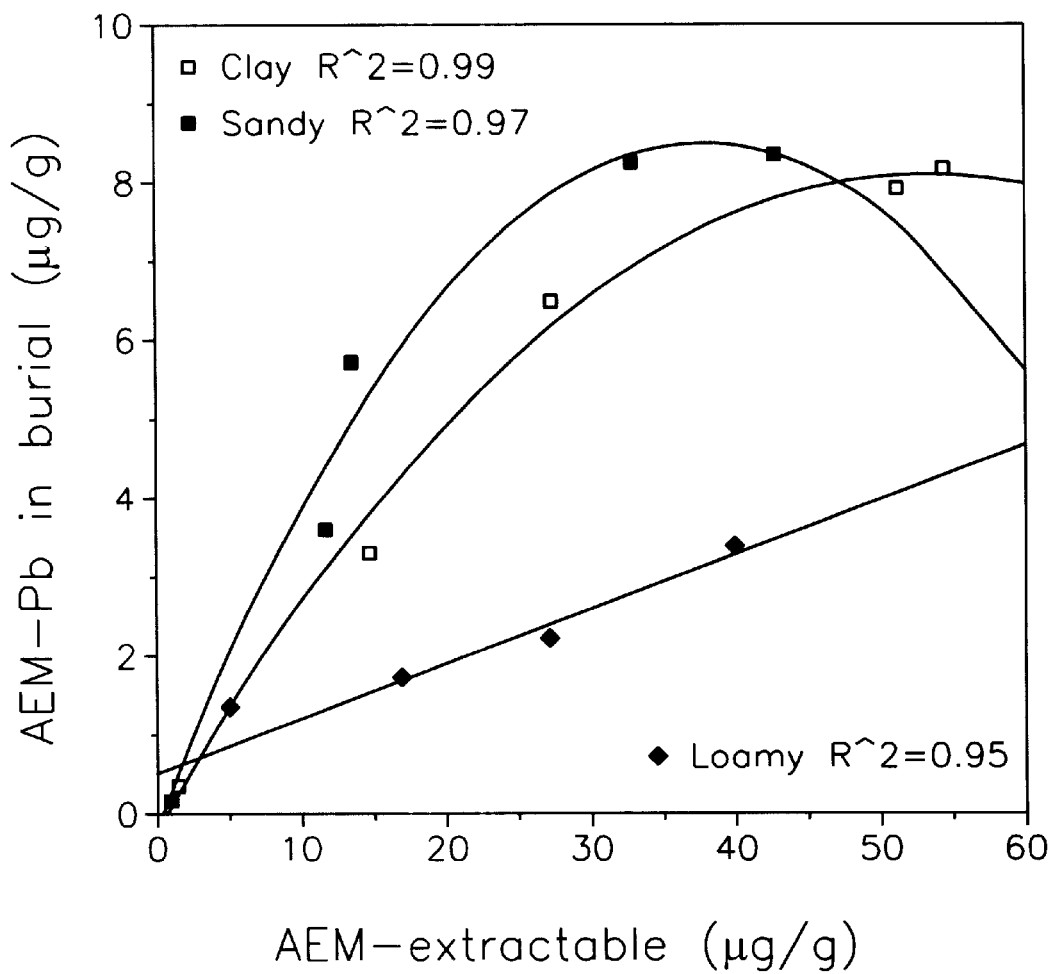
FIG. 16c represents the relationship for three soils between lead extracted from soil by anion exchange membrane burial and lead extracted from soil-water suspension by anion exchange membrane.
Figure 16D:
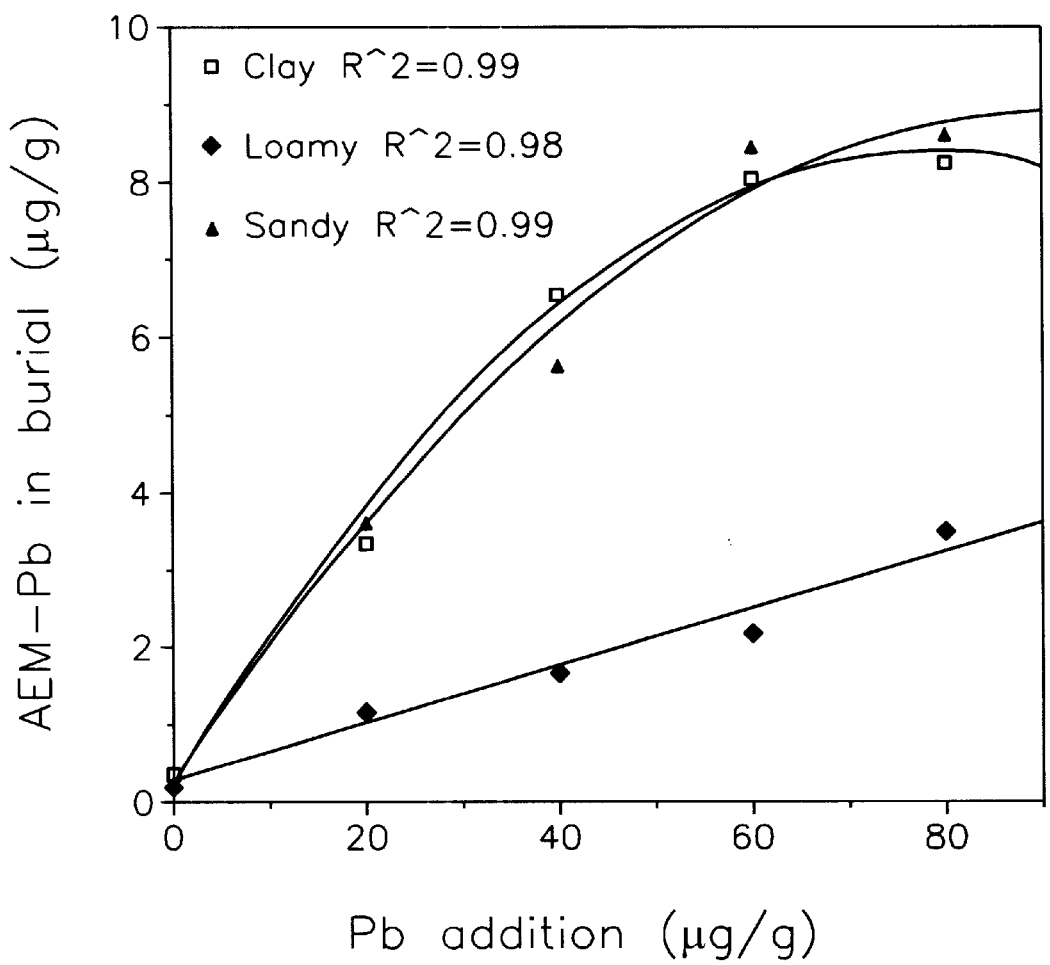
FIG. 16d represents the relationship for three soils between lead extracted from soil by anion exchange membrane burial and rate of lead addition to the soil.
Figure 16E:
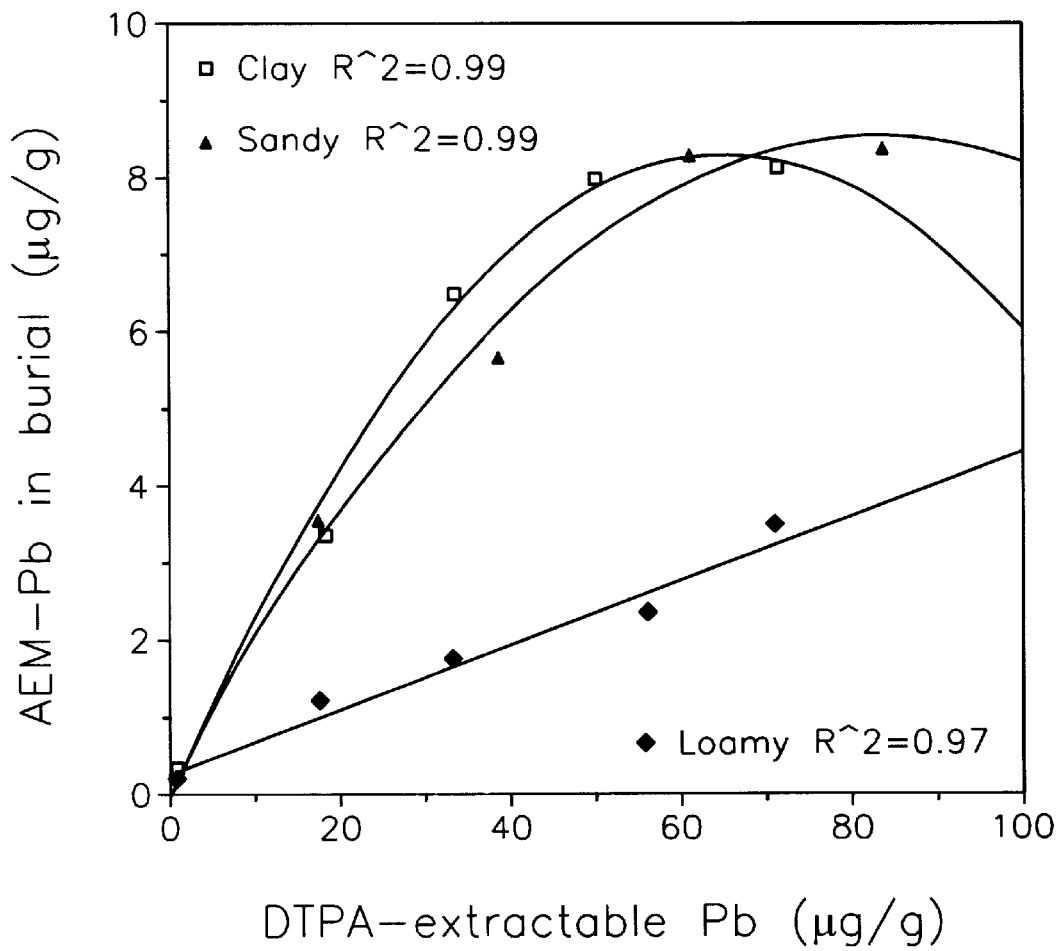
FIG. 16e represents the relationship between lead extracted from soil by anion exchange membrane burial and lead extracted by DTPA solution.

FIG. 12 shows the relationship between nitrate concentrations in the plant leaves and the final seed yields of Katepwa and Roblin. Similar trends were also found for the other varieties of wheat. Seed yields increased as nitrate concentration increased in the leaf tissues, indicating that the percent $NO_3$—N in the leaf is sensitive to the N nutritional status of the plants as it affects yields.

The critical tissue concentration of a nutrient has been suggested as that associated with 80 to 90 percent of the maximum yield. Most workers identify a critical nutrient range (CNR). Tissue concentrations in the critical nutrient range are considered to represent a nutrient supply adequate for maximum growth and development. Tissue concentrations below the CNR indicate deficiency. At the sixth leaf stage for sunola, the CNR for AEM extractable $NO_3$—N is from 0.04% $NO_3$—N to 0.05% $NO_3$—N (FIG. 11). The head yield of sunola significantly decreased when the leaf contained lower than 0.030% $NO_3$—N at the sixth leaf stage. The critical nutrient range for AEM extractable nitrate ranged from 0.20 to 0.30% $NO_3$—N for Roblin and Katepwa wheat (FIG. 12). For total N the CNR appears to range from 2.0 to 2.5% N.

AEM and Water Extractable Inorganic P in Leaf Tissue and Yields of Sunola

Table 15 reports the AEM and water extractable inorganic phosphate values, and dry matter yields of sunola. The concentration of inorganic phosphate increased in the sunola leaf tissues as the levels of P supply increased in the soil, indicating that the inorganic phosphate concentration in plant tissue reflects the P nutritional status of the plants, with greater concentration of AEM extractable phosphate associated with greater P availability. The results also showed that the plant dry matter yields increased as inorganic phosphate concentration increased in the plant leaf tissues, reflecting the greater availability of soil P as fertilizer P rate was increased. Ninety percent of the maximum yield was obtained when the leaf contained 0.018% AEM extractable phosphate.

TABLE 15

Inorganic phosphate and yields of the sunola[¶]

| P level | P (%)[¶¶] | | Yield (g/pot) | |
|---|---|---|---|---|
| (mg/kg) | AEM | $H_2O$ | Dry weight | Head weight |
| 0 | 0.010 | 0.016 | 15.5 | 3.1 |
| 40 | 0.010 | 0.015 | 17.9 | 4.4 |
| 80 | 0.018 | 0.024 | 17.8 | 4.6 |
| 120 | 0.016 | 0.024 | 20.5 | 4.6 |
| 160 | 0.025 | 0.026 | 21.5 | 4.7 |

The use of AEM and water to extract nitrate from fresh sunola and wheat leaf tissues provides a simple index of N nutritional status of plants and could provide a useful guide to N fertilization. Nitrate concentrations increased in leaf tissue as the available N supply in the soil was increased through fertilization. Nitrate concentration (%) in the leaves of sunola and wheat was found to be satisfactory indicator of N deficiency or sufficiency in sunola and wheat. The AEM and water extraction procedures can be used to provide a simple simultaneous index of plant N, P and S status.

It was convenient to leave the anion-exchange membrane overnight for 16 hours but it is believed that much shorter times, that is approximately 1 hour, are sufficient to fully absorb the phosphate found in the solution.

EXAMPLE 8

Immobilization of Trace Metals on Anion-Exchange Membranes From a Soil Suspension Anion and cation-exchange membranes of 2 cm×6 cm from BDH were pretreated by placing them into a solution of 0.1 M EDTA to produce a membrane saturated with EDTA. The membranes were then taken out and placed in a container containing 5 grams of soil and 100 ml of water. This mixture was shaken for 4 hours. The membranes were then removed, washed free of soil and debris with water and placed in 0.5 M HCl for elution. The concentration of Fe and Cu were determined in the solution using plasma-emission spectrometry (ARL Model 3410+ Inductively Coupled Plasma Spectrometer) using methods well-known to those skilled in the art. Results are shown in FIG. 7.

It is to be noted that the results provided in this example are preliminary and were obtained in the laboratory rather than in the field and were determined by shaking the soil with the membrane rather than burial. However, it would appear that similar results could be obtained under field burial conditions.

Figure 7A:
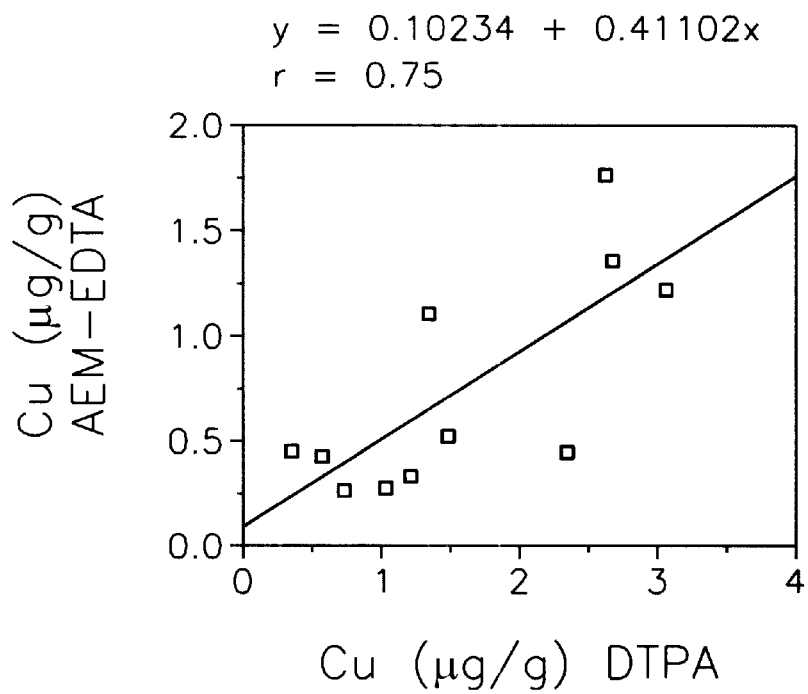
FIG. 7a represents the relationship between copper extracted by anion exchange membrane treated with ETDA and copper extracted with DTPA extracting solution.
Figure 7B:
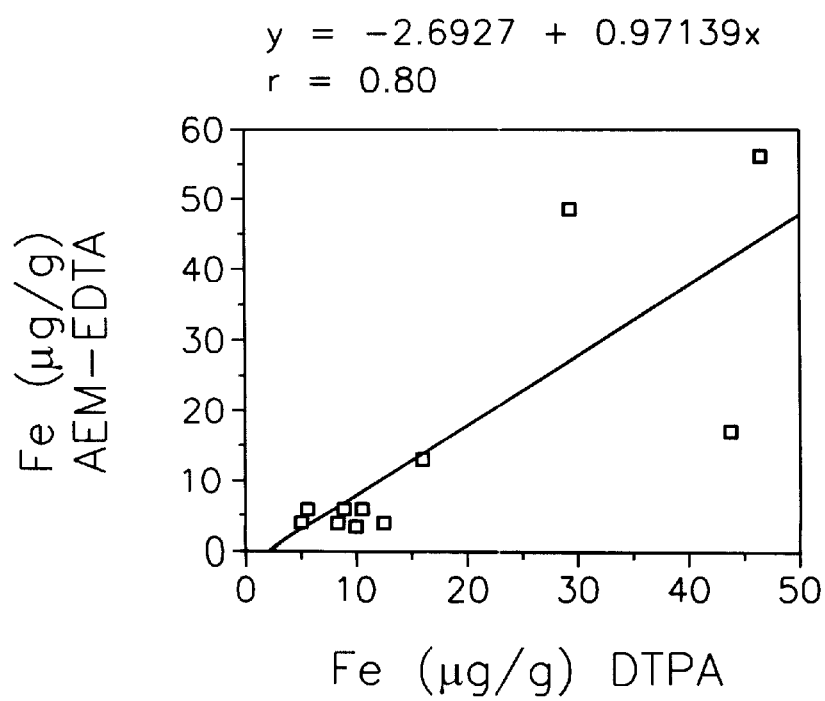
FIG. 7b represents the relationship between iron extracted by anion exchange membrane treated with ETDA and iron extracted with DTPA extracting solution.

As shown in FIG. 7, significant correlations (r=0.75) were observed between anion-exchange membrane EDTA and the conventional laboratory DPTA extraction for copper and iron. This suggest that the AEM-EDTA extraction is as good, if not better, at removing the bioavailable pool as the conventional tests now in use.

It is important to note that in this particular example, macronutrient cations are extracted using an anion-exchange membrane treated with EDTA chelating agent. It is hypothesized that 1 or 2 negatively charged carboxyl groups on the EDTA molecule result in binding to the positively charged sites on the anion-exchange membranes. As there are 4 negatively charged carboxyl groups on each EDTA molecule, this still leaves 2 or 3 negatively charged sites to selectively bind and complex the metal cation.

EXAMPLE 9

In-Situ Immobilization of Metals on Anion-Exchange Membranes

Three soil types (clay, loam, sand) were spiked with 0, 20, 40, 60 and 80 mg of cadmium (Cd) and lead (Pb); and 0, 2, 4, 6, 8 mg of chromium (Cr) and nickel (Ni) in solution form. The soils were then wetted to field capacity and incubated for one week to allow equilibration. One strip of anion exchange membrane (AEM) (2 cm×5 cm) pretreated with DTPA chelating agent (0.01 M DTPA+0.02 N NaOH) was then buried in each of the treatments for 24 hours, removed, washed free of adhering soil, and placed in 20 ml, of 1 M HCl for 2 hours to remove (elute) the absorbed metals from the strips. The conventional DTPA extraction for available metals was carried out by taking a 20 g subsample of the soil and shaking it with 40 mL of 0.005 M DTPA solution in an Erlenmyer flask on a reciprocating shaker.

The data presented in FIGS. 13–16 show a strong linear relationship between the amount or metal removed by the AEM burial and the level of contamination (rate of addition) of the metal in the soil. As well there is a strong relationship between amount of metal removed by AEM burial and that removed by the conventional DTPA extraction.

EXAMPLE 10

Evaluation of Phosphate Concentrations in a Liquid Sample

Phosphate was added in known concentrations to a vial containing 30 ml of deionized water. A strip of anion-exchange membrane purchased from BDH Ltd. (2 cm×6 cm) was added and the vial was left to sit overnight for a period of 16 hours. The membrane was then removed from the solution, rinsed with deionized water and placed in a clean tube containing 0.5 M HCl eluent. The phosphate in the eluent was measured using the acid-molybdate blue color development procedure on a Technicon Auto-analyzer system. The data as shown in Table 16 below shows complete recovery by the membrane strip of the added phosphate at both low and high concentrations.

TABLE 18

Amount of phosphate recovered in a liquid sample using a strip of anion-exchange membrane

| $\mu$g P added | vs | $\mu$g P recovered by membrane |
|---|---|---|
| 5.3 | | 5 |
| 10.6 | | 10.3 |
| 21.2 | | 20.5 |
| 53.1 | | 52.6 |
| 79.7 | | 79.8 |
| 106.2 | | 108.6 |
| 212.5 | | 210.5 |
| 531.1 | | 521.9 |

What is claimed is:

1. A kit for the in situ measurement of ion availability in a solid medium, said kit comprising:

ion-exchange material having a known surface area and a measurable ion uptake potential, said ion-exchange material being in an ionic form adapted to immobilize available ions from said solid medium on said material by direct in situ contact of said ion-exchange material with said solid medium, wherein said ion-exchange material is in the form of a film, sheet, or membrane;

means to remove any adhering particles of said solid medium from said ion-exchange material after contact between said solid medium and said ion-exchange material; and a receptacle for containing said ion-exchange material after the removal of any said adhering particles.

2. A kit according to claim 1, wherein said ion-exchange material is a cation, anion or zwitterion-exchange material.

3. A kit according to claim 1, wherein said receptacle further contains a solution with sufficient ionic concentration to displace anions, cations or zwitterions immobilized on said ion-exchange material from said ion-exchange material into said solution.

4. A kit according to claim 1, which further comprises means for selecting a predetermined volume of a sample of the medium to be analyzed.

5. A kit according to claim 3, wherein said solution is a solution of hydrochloric acid.

6. A kit according to claim 4, wherein said solution is a solution of sodium bicarbonate.

7. A kit according to claim 6, wherein said receptacle is a flexible pouch with a water-tight closure.

8. A kit according to claim 1, further comprising a device to mark the location of said ion-exchange material in said medium.

9. A kit according the claim 2, wherein said ion-exchange material is cation-exchange material composed of polystyrene cross-linked with vinylbenzene and having attached thereto sulphonic acid moieties.

10. A kit according to claim 1, wherein said ion-exchange material is pretreated to enhance immobilization of ions from said medium onto said material when said material is in contact with said medium.

11. A kit according to claim 10, wherein said ion-exchange material is pretreated to enhance immobilization of plant nutrients from a solid medium onto said material when said material is inserted in a solid medium.

12. A kit according to claim 11, wherein said material is pretreated to enhance immobilization of plant nutrients selected from the group consisting of nitrogen, phosphorous, potassium, sulphur, calcium, magnesium and micronutrients.

13. A kit according to claim 12, wherein said material is pretreated with dilute HCl or $NaHCO_3$.

14. A kit according to claim 10, wherein said material is pretreated with a chelating agent to enhance complexing and immobilization of trace metals from said medium onto said material when said material is contacted with said medium.

15. A kit according to claim 14, wherein said chelating agent is ethylenediamine tetraacetic acid or diethylenetriamine pentaacetic acid.

16. A kit according to claim 1, wherein said means to remove said liquid or solid medium from said ion-exchange material is a washing solution characterized in that it is free from ions that can be immobilized on said ion-exchange material and free from ions that can displace ions immobilized on said ion-exchange material.

17. A kit according to claim 16, wherein said means to remove said liquid or solid medium from said ion-exchange material is distilled water.

18. A kit according to claim 1, further comprising a rigid holder for inserting said ion-exchange material in said medium, said holder being adapted to receive said ion-exchange material and maintain said ion-exchange material in contact with said medium when said ion-exchange material is inserted in said medium.

19. A kit according to claim 18, wherein said holder constitutes an applicator for inserting said ion-exchange material in said medium with minimal disturbance of said medium surrounding the location at which said ion-exchange material is contacted with said medium.

20. A kit according to claim 19, wherein said applicator comprises a leading edge capable of slicing said medium upon application of pressure on said holder.

21. A kit according to claim 1, wherein said medium is plant or animal tissue.

22. A kit according to claim 1, wherein said kit further comprises means for selecting a predetermined amount of said tissue.

23. A kit according to claim 1, wherein said ions are organic and inorganic ions and wherein said kit further comprises means for converting said organic ions into ions available for uptake by said ion-exchange material.

24. A kit according to claim 23, wherein said means for converting said organic ions into ions available for uptake by said ion-exchange material is an acid or an alkali.

25. A kit for measuring free inorganic ions in disrupted cells from a plant or animal tissue, said kit comprising:
   means for selecting a predetermined amount of said tissue;
   ion-exchange material having a measurable ion uptake potential; said ion exchange material being in an ionic form for immobilizing free inorganic ions from said cells following contact of said material with said tissue; and
   means to remove biological matter from said ion-exchange material after having contacted said tissue with said ion-exchange material.

26. A kit according to claim 25, wherein said means for selecting a predetermined amount of said tissue comprise means for at least partially disrupting the cells in said tissue.

27. A kit according to claim 25, wherein said ion-exchange material is pretreated to enhance immobilization of ions from said tissue onto said material when said material is in contact with said tissue.

28. A kit according to claim 27, wherein said ion-exchange material is pretreated to enhance immobilization of plant nutrients from said tissue onto said material when said material is inserted in said tissue.

29. A kit according to claim 28, wherein said material is pretreated to enhance immobilization of plant nutrients selected from the group consisting of nitrogen, phosphorous, potassium, sulphur, calcium, magnesium and micronutrients.

30. A kit according to claim 29, wherein said material is pretreated with dilute HCl or $NaHCO_3$.

31. A kit according to claim 27, wherein said material is pretreated with a chelating agent to enhance complexing and immobilization of trace metals from said medium onto said material when said material is contacted with said medium.

32. A kit according to claim 31, wherein said chelating agent is ethylenediamine tetraacetic acid or diethylenetriamine pentaacetic acid.

33. A kit according to claim 25, wherein said means to remove biological matter from said ion-exchange material is a washing solution characterized in that it is free from ions that can be immobilized on said ion-exchange material and free from ions that can displace ions immobilized on said ion-exchange material.

34. A kit according to claim 25, wherein said ions are organic and inorganic ions and wherein said kit further comprises means for converting said organic ions into ions available for uptake by said ion-exchange material.

35. A kit according to claim 34, wherein said means for converting said organic ions into ions available for uptake by said ion-exchange material is an acid or an alkali.

36. A method for the in situ measurement of available ions in a solid medium at a test site, said method comprising:
   directly contacting an ion-exchange material in the form of a film, sheet, or membrane with said solid medium;
   maintaining said ion-exchange material in said solid medium for a period of time sufficient for ions constituting extractable ion sources present in said solid medium to be immobilized on the surface of said ion-exchange material;

retrieving said ion-exchange material from said solid medium;

removing any adhering particles of the solid medium from said ion-exchange material; and immersing said ion-exchange material in a solution with sufficient ionic concentration to displace said ions immobilized on the surface of said ion-exchange material from said ion-exchange material to said solution.

37. A method according to claim 36, which further comprises measuring the amount of ions present in said solution to determine ion availability in said solid medium.

38. A method according to claim 37, wherein the amount of ions is measured using conventional colorimetry or spectrometry.

39. A method according to claim 36, wherein said ion-exchange material is inserted in soil or sediment at a distance ranging between 1.25 and 61 centimeters from the surface of said soil or sediment.

40. A method according to claim 36, wherein the ion-exchange material is cation, anion or zwitterion-exchange material.

41. A method according to claim 36, wherein said material is maintained in said soil or sediment for a period of time ranging from 15 seconds to 6 months.

42. A method according to claim 36, wherein said particles are removed from said material by washing said material with distilled water.

43. A method according to claim 36, wherein said solution is an acidic or a basic solution.

44. A method according to claim 43, wherein said acidic solution is a HCl solution having a concentration ranging between 0.1 and 0.5 M.

45. A method according to claim 36, wherein said method comprises an additional step by which said selected solid medium to be tested is pretreated to convert organic ions present in said solid medium into ions available for uptake by said ion-exchange material.

46. A method for measuring free inorganic ions in disrupted cells of plant or animal tissues, said method comprising:

selecting a predetermined amount of said tissue in which at least part of said cells are disrupted;

inserting ion-exchange material in the form of a film, sheet, or membrane of known surface area and having a measurable ion uptake potential in said tissue such that said ion-exchange material directly contacts said tissue;

maintaining said ion-exchange material in said tissue for a period of time sufficient for ions constituting extractable ion sources present in said tissue to be immobilized on the surface of said ion-exchange material;

retrieving said ion-exchange material from said tissue;

removing solid particles from said ion-exchange material; and immersing said ion-exchange material in a solution with sufficient ionic concentration to displace said ions immobilized on the surface of said ion-exchange material from said ion-exchange material into said solution.

47. A method according to claim 37, wherein said method comprises an additional step by which said tissue is pretreated to convert organic ions present in said tissue into ions available for uptake by said ion-exchange material.

48. An ion-exchange material for immobilizing available ions in a solid medium by direct contact of said ion-exchange material with said solid medium, said material comprising:

a surface adapted to immobilize ions in sufficient amounts to allow an accurate determination of their concentration and availability in said solid medium;

said material having a known surface area and a measurable ion uptake potential and being in the form of a film, sheet, or membrane; and said material being pretreated to enhance immobilization of said ions to be analyzed from said solid medium.

49. An ion-exchange material according to claim 48, wherein said ion-exchange material is cation or anion-exchange material.

50. An ion-exchange material according to claim 48, wherein said material is pretreated with a chelating agent to enhance complexing and immobilization of trace metals from said medium.

51. An ion-exchange material according to claim 50, wherein said chelating agent is ethylenediamine tetraacetic acid or diethylenetriamine pentaacetic acid.

52. An ion-exchange material according to claim 48, wherein said material has a surface area adapted for immersion of said material in a solution having sufficient ionic concentration to displace anions or cations immobilized on said material from said material into said solution.

53. An ion-exchange membrane buried underneath the surface of a soil sample or site, said membrane being in ion-exchange relationship with available ions in said solid medium.

54. A membrane according to claim 53, wherein said membrane is buried at a depth ranging from 1.25 to 61 centimeters below the surface of said soil sample or site.

55. A device for measuring available ions in a solid medium in situ, said device comprising:

ion-exchange material having a known surface area and a measurable ion uptake potential, said ion-exchange material being in an ionic form for immobilizing available ions from said medium on said material following direct in situ contact of said material with said medium; and a rigid holder for inserting said ion-exchange material in said medium, said holder being adapted to receive said ion-exchange material and maintain said ion-exchange material in contact with said medium.

56. A device according to claim 55, wherein said holder constitutes an applicator for inserting said ion-exchange material in said medium with minimal disturbance of said medium surrounding the location at which said ion-exchange material is contacted with said medium.

57. A device according to claim 56, wherein said applicator comprises a leading edge capable of slicing said medium upon application of pressure on said holder.

58. A device according to claim 55, wherein said ion-exchange material is a cation, anion or zwitterion-exchange material in the form of rigid or flexible films, sheets or membranes.

59. A device according to claim 55, wherein said ion-exchange material is pretreated to enhance immobilization of ions from said medium onto said material when said material is in contact with said medium.

60. A device according to claim 59, wherein said ion-exchange material is pretreated to enhance immobilization of plant nutrients from a solid medium onto said material when said material is inserted in a solid medium.

61. A device according to claim 60, wherein said material is pretreated to enhance immobilization of plant nutrients selected from the group consisting of nitrogen, phosphorous, potassium, sulphur, calcium, magnesium and micronutrients.

62. A device according to claim 61, wherein said material is pretreated with dilute HCl or $NaHCO_3$.

63. A device according to claim 59, wherein said material is pretreated with a chelating agent to enhance complexing and immobilization of trace metals from said medium onto said material when said material is contacted with said medium.

64. A device according to claim 63, wherein said chelating agent is ethylenediamine tetraacetic acid or diethylenetriamine pentaacetic acid.

65. A method according to claim 36 further comprising the step of moistening said solid medium at the site to be tested.

66. A kit according to claim 5, wherein the solution has a concentration in the range 0.1 to 0.5 M.

67. A kit according to claim 6, wherein the solution has a concentration in the range 0.1 to 0.5 M.

68. A kit according to claim 2, wherein said ion-exchange material is anion-exchange material in the from of polystyrene cross-linked with vinylbenzene and having attached thereto quaternary ammonium moieties.

69. A kit according to claim 9, wherein said cationic-exchange material is contained in a solution of hydrochloric acid or sodium bicarbonate whose concentration is in the range of 0.1 to 0.5 M.

70. A kit according to claim 68, wherein the anion-exchange material is contained in a solution of hydrochloric acid or sodium bicarbonate whose concentration is in the range of 0.1 to 0.5 M.

* * * * *